US009066519B2

(12) United States Patent
Witschel et al.

(10) Patent No.: US 9,066,519 B2
(45) Date of Patent: Jun. 30, 2015

(54) HERBICIDAL BENZOXAZINONES

(71) Applicants: Matthias Witschel, Bad Dürkheim (DE); Trevor William Newton, Neustadt (DE); Thomas Seitz, Viernheim (DE); Helmut Walter, Obrigheim (DE); Bernd Sievernich, Haβloch (DE); Anja Simon, Weinheim (DE); Ricarda Niggeweg, Mannheim (DE); Klaus Groβmann, Neuhofen (DE); Liliana Parra Rapado, Offenburg (DE); Richard Roger Evans, Limburgerhof (DE)

(72) Inventors: Matthias Witschel, Bad Dürkheim (DE); Trevor William Newton, Neustadt (DE); Thomas Seitz, Viernheim (DE); Helmut Walter, Obrigheim (DE); Bernd Sievernich, Haβloch (DE); Anja Simon, Weinheim (DE); Ricarda Niggeweg, Mannheim (DE); Klaus Groβmann, Neuhofen (DE); Liliana Parra Rapado, Offenburg (DE); Richard Roger Evans, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/268,411

(22) Filed: May 2, 2014

(65) Prior Publication Data

US 2014/0243522 A1    Aug. 28, 2014

Related U.S. Application Data

(62) Division of application No. 13/378,137, filed as application No. PCT/EP2010/058195 on Jun. 11, 2010, now Pat. No. 8,754,008.

(30) Foreign Application Priority Data

Jun. 19, 2009  (EP) .................................... 09163242
Sep. 2, 2009   (EP) .................................... 09169219

(51) Int. Cl.
*A01N 43/84*    (2006.01)
*C07D 265/36*   (2006.01)
*C07C 233/25*   (2006.01)
*C07D 413/04*   (2006.01)

(52) U.S. Cl.
CPC .............. *A01N 43/84* (2013.01); *C07C 233/25* (2013.01); *C07D 265/36* (2013.01); *C07D 413/04* (2013.01)

(58) Field of Classification Search
CPC .............................. C07D 265/84; A01N 43/84
USPC ....................................................... 544/105
See application file for complete search history.

(56) References Cited

U.S. PATENT DOCUMENTS

| | | | |
|---|---|---|---|
| 5,080,710 A | 1/1992 | Rueb et al. |
| 5,215,570 A | 6/1993 | Burckhardt et al. |
| 5,529,974 A | 6/1996 | Kerber |
| 5,532,203 A | 7/1996 | Foery et al. |
| 6,235,680 B1 | 5/2001 | Ziemer et al. |
| 8,445,407 B2 | 5/2013 | Witschel et al. |
| 2011/0015068 A1 | 1/2011 | Sievernich et al. |
| 2011/0086762 A1 | 4/2011 | Fischer et al. |
| 2013/0102463 A1 | 4/2013 | Ehrhardt et al. |

FOREIGN PATENT DOCUMENTS

| | | |
|---|---|---|
| CN | 1687061 | 10/2005 |
| CN | 100386324 | 5/2008 |
| EP | 0 170 191 | 2/1986 |
| EP | 0 365 484 | 10/1989 |
| EP | 0 413 832 | 2/1991 |
| EP | 0448188 A2 | 9/1991 |
| EP | 064600 A1 | 3/1995 |
| EP | 2 103 615 | 9/2009 |
| JP | 2000247975 | 9/2000 |
| JP | 2006-36706 A | 2/2006 |
| WO | WO 90/06748 | 6/1990 |
| WO | WO 90/10626 | 8/1990 |
| WO | WO 92/06962 | 4/1992 |
| WO | WO 93/15074 | 8/1993 |
| WO | WO 94/03454 | 2/1994 |
| WO | WO 94/14817 | 7/1994 |
| WO | WO 97/07104 | 2/1997 |
| WO | WO 97/45016 | 12/1997 |
| WO | WO 2002066471 | 8/2002 |
| WO | WO 2010/003444 | 1/2010 |
| WO | WO 2010/040485 | 4/2010 |
| WO | WO 2010/145992 | 12/2010 |
| WO | WO 2011/018486 | 2/2011 |
| WO | WO 2010/051393 | 5/2011 |
| WO | WO 2011/057935 | 5/2011 |
| WO | WO 2012/041789 | 4/2012 |
| WO | WO 2012/080239 | 6/2012 |

OTHER PUBLICATIONS

International Search Report dated Apr. 24, 2012, prepared in International Application No. PCT/EP2011/072596.
International Preliminary Report on Patentability dated Jun. 18, 2013, prepared in International Application No. PCT/EP2011/072596.
Haga et al., "Acid-Catalyzed Amino-Migration of O-Phenylhydroxylamines", J. Am. Chem. Soc., vol. 114, 1992, pp. 9795-9806.
Office Action dated Oct. 1, 2013 in co-pending U.S. Appl. No. 13/993,943.
Office Action dated Jul. 31, 2013 in co-pending U.S. Appl. No. 13/876,330.
International Search Report for PCT/EP2010/058195, Aug. 19, 2010.
International Preliminary Report on Patentability for PCT/EP2010/058195, Dec. 19, 2011.

*Primary Examiner* — Kahsay Habte
(74) *Attorney, Agent, or Firm* — Brinks Gilson & Lione

(57) ABSTRACT

The present invention relates to benzoxazinones of the general formula (I)

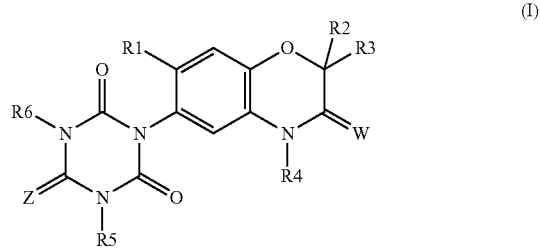

(I)

wherein the variables are defined according to the description, processes and intermediates for preparing the benzoxazinones of the formula (I), compositions comprising them and their use as herbicides, i.e. for controlling harmful plants, and also a method for controlling unwanted vegetation which comprises allowing a herbicidal effective amount of at least one benzoxazinones of the formula (I) to act on plants, their seed and/or their habitat.

10 Claims, No Drawings

HERBICIDAL BENZOXAZINONES

This application is a divisional application of U.S. Ser. No. 13/378,137, filed Dec. 14, 2011, which is a National Stage application of International Application No. PCT/EP2010/058195 filed Jun. 11, 2010, the entire contents of which are hereby incorporated herein by reference. This application also claims priority under 35 U.S.C. §119 to EP Patent Application No. 09163242.2, filed Jun. 19, 2009, and EP Patent Application No. 09169219.4, filed Sep. 2, 2009, the entire contents of which is hereby incorporated herein by reference.

The present invention relates to benzoxazinones of the general formula I defined below and to their use as herbicides. Moreover, the invention relates to compositions for crop protection and to a method for controlling unwanted vegetation.

WO 02/066471 describes structurally similar compounds for which herbicidal action is stated, which differ from the benzoxazinones I according to the present invention that the benzo[1,4]oxazine ring is unsubstituted in the 2-position, whereas the benzoxazinones of formula I according to the present invention are substituted in said position by at least one halogen atom.

However, the herbicidal properties of these known compounds with regard to the harmful plants are not always entirely satisfactory.

It is therefore an object of the present invention to provide benzoxazinones having improved herbicidal action. To be provided are in particular benzoxazinones which have high herbicidal activity, in particular even at low application rates, and which are sufficiently compatible with crop plants for commercial utilization.

These and further objects are achieved by the benzoxazinones of the formula I, defined below, and by their agriculturally suitable salts.

Accordingly, the present invention provides benzoxazinones of formula I

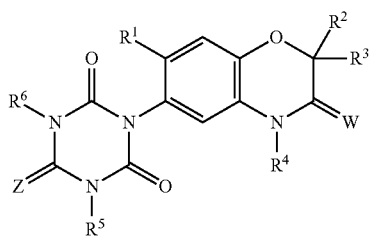

wherein
$R^1$ is hydrogen or halogen;
$R^2$ is halogen;
$R^3$ is hydrogen or halogen;
$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^5$ is hydrogen, $NH_2$, $C_1$-$C_6$-alkyl or $C_3$-$C_6$-alkynyl;
$R^6$ is hydrogen or $C_1$-$C_6$-alkyl; and
W is O or S;
Z is O or S.

The present invention also provides the use of benzoxazinones of the general formula I as herbicides, i.e. for controlling harmful plants.

The present invention also provides compositions comprising at least one benzoxazinone of the formula I and auxiliaries customary for formulating crop protection agents.

The present invention furthermore provides a method for controlling unwanted vegetation where a herbicidal effective amount of at least one benzoxazinone of the formula I is allowed to act on plants, their seeds and/or their habitat. Application can be done before, during and/or after, preferably during and/or after, the emergence of the undesirable plants.

Moreover, the invention relates to processes and intermediates for preparing benzoxazinones of the formula I.

The present invention further relates to herbicidally active compositions comprising at least one benzoxazinone of formula I and at least one further compound selected from herbicidally active compounds and safeners.

In the case of crop protection compositions, it is desirable in principle to increase the specific activity of an active compound and the reliability of the effect. It is particularly desirable for the crop protection composition to control the harmful plants effectively, but at the same time to be compatible with the useful plants in question. Also desirable is a broad spectrum of activity allowing the simultaneous control of harmful plants. Frequently, this cannot be achieved using a single herbicidally active compound.

With many highly effective herbicides, there is the problem that their compatibility with useful plants, in particular dicotyledonous crop plants, such as cotton, oilseed rape and graminaceous plants, such as barley, millet, corn, rice, wheat and sugar cane, is not always satisfactory, i.e. in addition to the harmful plants, the crop plants, too, are damaged on a scale which cannot be tolerated. By reducing the application rates, the useful plants are spared; however, naturally, the extent of the control of harmful plants decreases, too.

Frequently, it is a problem that herbicides can only be applied within a narrow time frame in order to achieve the desired herbicidal action, which time frame may be unpredictably influenced by weather conditions.

It is known that special combinations of different specifically active herbicides result in enhanced activity of a herbicide component in the sense of a synergistic effect. In this manner, it is possible to reduce the application rates of herbicidally active compounds required for controlling the harmful plants.

Furthermore, it is known that in some cases joint application of specifically acting herbicides with organic active compounds, some of which may also have herbicidal activity, allows better crop plant compatibility to be achieved. In these cases, the active compounds act as antidotes or antagonists and are also referred to as safeners, since they reduce or even prevent damage to the crop plants.

It is a further object of the present invention to provide also herbicidal compositions which are highly active against unwanted harmful plants. At the same time, the compositions should have good compatibility with useful plants. In addition, the compositions according to the invention should have a broad spectrum of activity.

This and further objects are achieved by the herbicidally active compositions below.

Accordingly, the present invention also relates to herbicidally active compositions comprising:

A) at least one benzoxazinone of the formula I

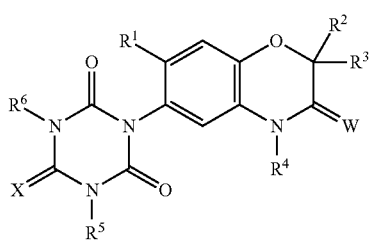

wherein
$R^1$ is hydrogen or halogen;
$R^2$ is halogen;
$R^3$ is hydrogen or halogen;
$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^5$ is hydrogen, $NH_2$, $C_1$-$C_6$-alkyl or $C_3$-$C_6$-alkynyl;
$R^6$ is hydrogen or $C_1$-$C_6$-alkyl; and
X is O or S;
Y is O or S;
and at least one further active compound selected from
B) herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitose inhibitors;
b10) inhibitors of the synthesis of very long chain fatty acids (VLCFA inhibitors);
b11) cellulose biosynthesis inhibitors;
b12) decoupler herbicides;
b13) auxin herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
and
C) safeners.

One embodiment of the invention relates in particular to compositions in the form of herbicidally active crop protection compositions comprising a herbicidally effective amount of an active compound combination comprising at least one benzoxazinone of formula I and at least one further compound selected from the herbicides B and the safeners C, as defined above, and also at least one liquid and/or solid carrier and/or one or more surfactants and, if desired, one or more further auxiliaries customary for crop protection compositions.

Further, the invention also relates to compositions in the form of a crop protection composition formulated as a 1-component composition comprising an active compound combination comprising at least one benzoxazinone of formula I and at least one further active compound selected from the herbicides B and the safeners C, and at least one solid or liquid carrier and/or one or more surfactants and, if desired, one or more further auxiliaries customary for crop protection compositions.

Further, the invention also relates to compositions in the form of a crop protection composition formulated as a 2-component composition comprising a first component comprising at least one benzoxazinone of formula I, a solid or liquid carrier and/or one or more surfactants, and a second component comprising at least one further active compound selected from the herbicides B and safeners C, a solid or liquid carrier and/or one or more surfactants, where additionally both components may also comprise further auxiliaries customary for crop protection compositions.

Surprisingly, the compositions according to the invention comprising at least one benzoxazinone of formula I and at least one herbicide B have better herbicidal activity, i.e. better activity against harmful plants, than would have been expected based on the herbicidal activity observed for the individual compounds, or a broader activity spectrum. The herbicidal activity to be expected for mixtures based on the individual compound can be calculated using Colby's formula (see below). If the activity observed exceeds the expected additive activity of the individual compounds, synergism is said to be present.

Moreover, the time frame, within which the desired herbicidal action can be achieved, may be expanded by the compositions according to the invention comprising at least one benzoxazinone of formula I and at least one herbicide B and optionally a safener C. This allows a more flexibly timed application of the compositions according to the present invention in comparison with the single compounds.

The compositions according to the invention comprising both at least one benzoxazinone of formula I and at least one of the compounds mentioned under C also have good herbicidal activity against harmful plants and better compatibility with useful plants.

Surprisingly, the compositions according to the invention comprising at least one benzoxazinone of formula I, at least one herbicide B and at least one of the compounds mentioned under C have better herbicidal activity, i.e. better activity against harmful plants, than would have been expected based on the herbicidal activity observed for the individual compounds, or a broader activity spectrum, and show better compatibility with useful plants than compositions comprising only one compound I and one herbicide B.

The invention furthermore relates to a method for controlling unwanted vegetation, in particular where crop plants are cultivated, for example in crops of the following crop plants: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus*

*tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera, Zea mays*, especially crops of cereals, corn, soybeans, rice, oilseed rape, cotton, potatoes, peanuts or permanent crops, and also in crops which are resistant to one or more herbicides or to attack by insects owing to genetic engineering or breeding.

The invention also relates to a method for the desiccation or defoliation of plants. In the last-mentioned method, it is of no importance whether the herbicidally active compounds of components A) and B) and, if appropriate, C) are formulated and applied jointly or separately, and in which order application is carried out in case of separate application.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms. As used herein, the terms "undesirable vegetation" and "harmful plants" are synonyms.

If the benzoxazinones of formula I as described herein are capable of forming geometrical isomers, for example E/Z isomers, it is possible to use both, the pure isomers and mixtures thereof, in the compositions according to the invention.

If the benzoxazinones of formula I as described herein have one or more centers of chirality and, as a consequence, are present as enantiomers or diastereomers, it is possible to use both, the pure enantiomers and diastereomers and their mixtures, in the compositions according to the invention.

The organic moieties mentioned in the definition of the variables $R^1$ to $R^6$, are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl and also the $C_1$-$C_4$-alkyl moieties of $C_3$-$C_6$-cycloalkyl-$C_1$-$C_4$-alkyl: for example $CH_3$, $C_2H_5$, n-propyl, and $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_4$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

C₃-C₆-haloalkenyl: a C₃-C₆-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

C₃-C₆-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

C₃-C₆-haloalkynyl: a C₃-C₆-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy and also the $C_1$-$C_4$-alkoxy moieties of hydroxycarbonyl-$C_1$-$C_4$-alkoxy, $C_1$-$C_6$-alkoxycarbonyl-$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkoxycarbonyl-$C_1$-$C_4$-alkoxy: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

The preferred embodiments of the invention mentioned herein below have to be understood as being preferred either independently from each other or in combination with one another.

According to a preferred embodiment of the invention preference is also given to those benzoxazinones of formula I, wherein the variables, either independently of one another or in combination with one another, have the following meanings:

$R^1$ is hydrogen;
  is also preferably halogen, particularly preferred F or Cl, especially preferred F;
$R^2$ is F;
$R^3$ is hydrogen or F, preferably hydrogen;
  is also preferably F;
$R^4$ is $C_3$-$C_6$-alkynyl or $C_3$-$C_6$-haloalkynyl, preferably $C_3$-alkynyl or $C_3$-haloalkynyl, particularly preferred CH₂C≡CH, CH₂C≡CCl or CH₂C≡CBr;
  is also preferably $C_3$-$C_6$-alkynyl or $C_3$-$C_6$-cycloalkyl-$C_1$-$C_6$-alkyl, particularly preferred propargyl or cyclopropylmethyl;
  is also preferably $C_3$-$C_6$-alkynyl, preferably $C_3$-alkynyl; particularly preferred CH₂C≡CH;
  is also preferably $C_3$-$C_6$-halolkynyl, preferably $C_3$-halolkynyl, particularly preferred CH₂C≡CCl or CH₂C≡CBr;
$R^5$ is NH₂, $C_1$-$C_6$-Alkyl or $C_3$-$C_6$-alkynyl; preferably $C_1$-$C_6$-alkyl; more preferably $C_1$-$C_4$-alkyl; most preferably CH₃;
$R^6$ is $C_1$-$C_6$-alkyl; preferably $C_1$-$C_4$-alkyl; most preferably CH₃;
W is O,
  is also preferably S;
Z is O,
  is also preferably S.

Particular preference is given to benzoxazinones of the formula I.a (corresponds to formula I wherein $R^2$ is F, $R^5$ and $R^6$ are CH₃, W is O and Z is S),

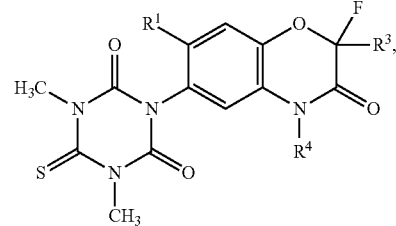

I.a wherein the variables $R^1$, $R^3$, and $R^4$ have the meanings, in particular the preferred meanings, as defined above;

most preference to the compounds of the formulae I.a.1 to I.a.48 of Table A listed below, in which the variables $R^1$, $R^3$ and $R^4$ together have the meanings given in one row of Table A (benzoxazinones I.a.1 to I.a.54); and where the definitions of the variables $R^1$, $R^2$, $R^3$ and $R^4$ are of particular importance for the compounds according to the invention not only in combination with one another but in each case also on their own:

TABLE A

| No. | $R^1$ | $R^3$ | $R^4$ |
|---|---|---|---|
| I.a.1. | H | H | H |
| I.a.2. | H | H | CH₃ |
| I.a.3. | H | H | C₂H₅ |
| I.a.4. | H | H | CH₂—C₂H₅ |
| I.a.5. | H | H | CH(CH₃)₂ |
| I.a.6. | H | H | CH₂—CH₂—(CH₃)₂ |
| I.a.7. | H | H | CH₂—CH=CH₂ |
| I.a.8. | H | H | CH₂C≡CH |
| I.a.9. | H | H | CH₂C≡C—Br |
| I.a.10. | H | F | H |
| I.a.11. | H | F | CH₃ |
| I.a.12. | H | F | C₂H₅ |
| I.a.13. | H | F | CH₂—C₂H₅ |
| I.a.14. | H | F | CH(CH₃)₂ |
| I.a.15. | H | F | CH₂—CH₂—(CH₃)₂ |
| I.a.16. | H | F | CH₂—CH=CH₂ |
| I.a.17. | H | F | CH₂C≡CH |
| I.a.18. | H | F | CH₂C≡C—Br |
| I.a.19. | F | H | H |
| I.a.20. | F | H | CH₃ |
| I.a.21. | F | H | C₂H₅ |
| I.a.22. | F | H | CH₂—C₂H₅ |
| I.a.23. | F | H | CH(CH₃)₂ |
| I.a.24. | F | H | CH₂—CH₂—(CH₃)₂ |

TABLE A-continued

| No. | R$^1$ | R$^3$ | R$^4$ |
|---|---|---|---|
| I.a.25. | F | H | CH$_2$—CH=CH$_2$ |
| I.a.26. | F | H | CH$_2$C≡CH |
| I.a.27. | F | H | CH$_2$C≡C—Br |
| I.a.28. | F | F | H |
| I.a.29. | F | F | CH$_3$ |
| I.a.30. | F | F | C$_2$H$_5$ |
| I.a.31. | F | F | CH$_2$—C$_2$H$_5$ |
| I.a.32. | F | F | CH(CH$_3$)$_2$ |
| I.a.33. | F | F | CH$_2$—CH$_2$—(CH$_3$)$_2$ |
| I.a.34. | F | F | CH$_2$—CH=CH$_2$ |
| I.a.35. | F | F | CH$_2$C≡CH |
| I.a.36. | F | F | CH$_2$C≡C—Br |
| I.a.37. | Cl | H | H |
| I.a.38. | Cl | H | CH$_3$ |
| I.a.39. | Cl | H | C$_2$H$_5$ |
| I.a.40. | Cl | H | CH$_2$—C$_2$H$_5$ |
| I.a.41. | Cl | H | CH(CH$_3$)$_2$ |
| I.a.42. | Cl | H | CH$_2$—CH$_2$—(CH$_3$)$_2$ |
| I.a.43. | Cl | H | CH$_2$—CH=CH$_2$ |
| I.a.44. | Cl | H | CH$_2$C≡CH |
| I.a.45. | Cl | H | CH$_2$C≡C—Br |
| I.a.46. | Cl | F | H |
| I.a.47. | Cl | F | CH$_3$ |
| I.a.48. | Cl | F | C$_2$H$_5$ |
| I.a.49. | Cl | F | CH$_2$—C$_2$H$_5$ |
| I.a.50. | Cl | F | CH(CH$_3$)$_2$ |
| I.a.51. | Cl | F | CH$_2$—CH$_2$—(CH$_3$)$_2$ |
| I.a.52. | Cl | F | CH$_2$—CH=CH$_2$ |
| I.a.53. | Cl | F | CH$_2$C≡CH |
| I.a.54. | Cl | F | CH$_2$C≡C—Br |

An especially preferred benzoxazinone of the formula I which, as component A, is part of the composition according to the invention, is the benzoxazinone of formula I.a.35 as defined above

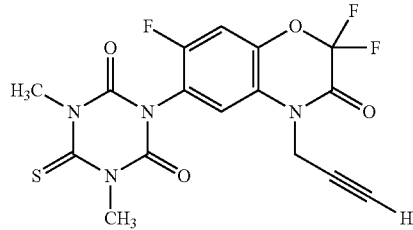

I.a.35

According to a particular preferred embodiment of the invention the composition contains as component A the benzoxazinone of formula I.a.35.

The benzoxazinones of formula I according to the invention can be prepared by standard processes of organic chemistry, for example by the following processes:

Process A)

In analogy to J. Chem. Soc. Perkin Trans. (1982), p. 1321:

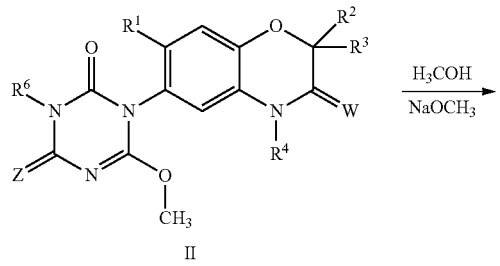

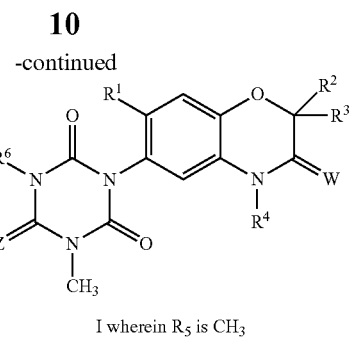

I wherein R$_5$ is CH$_3$

The reaction is conducted as specified in the publication stated.

Process B)

Reaction of isocyanate compounds IV.d with ureas III, followed by cyclization of the urea compounds IV.e:

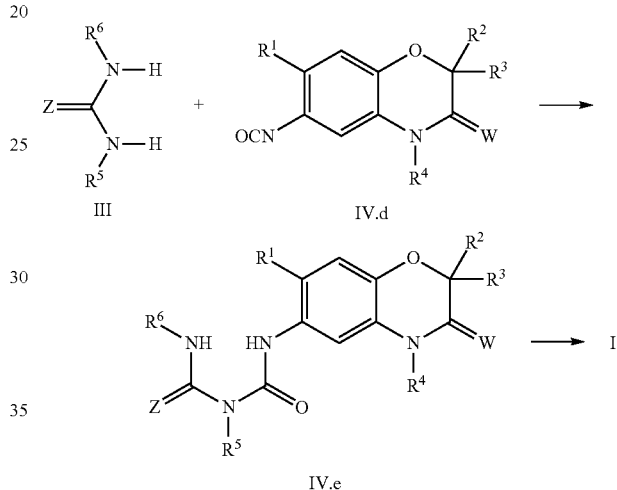

The isocyanate compounds IV.d are reacted with the ureas III. The cyclization of the urea compounds IV.e is carried out in the presence of an activated carbonyl source such as carbonyldiimidazole, phosgene, diphosgene, triphosgene and chloroformic ester, preferably without isolation of the intermediate IV.e.

The reaction of the urea III with the isocyanate compound IV.d as well as the subsequent cyclization of the urea compounds IV.e are usually carried out at from −20° C. to the boiling point of the reaction mixture, preferably at from 20° C. to 200° C., particularly preferably at from 50° C. to 120° C., in an inert organic solvent in the presence of a base and, if appropriate, a catalyst [I. Wakeshima et. a., Bull. Chem. Soc. 1975, 48 (3), 1069-70].

Suitable solvents are aliphatic hydrocarbons such as pentane, hexane, cyclohexane and mixtures of C$_5$-C$_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, nitriles such as acetonitrile and propionitrile, ketones such as acetone, methyl ethyl ketone, diethyl ketone and tert-butyl methyl ketone, as well as dimethylsulfoxide, dimethylformamide and N,N-dimethylacetamide or N-methylpyrrolidone. Particular preference is given to aromatic hydrocarbons such as toluene, o-, m- and p-xylene.

It is also possible to use mixtures of the solvents mentioned.

Suitable bases are, in general inorganic compounds such as alkali metal and alkaline earth metal oxide such as lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to tertiary amines such as triethylamine.

The bases are generally employed in catalytic amounts, however they can also be employed in equimolar amounts, in excess or, if appropriate, be used as solvent.

As acidic catalysts Lewis acids like boron trifluoride, aluminium chloride, ferric-III-chloride, tin-IV-chloride, titanium-IV-chloride and zinc-II-chloride, can be used.

The acids are generally employed in catalytic amounts, however they can also be employed in equimolar amounts, in excess or, if appropriate, be used as solvent.

The reaction mixtures are worked up in a customary manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature. If the intermediates and the end products are obtained as solid, purification can also be carried out by recrystallisation or digestion.

The isocyanate compounds IV.d in turn can be obtained from the corresponding amine compounds IV.c:

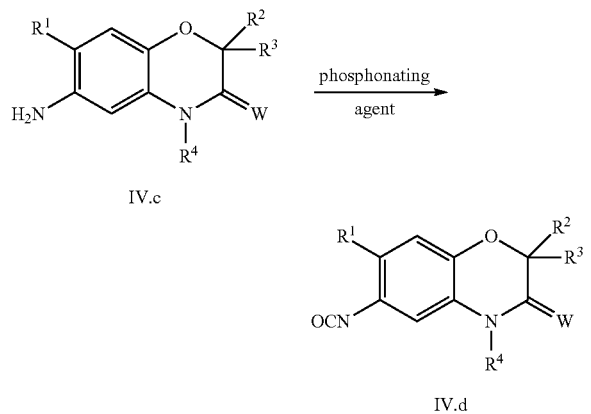

Suitable phosgenating agents are phosgene, diphosgene or triphosgene, diphosgene being preferred.

The reaction of the amine IV.c is usually carried out at from −20° C. to the boiling point of the reaction mixture, preferably at from 10° C. to 200° C., particularly preferably at from 20° C. to 150° C., in an inert organic solvent and, if appropriate, in the presence of a base.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide. Particular preference is given to aromatic hydrocarbons such as toluene, o-, m- and p-xylene.

It is also possible to use mixtures of the solvents mentioned.

Suitable bases are, in general inorganic compounds such as alkali metal and alkaline earth metal carbonates such as lithium carbonate, potassium carbonate and calcium carbonate, as well as alkali metal bicarbonates such as sodium bicarbonate, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to tertiary amines such as triethylamine.

The bases are generally employed in catalytic amounts, however they can also be employed in equimolar amounts, in excess or, if appropriate, be used as solvent.

Work up can be carried out in a known manner.

The amino compounds IV.c in turn can be obtained from the corresponding nitro compounds IV.b:

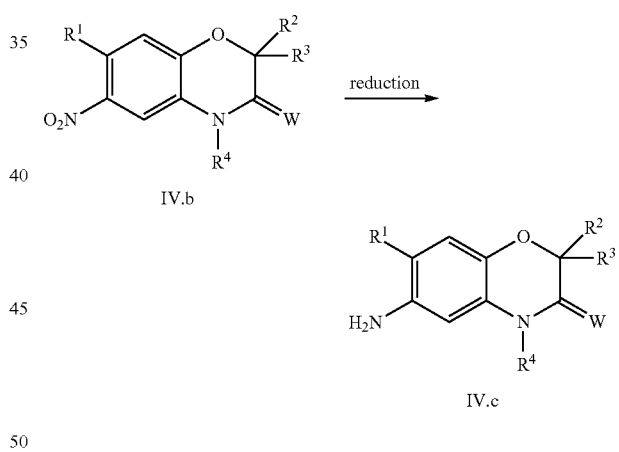

The reduction of the nitro compounds IV.b is usually carried out at from 20° C. to the boiling point of the reaction mixture, preferably at from 20° C. to 200° C., particularly preferably at from 20° C. to 100° C., in an inert organic solvent [Organikum, Heidelberg, 1993, pages 320-323].

Suitable reducing agents are nascent $H_2$; hydrogen in the presence of catalytic amounts of transition metals or transition metal compounds, in particular those of the $8^{th}$ transition group, preferably Ni, Pd, Pt, Ru or Rh, either as such, in supported form e.g. supported via activated carbon, Al, $ZrO_2$, $TiO_2$, $SiO_2$, carbonates and the like, or in compounds such as palladium oxide or platinum oxide; or metal hydrides, semimetal hydrides such as aluminium hydride and hydrides derived therefrom such as lithium aluminium hydride, diisobutylaluminiumhydride, borohydrides such as diborane or boranates derived therefrom such as sodium borohydride or lithium borohydride.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, alcohols such as methanol, ethanol, n-propanol, isopropanol, n-butanol and tert.-butanol. Particular preference is given to toluene and methanol. It is also possible to use mixtures of the solvents mentioned.

Work up can be carried out in a known manner.

The nitro compounds IV.b in turn can be obtained from the corresponding phenyl compounds IVa:

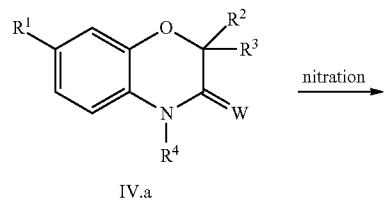

IV.a

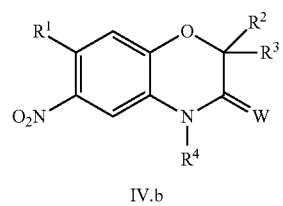

IV.b

The nitration of the phenyl compound IV.a is usually carried out at from −20° C. to 100° C., particularly preferably at from 0° C. to 20° C. [Organikum, Heidelberg, 1993, pages 553-557]. Suitable nitrating agents are mixtures of $H_2SO_{4\,conc}$ and $HNO_{3\,conc}$, preferably in a range of 50:1 to 1:50, more preferably 20:1 to 1:20, especially preferred in a range of 10:1 to 1:10.

Work up can be carried out in a known manner.

Those nitro compounds IV.b, wherein $R^4$ is $C_3$-$C_6$-alkenyl, $C_3$-$C_6$-haloalkenyl, $C_3$-$C_6$-alkynyl or $C_3$-$C_6$-haloalkynyl, preferably $C_3$-$C_6$-alkynyl, can also be prepared by alkylation of nitro compounds IV.b, wherein $R^4$ is H:

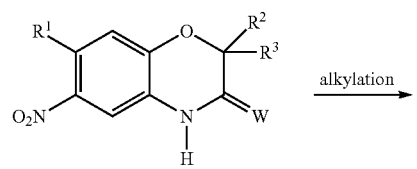

IV.b, wherein $R^4$ is H

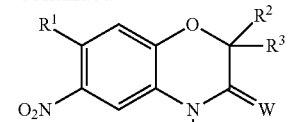

IV.b, wherein $R^4$ is
$C_3$—$C_6$-alkenyl, $C_3$—$C_6$-haloalkenyl
$C_3$—$C_6$-alkynyl, $C_3$—$C_6$-haloalkynyl This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide. Particular preference is given to ethers such as diethyl ether, diisopropyl ether, tert.-butyl methyl ether, dioxane, anisole and tetrahydrofuran.

It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Particular preference is given to tertiary amines such as trimethylamine, triethylamine, diisopropylethylamine and alkali metal and alkaline earth metal alkoxides such as sodium methoxide, sodium ethoxide, potassium ethoxide. The bases are generally employed in catalytic amounts, however they can also be employed in equimolar amounts, in excess or, if appropriate, be used as solvent.

Work up can be carried out in a known manner.

The phenyl compounds IV.a in turn can be obtained from the corresponding acetamides V:

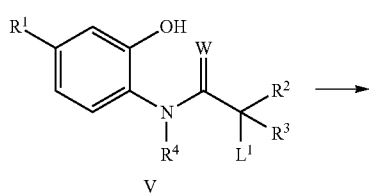

V

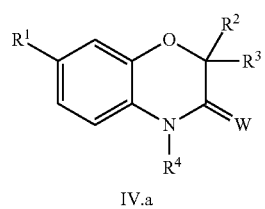

IV.a

The cyclisation of the acetamide V is usually carried out at from 0° C. to the boiling point of the reaction mixture, preferably at from 0° C. to 140° C., particularly preferably at from 20° C. to 120° C., in an inert organic solvent in the presence of a base [WO 02/066471].

$L^1$ is halogen selected from Cl, Br, I; preferably Cl or Br; most preferably Cl, also most preferably Br.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, as well as dimethylsulfoxide.

It is also possible to use mixtures of the solvents mentioned.

Suitable bases are, in general inorganic compounds such as alkali metal and alkaline earth metal hydroxides such as lithium hydroxide, sodium hydroxide, potassium hydroxide and calcium hydroxide, alkali metal and alkaline earth metal oxide such as lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, metal organic compounds, preferably alkali metal alkyls such as methyl lithium, butyl lithium and phenyl lithium, alkyl magnesium halides such as methyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to 1,8-Diazabicyclo[5.4.0]undec-7-en (DBU).

The bases are generally employed in catalytic amounts, however they can also be employed in equimolar amounts, in excess or, if appropriate, be used as solvent.

Work up can be carried out in a known manner.

The acetamides V in turn can be obtained from the corresponding phenol VI:

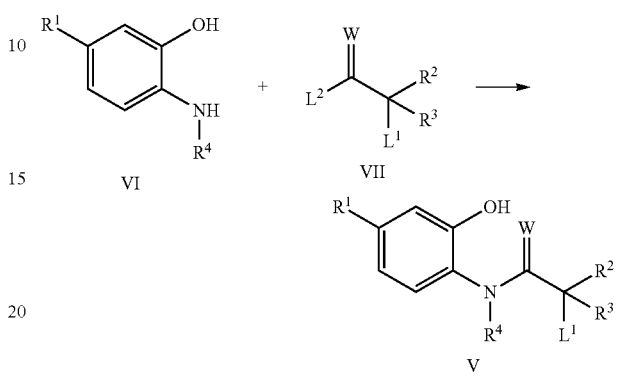

This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

$L^1$ is halogen selected from Cl, Br, I; preferably Cl or Br; most preferably Cl, also most preferably Br.

$L^2$ is a known activating group for acylations, e.g. halogen or $C_1$-$C_6$-alkoxy, preferably Cl or $C_1$-$C_6$-alkoxy, most preferably Cl, $OCH_3$ or $OC_2H_5$.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide. Particular preference is given to ethers such as diethyl ether, diisopropyl ether, tert.-butyl methyl ether, dioxane, anisole and tetrahydrofuran.

It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to tertiary amines such as trimethylamine, triethylamine, diisopropylethylamine and alkali metal and alkaline earth metal alkoxides such as sodium methoxide, sodium ethoxide, potassium ethoxide. The bases are generally employed in catalytic amounts, however they can also be employed in equimolar amounts, in excess or, if appropriate, be used as solvent.

Work up can be carried out in a known manner.

The phenols VI required for the preparation of the acetamides V are known from the literature [WO 02/066471] or they can be prepared in accordance with the literature cited and/or are commercially available.

The compounds VII required for the preparation of the acetamides V are commercially available.

Process C)

Alkylation of benzoxazinones of formula I where $R^4$ is hydrogen in a manner known per se (e.g. see also above for the nitro compounds IV.b) leads to benzoxazinones of formula I, wherein $R^4$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl or $C_3$-$C_6$-cycloalkyl-$C_1$-$C_6$-alkyl. The alkylation is carried out in a manner known per se, for example, using an alkylating reagent, e.g. a halide $R^4$—Hal, in the presence of a base, in a solvent.

Processes A) and C) are preferably carried out in the presence of a suitable reaction auxiliary.

Suitable reactants are, in general, the customary inorganic or organic bases and acid acceptors. These preferably include the acetates, amides, carbonates, hydrogencarbonates, hydrides, hydroxides and alkoxides of alkali metals and alkaline earth metals, i.e., for example, sodium acetate, potassium acetate, calcium acetate, lithium amide, sodium amide, potassium amide, calcium amide, sodium carbonate, potassium carbonate, calcium carbonate, sodium hydrogen carbonate, potassium hydrogen carbonate, calcium hydrogen carbonate, lithium hydride, sodium hydride, potassium hydride, calcium hydride, lithium hydroxide, sodium hydroxide, potassium hydroxide, calcium hydroxide, sodium methoxide, sodium ethoxide, sodium n-propoxide, sodium isopropoxide, sodium n-butoxide, sodium isobutoxide, sodium sec-butoxide, sodium tert-butoxide, potassium methoxide, potassium ethoxide, potassium n-propoxide, potassium isopropoxide, potassium n-butoxide, potassium isobutoxide, potassium sec-butoxide, potassium tert-butoxide; furthermore also basic organic nitrogen compounds, for example trimethylamine, triethylamine, tripropylamine, tributylamine, ethyldiisopropylamine, N,N-dimethylcyclohexylamine, dicyclohexylamine, ethyldiisopropylamine, N,N-dimethylaniline, N,N-dimethylbenzylamine, pyridine, 2-methylpyridine, 3-methylpyridine, 4-methylpyridine, 2,4-dimethylpyridine, 2,6-dimethylpyridine, 3,4-dimethylpyridine and 3,5-dimethylpyridine, 5-ethyl-2-methylpyridine, 4-dimethylaminopyridine, N-methylpiperidine, 1,4-diazabicyclo[2,2,2]octane (DABCO), 1,5-diazabicyclo[4,3,0]non-5-ene (DBN) or 1,8-diazabicyclo[5,4,0]undec-7-ene (DBU).

Processes A) and C) are usually carried out in the presence of an inert diluent, suitable diluents generally being the usual organic solvents. These preferably include aliphatic, alicyclic and aromatic, optionally halogenated hydrocarbons, for example pentane, hexane, heptane, petroleum ether, ligroin, benzene, toluene, the xylenes, chlorobenzenes, dichlorobenzenes, cyclohexane, methylcyclohexane, dichloromethane, trichloromethane, tetrachloromethane, dialkyl ethers such as diethyl ether, diisopropyl ether, methyl tert-butyl ether (MTBE), ethyl tert-butyl ether, methyl tert-pentyl ether (TAME), ethyl tert-pentyl ether, tetrahydrofuran, 1,4-dioxane, ethylene glycol dimethyl ether, ethylene glycol diethyl ether, diethylene glycol dimethyl ether, diethylene glycol diethyl ether; dialkyl ketones such as acetone, butanone (methyl ethyl ketone), methyl isopropyl ketone and methyl isobutyl ketone; nitriles such as acetonitrile, propionitrile, butyronitrile and benzonitrile; amides such as N,N-dimethylformamide, N,N-dimethylacetamide, N-methylformanilide, N-methylpyrrolidone and hexamethylphosphoric triamide; esters such as methyl acetate, ethyl acetate, n-propyl acetate, isopropyl acetate, n-butyl acetate, isobutyl acetate and sec-butyl acetate; sulfoxides such as dimethyl sulfoxide; alkanols such as methanol, ethanol, n-propanol, isopropanol, n-butanol, isobutanol, sec-butanol and tert-butanol; glycol ethers such as ethylene glycol monomethyl ether, ethylene glycol monoethyl ether, diethylene glycol monomethyl ether and diethylene glycol monoethyl ether; their mixtures with water, or pure water.

When carrying out processes A) and C), the reaction temperatures can be varied within a substantial range, such as from 0 to 200° C. The processes are preferably carried out at from 10 to 150° C., in particular at from 20° C. to the boiling point of the reaction mixture in question.

In general, the starting materials are employed in approximately equimolar amounts. However, it is also possible to use an excess of each of the reactants, up to approximately twice the molar amount of the other reactant.

Processes A) and C) are expediently carried out under atmospheric pressure or under the inherent pressure of the reaction mixture in question. However, the processes may also be carried out under elevated or reduced pressure, in general at from 0.1 to 10 bar.

As a rule, the reaction mixtures in question are worked up by methods known per se, for example by diluting the reaction solution with water and subsequently isolating the product by means of filtration, crystallization or solvent extraction, or by removing the solvent, partitioning the residue in a mixture of water and a suitable organic solvent, and working up the organic phase to give the product.

As shown above the compounds of formula IV are novel compounds and suitable intermediates for the preparation of the benzoxazines of formula I according to the present invention.

Therefore the present invention also provides novel compounds of formula IV

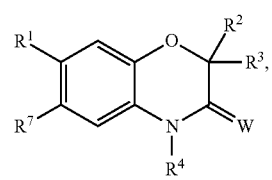

IV wherein $R^1$ is halogen;

$R^2$ is halogen;

$R^3$ is hydrogen or halogen;

$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$R^7$ is hydrogen, $NO_2$, $NH_2$, —NCO or —NH—C(O)—$NR^5$—C(Z)—$NHR^6$, wherein
R$^5$ is hydrogen, NH$_2$, C$_1$-C$_6$-alkyl or C$_3$-C$_6$-alkynyl;
R$^6$ is hydrogen or C$_1$-C$_6$-alkyl; and
Z is O or S; and
W is O or S.

With respect to the variables, the particularly preferred embodiments of the intermediate compounds IV correspond, either independently of one another or in combination with one another, to those of the variables of R$^1$, R$^2$, R$^3$, R$^4$, R$^5$, R$^6$, W and Z of formula I, or have, either independently of one another or in combination with one another, the following meanings:

R$^4$ is H or C$_3$-C$_6$-alkynyl, preferably H or CH$_2$C≡CH, more preferably H;
 is also preferably C$_3$-C$_6$-alkynyl, more preferably C$_3$-alkynyl; particularly preferred CH$_2$C≡CH.

Special preference is given to phenyl compounds of formula IV.a, which correspond to the compounds of formula IV wherein R$^7$ is H. Particular preference is given to phenyl compounds of formula IV.a, which correspond to the compounds of formula IV wherein R$^7$ is H and R$^4$ is H.

Also special preference is given to nitro compounds of formula IV.b, which correspond to the compounds of formula IV wherein R$^7$ is NO$_2$.

Also particular preference is given to nitro compounds of formula IV.b, which correspond to the compounds of formula IV wherein R$^7$ is NO$_2$ and R$^4$ is H or CH$_2$C≡CH.

Also special preference is given to amino compounds of formula IV.c, which correspond to the compounds of formula IV wherein R$^7$ is NH$_2$.

Also particular preference is given to amino compounds of formula IV.c, which correspond to the compounds of formula IV wherein R$^7$ is NH$_2$ and R$^4$ is CH$_2$C≡CH.

Also special preference is given to isocyanate compounds of formula IV.d, which correspond to the compounds of formula IV wherein R$^7$ is —NCO.

Also particular preference is given to isocyanate compounds of formula IV.d, which correspond to the compounds of formula IV wherein R$^7$ is —NCO and R$^4$ is CH$_2$C≡CH.

Also special preference is given to urea compounds of formula IV.e, which correspond to the compounds of formula IV wherein R$^7$ is —NH—C(O)—NR$^5$—C(Z)—NHR$^6$.

Also particular preference is given to urea compounds of formula IV.e, which correspond to the compounds of formula IV wherein R$^7$ is —NH—C(O)—NR$^5$—C(Z)—NHR$^6$ and R$^4$ is CH$_2$C≡CH.

As shown above the acetamides of formula V are novel compounds and suitable intermediates for the preparation of the phenyl compounds of formula IV.a, and therefore also suitable intermediates for the preparation of the benzoxazines of formula I according to the present invention.

Therefore the present invention also provides novel acetamides of formula V

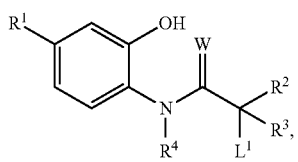

V wherein
L$^1$ is Cl, Br or I;
R$^1$ is halogen;
R$^2$ is halogen;
R$^3$ is hydrogen or halogen;
R$^4$ is hydrogen, C$_1$-C$_6$-alkyl, C$_1$-C$_6$-haloalkyl, C$_3$-C$_6$-cycloalkyl, C$_3$-C$_6$-alkenyl, C$_3$-C$_6$-haloalkenyl, C$_3$-C$_6$-alkynyl, C$_3$-C$_6$-haloalkynyl, C$_1$-C$_6$-alkoxy or C$_3$-C$_6$-cycloalkyl-C$_1$-C$_6$-alkyl; and
W is O or S.

With respect to the variables, the particularly preferred embodiments of the intermediate acetamides VI correspond, either independently of one another or in combination with one another, to those of the variables of R$^1$, R$^2$, R$^3$, R$^4$ and W of formula I, or have, either independently of one another or in combination with one another, the following meanings:
L$^1$ is Cl or Br, most preferably Cl;
 also most preferably Br;
R$^4$ is H or C$_3$-C$_6$-alkynyl, preferably H;
 is also preferably C$_3$-C$_6$-alkynyl, more preferably C$_3$-alkynyl; particularly preferred CH$_2$C≡CH.

The benzoxazinones I are suitable as herbicides. They are suitable as such or as an appropriately formulated composition (herbicidal composition) comprising as herbicide at least one benzoxazinone I, but which can optionally comprise further herbicidal compounds B and/or safeners C. The herbicidal compositions comprising the benzoxazinone of formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the benzoxazinones I or compositions comprising them can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*s. vulgare*), *Theobroma cacao, Trifolium pratense, Triticum aestivum, Triticale, Triticum durum, Vicia faba, Vitis vinifera* and *Zea mays.*

Preferred crops are the following: *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea*

*europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (s. vulgare), Triticale, Triticum aestivum, Triticum durum, Vicia faba, Vitis vinifera* and *Zea mays*.

The benzoxazinones of formula I according to the invention can also be used in genetically modified plants. The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or polypeptides e.g. by glycosylation or polymer additions such as prenylated, acetylated or farnesylated moieties or PEG moieties. Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559, 024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glypho-sate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; aggluti-nins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pretoxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the Mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The benzoxazinones of formula I according to the invention can also be used in crop plants which are resistant to one or more herbicides owing to genetic engineering or breeding, which are resistant to one or more pathogens such as plant pathogenous fungi owing to genetic engineering or breeding, or which are resistant to attack by insects owing to genetic engineering or breeding.

Suitable are for example crop plants, preferably corn, wheat, sunflower, sugarcane, cotton, rice, canola, oilseed rape or soybeans, which crops are resistant to herbicidal PPO inhibitors, or crop plants which, owing to introduction of the gene for Bt toxin by genetic modification, are resistant to attack by certain insects.

Furthermore, it has been found that the benzoxazinones of the formula I are also suitable for the defoliation and/or desiccation of plant parts, for which crop plants such as cotton, potato, oilseed rape, sunflower, soybean or field beans, in particular cotton, are suitable. In this regard, there have been found compositions for the desiccation and/or defoliation of plants, processes for preparing these compositions and methods for desiccating and/or defoliating plants using the benzoxazinones of the formula I.

As desiccants, the benzoxazinones of the formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

The benzoxazinones I, or the herbicidal compositions comprising the benzoxazinones I, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of at least one benzoxazinone of the formula I and optionally at least one further active compound selected from herbicides B and safeners C, and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhard).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers.

Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Powders, materials for broadcasting and dusts can be prepared by mixing or concomitant grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water.

To prepare emulsions, pastes or oil dispersions, the benzoxazinones of the formula I, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the active compounds, especially of the benzoxazinones of the formula I in the ready-to-use preparations (formulations) can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

In the formulation of the benzoxazinones of formula I according to the present invention the active ingredients, e.g. the benzoxazinones of formula I, are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

The benzoxazinones of formula I according to the present invention can, for example, be formulated as follows:

1. Products for Dilution with Water
A Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted
I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

The benzoxazinones of the formula I or the herbicidal compositions comprising them can be applied pre-, post-emergence or pre-plant, or together with the seed of a crop plant. It is also possible to apply the herbicidal composition or active compounds by applying seed, pretreated with the herbicidal compositions or active compounds, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the benzoxazinones of the formula I or the herbicidal compositions comprising them can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the benzoxazinones of the formula I according to the invention or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

The rates of application of the active benzoxazinone of formula I according to the present invention (total amount of benzoxazinone I) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of the benzoxazinones of formula I are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the benzoxazinones of formula I is 0.1 to 1000 g/ha, preferably 1 to 750 g/ha, more preferably 5 to 500 g/ha, of active substance.

To treat the seed, the benzoxazinones I are generally employed in amounts of from 0.001 to 10 kg per 100 kg of seed.

To broaden the spectrum of action and to achieve synergistic effects, the benzoxazinones of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

It may furthermore be beneficial to apply the benzoxazinones of the formula I alone or in combination with other herbicides, or else in the form of a mixture with other crop protection agents, for example together with agents for controlling pests or phytopathogenic fungi or bacteria.

Also of interest is the miscibility with mineral salt solutions, which are employed for treating nutritional and trace element deficiencies. Other additives such as non-phytotoxic oils and oil concentrates may also be added.

In one embodiment of the present invention the compositions according to the present invention comprise at least one benzoxazinone of formula I (compound A) and at least one further active compound selected from herbicides B, preferably herbicides B of class b1) to b15), and safeners C (compound C).

In another embodiment of the present invention the compositions according to the present invention comprise at least one benzoxazinone of formula I and at least one further active compound B (herbicide B).

The further active compound B (herbicide B) is preferably selected from the herbicides of class b1) to b15):

b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitose inhibitors;
b10) inhibitors of the synthesis of very long chain fatty acids (VLCFA inhibitors);
b11) cellulose biosynthesis inhibitors;
b12) decoupler herbicides;
b13) auxin herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Preference is given to those compositions according to the present invention comprising at least one herbicide B selected from herbicides of class b2, b3, b4, b5, b6, b9 and b10.

Specific preference is given to those compositions according to the present invention which comprise at least one herbicide B selected from the herbicides of class b4, b6, b9 and b10.

Particular preference is given to those compositions according to the present invention which comprise at least one herbicide B selected from the herbicides of class b4, b6 and b10.

According to a first embodiment of the invention the compositions contain at least one inhibitor of the lipid biosynthesis (herbicide b1). These are compounds which inhibit lipid biosynthesis. Inhibition of the lipid biosynthesis can be affected either through inhibition of acetyl CoA carboxylase (hereinafter termed ACC herbicides) or through a different mode of action (hereinafter termed non-ACC herbicides). The ACC herbicides belong to the group A of the HRAC classification system whereas the non-ACC herbicides belong to the group N of the HRAC classification.

According to a second embodiment of the invention the compositions contain at least one ALS inhibitor (herbicide b2). The herbicidal activity of these compounds is based on the inhibition of acetolactate synthase and thus on the inhibiton of the branched chain aminoacid biosynthesis. These inhibitors belong to the group B of the HRAC classification system.

According to a third embodiment of the invention the compositions contain at least one inhibitor of photosynthesis (herbicide b3). The herbicidal activity of these compounds is based either on the inhibition of the photosystem II in plants (so-called PSII inhibitors, groups C1, C2 and C3 of HRAC classification) or on diverting the electron transfer in photosystem I in plants (so-called PSI inhibitors, group D of HRAC classification) and thus on an inhibition of photosynthesis. Amongst these, PSII inhibitors are preferred.

According to a fourth embodiment of the invention the compositions contain at least one inhibitor of protoporphyrinogen-IX-oxidase (herbicide b4). The herbicidal activity of these compounds is based on the inhibition of the protoporphyrinogen-IX-oxidase. These inhibitors belong to the group E of the HRAC classification system.

According to a fifth embodiment of the invention the compositions contain at least one bleacher-herbicide (herbicide b5). The herbicidal activity of these compounds is based on the inhibition of the carotinoid biosynthesis. These include compounds which inhibit carotinoid biosynthesis by inhibition of phytoene desaturase (so-called PDS inhibitors, group F1 of HRAC classification), compounds which inhibit the 4-hydroxyphenylpyruvat-dioxygenase (HPPD inhibitors, group F2 of HRAC classification) and compounds which inhibit carotinoid biosynthesis by an unknown mode of action (bleacher—unknown target, group F3 of HRAC classification).

According to a sixth embodiment of the invention the compositions contain at least one EPSP synthase inhibitor (herbicide b6). The herbicidal activity of these compounds is based on the inhibition of enolpyruvyl shikimate 3-phosphate synthase und thus on the inhibition of the aminoacid biosynthesis in plants. These inhibitors belong to the group G of the HRAC classification system.

According to a seventh embodiment of the invention the compositions contain at least one glutamin synthetase inhibitor (herbicide b7). The herbicidal activity of these compounds is based on the inhibition of glutamin synthetase und thus on the inhibition of the aminoacid biosynthesis in plants. These inhibitors belong to the group H of the HRAC classification system.

According to an eighth embodiment of the invention the compositions contain at least one DHP synthase inhibitor (herbicide b8). The herbicidal activity of these compounds is based on the inhibition of 7,8-dihydropteroate synthetase. These inhibitors belong to the group I of the HRAC classification system.

According to a ninth embodiment of the invention the compositions contain at least one mitose inhibitor (herbicide b9). The herbicidal activity of these compounds is based on the disturbance or inhibition of microtubule formation or organization and thus on the mitosis inhibition. These inhibitors belong to the groups K1 and K2 of the HRAC classification system. Among these, compounds of the group K1, in particular dinitroanilines, are preferred.

According to a tenth embodiment of the invention the compositions contain at least one VLCFA inhibitor (herbicide b10). The herbicidal activity of these compounds is based on the inhibition of the synthesis of very long chain fatty acids and thus on the disturbance or inhibition of cell division in plants. These inhibitors belong to the group K3 of the HRAC classification system.

According to an eleventh embodiment of the invention the compositions contain at least one cellulose biosynthesis inhibitor (herbicide b11). The herbicidal activity of these compounds is based on the inhibition of the biosynthesis of cellulose and thus on the inhibition of the synthesis of cell walls in plants. These inhibitors belong to the group L of the HRAC classification system.

According to a twelfth embodiment of the invention the compositions contain at least one decoupler herbicide (herbicide b12). The herbicidal activity of these compounds is based on the disruption of the cell membrane. These inhibitors belong to the group M of the HRAC classification system.

According to a thirteenth embodiment of the invention the compositions contain at least one auxin herbicide (herbicide b13). These include compounds which act like auxins, i.e. plant hormones, and inhibit the growth of the plants. These compounds belong to the group 0 of the HRAC classification system.

According to a fourteenth embodiment of the invention the compositions contain at least one auxin transport inhibitor (herbicide b14). The herbicidal activity of these compounds is based on the inhibition of the auxin transport in plants. These compounds belong to the group P of the HRAC classification system. As to the given mechanisms of action and classification of the active substances, see e.g. "HRAC, Classification of Herbicides According to Mode of Action", http://www.plantprotection.org/hrac/MOA.html).

Examples of herbicides B which can be used in combination with the benzoxazinone compounds of the formula I according to the present invention are:
b1) from the group of the lipid biosynthesis inhibitors:
    ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxapropP-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
Sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, mesosulfuron, metazosulfuron, metsulfuron, metsulfuronmethyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuronmethyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4, 6-dimethoxy-2-pyrimidinyl)oxy]benzenemethanamine (CAS 420138-01-8) and sulfonylaminocarbonyl-triazolinone herbicides such as flucarbazone, flucarbazone-sodium, propoxycarbazon, propoxycarbazon-sodium, thiencarbazone and thiencarbazone-methyl. Among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazin, simazin, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridatre, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacetmethyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7) and 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione;

b5) from the group of the bleacher herbicides:
PDS inhibitors: beflubutamid, diflufenican, fluridone, fluorochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole, clomazone and flumeturon;

b6) from the group of the EPSP synthase inhibitors:
glyphosate, glyphosate-isopropylammonium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitose inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide and napropamide, tetrazolinones such fentrazamide, and other herbicides such as anilofos, cafenstrole, fenoxasulfone, ipfencarbazone, piperophos, pyroxasulfone and isoxazoline compounds of the formula II,

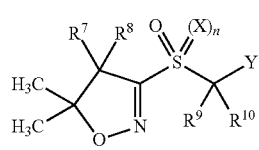

wherein $R^7$, $R^8$, $R^9$, $R^{10}$, W, Z and n have the following meanings:
$R^7$, $R^8$, $R^9$, $R^{19}$ independently of one another hydrogen, halogen or $C_1$-$C_4$-alkyl;
X oxygen or NH;
Y phenyl or monocyclic 5-, 6-, 7-, 8-, 9- or 10-membered heterocyclyl containing, in addition to carbon ring members one, two or three same or different heteroatoms selected from oxygen, nitrogen and sulfur as ring members, wherein phenyl and heterocyclyl are unsubstituted or carry 1, 2 or 3 substituents $R^{yy}$ selected from halogen, $C_1$-$C_4$-alkyl, $C_1$-$C_4$-alkoxy, $C_1$-$C_4$-haloalkyl and $C_1$-$C_4$-haloalkoxy;
preferably phenyl or 5- or 6-membered aromatic heterocyclyl (hetaryl) which contains, in addition to carbon ring members, one, two or three nitrogen atoms as ring members, wherein phenyl and hetaryl are unsubstituted or carry 1, 2 or 3 substituents $R^{yy}$; and
n zero or one;
among the isoxazoline compounds of the formula II, preference is given to isoxazoline compounds of the formula II, wherein
$R^7$, $R^8$, $R^9$, $R^{10}$ independently of one another are H, F, Cl or methyl;
X is oxygen;
n is 0 or 1; and
Y is phenyl, pyrazolyl or 1,2,3-triazolyl, wherein the three last-mentioned radicals are unsubstituted or carry one, two or three substituents $R^{yy}$, especially one of the following radicals

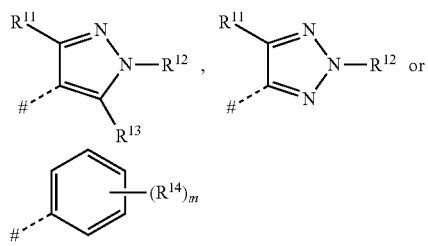

wherein
$R^{11}$ is halogen, $C_1$-$C_4$-alkyl or $C_1$-$C_4$-haloalkyl;
$R^{12}$ is $C_1$-$C_4$-alkyl;
$R^{13}$ is halogen, $C_1$-$C_4$-alkoxy or $C_1$-$C_4$-haloalkoxy;
$R^{14}$ is halogen, $C_1$-$C_4$-alkyl, $C_1$-$C_4$-haloalkyl or $C_1$-$C_4$-haloalkoxy;
m is 0, 1, 2 or 3; and
# denotes the point of attachment to the group $CR^{13}R^{14}$;
among the isoxazoline compounds of the formula II, particular preference is given to those isoxazoline compounds of the formula II, wherein
$R^7$ is hydrogen;
$R^8$ is fluorine;
$R^9$ is hydrogen or fluorine;
Ram is hydrogen or fluorine;
X is oxygen;
Y is one of the radicals of the formulae $Y^1$, $Y^2$, $Y^3$ or $Y^4$

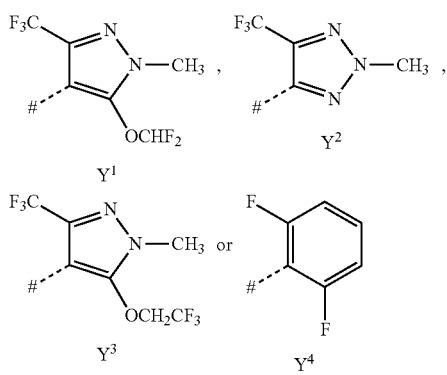

wherein # denotes the point of attachment to the group $CR^9R^{10}$;
n is zero or 1, in particular 1; and
among these, especially preferred are the isoxazoline compounds of the formulae II.1, II.2, II.3, II.4, II.5, II.6, II.7, II.8 and II.9

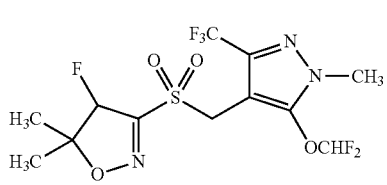

II.1

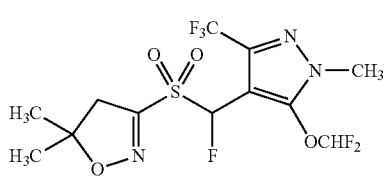

II.2

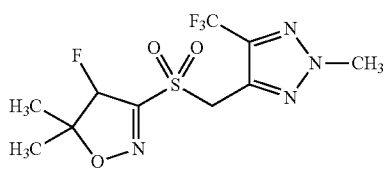

II.3

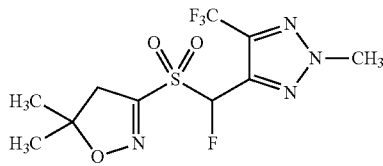

II.4

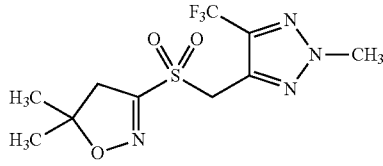

II.5

-continued

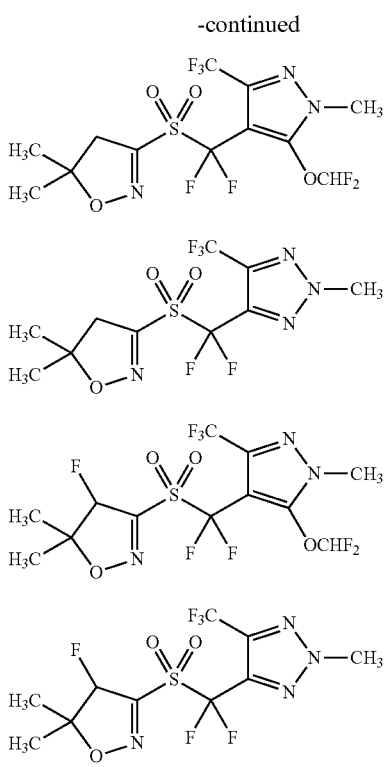

II.6

II.7

II.8

II.9 the isoxazoline compounds of the formula II are known in the art, e.g. from WO 2006/024820, WO 2006/037945, WO 2007/071900 and WO 2007/096576;

among the VLCFA inhibitors, preference is given to chloroacetamides and oxyacetamides, especially to pyroxasulfone;

b11) from the group of the cellulose biosynthesis inhibitors: chlorthiamid, dichlobenil, flupoxam, isoxaben, 1-Cyclohexyl-5-pentafluorphenyloxy-1⁴-[1,2,4,6]thiatriazin-3-ylamine and piperazine compounds of formula III,

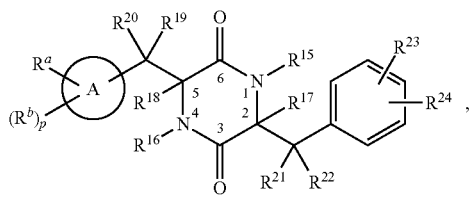

III in which

A is phenyl or pyridyl where $R^a$ is attached in the ortho-position to the point of attachment of A to a carbon atom;

$R^a$ is CN, $NO_2$, $C_1$-$C_4$-alkyl, D-$C_3$-$C_6$-cycloalkyl, $C_1$-$C_4$-haloalkyl, $C_1$-$C_4$-alkoxy, $C_1$-$C_4$-haloalkoxy, O-D-$C_3$-$C_6$-cycloalkyl, $S(O)_qR^y$, $C_2$-$C_6$-alkenyl, D-$C_3$-$C_6$-cycloalkenyl, $C_3$-$C_6$-alkenyloxy, $C_2$-$C_6$-alkynyl, $C_3$-$C_6$-alkynyloxy, $NR^AR^B$, tri-$C_1$-$C_4$-alkylsilyl, D-C(=O)—$R^{a1}$, DP(=O)($R^{a1}$)$_2$, phenyl, naphthyl, a 3- to 7-membered monocyclic or 9- or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups $R^{aa}$ and/or Rat, and, if $R^a$ is attached to a carbon atom, additionally halogen;

$R^y$ is $C_1$-$C_6$-alkyl, $C_3$-$C_4$-alkenyl, $C_3$-$C_4$-alkynyl, $NR^AR^B$ or $C_1$-$C_4$-haloalkyl and q is 0, 1 or 2;

$R^A$, $R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$, $R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond, $C_1$-$C_4$-alkylene, $C_2$-$C_6$-alkenyl or $C_2$-$C_6$-alkynyl;

$R^{a1}$ is hydrogen, OH, $C_1$-$C_8$-Alkyl, $C_1$-$C_4$-haloalkyl, $C_3$-$C_6$-cycloalkyl, $C_2$-$C_8$-alkenyl, $C_5$-$C_6$-cycloalkenyl, $C_2$-$C_8$-alkynyl, $C_1$-$C_6$-alkoxy, $C_1$-$C_4$-haloalkoxy, $C_3$-$C_8$-alkenyloxy, $C_3$-$C_8$-alkynyloxy, $NR^AR^B$, $C_1$-$C_6$-alkoxyamino, $C_1$-$C_6$-alkylsulfonylamino, $C_1$-$C_6$-alkylaminosulfonylamino, [di($C_1$-$C_6$)alkylamino]sulfonylamino, $C_3$-$C_6$-alkenylamino, $C_3$-$C_6$-alkynylamino, N—($C_2$-$C_6$-alkenyl)-N—($C_1$-$C_6$-alkyl)amino, N—($C_2$-$C_6$-alkynyl)-N—($C_1$-$C_6$-alkyl)amino, N—($C_1$-$C_6$-alkoxy)-N—($C_1$-$C_6$-alkyl) amino, N—($C_2$-$C_6$-alkenyl)-N—($C_1$-$C_6$-alkoxy) amino, N—($C_2$-$C_6$-alkynyl)-N—($C_1$-$C_6$-alkoxy)-amino, $C_1$-$C_6$-alkylsulfonyl, tri-$C_1$-$C_4$-alkylsilyl, phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^{aa}$;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_qR^y$, D-C(=O)—$R^{a1}$ and tri-$C_1$-$C_4$-alkylsilyl;

Rb independently of one another are hydrogen, CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_qR^y$, $R^b$ together with the group $R^a$ or Rb attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0, 1, 2 or 3;

$R^{15}$ is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, $NR^AR^B$, $S(O)_nR^y$, $S(O)_nNR^AR^B$, $C(=O)R^{25}$, $CONR^AR^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups: $C_1$-$C_4$-alkyl, $C_3$-$C_4$-alkenyl, $C_3$-$C_4$-alkynyl, $C_1$-$C_4$-alkoxy, $C_3$-$C_6$-cycloalkyl, $C_5$-$C_6$-cycloalkenyl, $NR^AR^B$, $S(O)_nR^y$, $S(O)_nNR^AR^B$, $C(=O)R^{25}$, $CONR^AR^B$; preferably is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, $NR^AR^B$, $S(O)_nR^y$, $S(O)_nNR^AR^B$, $C(=O)R^{25}$, $CONR^AR^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups: $C_1$-$C_4$-alkyl, $C_3$-$C_4$-alkenyl and $C_3$-$C_4$-alkynyl;

$R^{25}$ is hydrogen, $C_1$-$C_4$-alkyl, $C_1$-$C_4$-haloalkyl, $C_1$-$C_4$-alkoxy or $C_1$-$C_4$-haloalkoxy;

$D^1$ is carbonyl or a group D;

where in groups $R^{15}$, $R^a$ and their sub-substituents the carbon chains and/or the cyclic groups may carry 1, 2, 3 or 4 substituents $R^{aa}$ and/or $R^{a1}$;

$R^{16}$ is $C_1$-$C_4$-alkyl, $C_3$-$C_4$-alkenyl or $C_3$-$C_4$-alkynyl;

$R^{17}$ is OH, $NH_2$, $C_1$-$C_4$-alkyl, $C_3$-$C_6$-cycloalkyl, $C_3$-$C_6$-alkenyl, $C_3$-$C_6$-alkynyl, $C_1$-$C_4$-hydroxyalkyl, $C_1$-$C_4$-cyanoalkyl, $C_1$-$C_4$-haloalkyl, $C_1$-$C_4$-alkoxy-$C_1$-$C_4$-alkyl or $C(=O)R^{25}$;

$R^{18}$ is hydrogen, halogen, $C_1$-$C_4$-alkyl or $C_1$-$C_4$-haloalkyl, or $R^{18}$ and $R^{19}$ together are a covalent bond;

$R^{19}$, $R^{20}$, $R^{21}$, $R^{21}$ independently of one another are hydrogen, halogen, OH, CN, $NO_2$, $C_1$-$C_4$-alkyl, $C_1$-$C_4$-haloalkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-cycloalkyl, $C_3$-$C_6$-cycloalkenyl and $C_3$-$C_6$-cycloalkynyl;

$R^{23}$, $R^{24}$ independently of one another are hydrogen, halogen, OH, haloalkyl, $NR^A R^B$, $NR^A C(O)R^{26}$, CN, $NO_2$, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, O—C(O)$R^{26}$, phenoxy or benzyloxy, where in groups $R^{23}$ and $R^{24}$ the carbon chains and/or the cyclic groups may carry 1, 2, 3 or 4 substituents $R^{aa}$;

$R^{26}$ is $C_1$-$C_4$-alkyl or $NR^A R^B$;

among the isoxazoline compounds of the piperazin compounds of formula III, preference is given to the piperazine compounds of the formula III, wherein A is phenyl or pyridyl where $R^a$ is attached in the ortho-position to the point of attachment of A to a carbon atom;

$R^a$ is CN, $NO_2$, $C_1$-$C_4$-alkyl, $C_1$-$C_4$-haloalkyl, $C_1$-$C_4$-alkoxy, $C_1$-$C_4$-haloalkoxy or D-C(=O)—$R^{a1}$;

$R^y$ is $C_1$-$C_6$-alkyl, $C_3$-$C_4$-alkenyl, $C_3$-$C_4$-alkynyl, $NR^A R^B$ or $C_1$-$C_4$-haloalkyl and q is 0, 1 or 2;

$R^A$, $R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$, $R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond or $C_1$-$C_4$-alkylene;

$R^{a1}$ is hydrogen, OH, $C_1$-$C_8$-Alkyl, $C_1$-$C_4$-haloalkyl, $C_3$-$C_6$-cycloalkyl;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_q R^y$, D-C(=O)—$R^{a1}$ and tri-$C_1$-$C_4$-alkylsilyl;

$R^b$ independently of one another is CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_q R^y$;

$R^b$ together with the group $R^a$ or Rb attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0 or 1;

$R^{15}$ is hydrogen, $C_1$-$C_{12}$-alkyl, $C_3$-$C_{12}$-alkenyl, $C_3$-$C_{12}$-alkynyl, $C_1$-$C_4$-alkoxy or $C(=O)R^{25}$, which can be partially or fully substituted by $R^{aa}$-groups;

preferably is hydrogen, $C_1$-$C_{12}$-alkyl, $C_3$-$C_{12}$-alkenyl, $C_3$-$C_{12}$-alkynyl, $C_1$-$C_4$-alkoxy or $C(=O)R^{25}$;

$R^{25}$ is hydrogen, $C_1$-$C_4$-alkyl, $C_1$-$C_4$-haloalkyl, $C_1$-$C_4$-alkoxy or $C_1$-$C_4$-haloalkoxy;

where in groups $R^{15}$, $R^a$ and their sub-substituents the carbon chains and/or the cyclic groups may carry 1, 2, 3 or 4 substituents $R^{aa}$ and/or $R^{a1}$;

$R^{16}$ is $C_1$-$C_4$-alkyl;

$R^{17}$ is OH, $NH_2$, $C_1$-$C_4$-alkyl, $C_3$-$C_6$-cycloalkyl, $C_1$-$C_4$-haloalkyl or $C(=O)R^{25}$;

$R^{18}$ is hydrogen, or $R^{18}$ and $R^{19}$ together are a covalent bond;

$R^{19}$, $R^{20}$, $R^{21}$, $R^{21}$ independently of one another are hydrogen;

$R^{23}$, $R^{24}$ independently of one another are hydrogen, halogen or OH;

b12) from the group of the decoupler herbicides:
dinoseb, dinoterb and DNOC and its salts;

b13) from the group of the auxin herbicides:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluoroxypyr, fluroxypyr-butomethyl, fluoroxypyr-meptyl, MCPA and its salts and esters, MCPA-thioethyl, MCPB and its salts and esters, mecopropand its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Preferred herbicides B which can be used in combination with the benzoxazinones of the formula I according to the present invention are:

b1) from the group of the lipid biosynthesis inhibitors:
clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, benfuresate, dimepiperate, EPTC, esprocarb, ethofumesate, molinate, orbencarb, prosulfocarb, thiobencarb and triallate;

b2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, mesosulfuron, metazosulfuron, metosulam, metsulfuronmethyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl and tritosulfuron;

b3) from the group of the photosynthesis inhibitors:
ametryn, amicarbazone, atrazine, bentazon, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors:
acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen-ethyl, saflufenacil, sulfentrazone, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7) and 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione;

b5) from the group of the bleacher herbicides:
aclonifen, beflubutamid, benzobicyclon, clomazone, diflufenican, fluorochloridone, flurtamone, isoxaflutole, mesotrione, norflurazon, picolinafen, pyrasulfotole, pyrazolynate, sulcotrione, tefuryltrione, tembotrione, topramezone, bicyclopyrone, 4-(3-trifluoromethylphenoxy)-2-(4-trifluoromethylphenyl)pyrimidine (CAS 180608-33-7), amitrole and flumeturon;

b6) from the group of the EPSP synthase inhibitors:
glyphosate, glyphosate-isopropylammonium and glyphosate-trimesium (sulfosate);

b7) from the group of the glutamine synthase inhibitors:
glufosinate, glufosinate-P, glufosinate-ammonium;

b8) from the group of the DHP synthase inhibitors: asulam;

b9) from the group of the mitose inhibitors:
benfluralin, dithiopyr, ethalfluralin, oryzalin, pendimethalin, thiazopyr and trifluralin;

b10) from the group of the VLCFA inhibitors:
acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors:
dichlobenil, flupoxam, isoxaben, 1-Cyclohexyl-5-pentafluorphenyloxy-1$^4$-[1,2,4,6]thiatriazin-3-ylamine and the piperazine compounds of formula III as mentioned above;

b13) from the group of the auxin herbicides:
2,4-D and its salts and esters, aminopyralid and its salts such as aminopyralid-tris(2-hydroxypropyl)ammonium and its esters, clopyralid and its salts and esters, dicamba and its salts and esters, dichlorprop-P and its salts and esters, fluoroxypyrmeptyl, MCPA and its salts and esters, MCPB and its salts and esters, mecoprop-P and its salts and esters, picloram and its salts and esters, quinclorac, quinmerac, triclopyr and its salts and esters, and aminocyclopyrachlor and its salts and esters;

b14) from the group of the auxin transport inhibitors:
diflufenzopyr and diflufenzopyr-sodium;

b15) from the group of the other herbicides: bromobutide, cinmethylin, cumyluron, dalapon, difenzoquat, difenzoquat-metilsulfate, DSMA, dymron (=daimuron), flamprop, flamprop-isopropyl, flamprop-methyl, flamprop-M-isopropyl, flamprop-M-methyl, indanofan, indaziflam, metam, methylbromide, MSMA, oxaziclomefone, pyributicarb, triaziflam, tridiphane and 6-chloro-3-(2-cyclopropyl-6-methylphenoxy)-4-pyridazinol (CAS 499223-49-3) and its salts and esters.

Particularly preferred herbicides B which can be used in combination with the benzoxazinones of the formula I according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: flumioxazin, oxyfluorfen, saflufenacil, sulfentrazone, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100) and 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione;

b5) from the group of the bleacher herbicides: clomazone, diflufenican, fluorochloridone, isoxaflutole, mesotrione, picolinafen, sulcotrione, tefuryltrione, tembotrione, topramezone, bicyclopyrone, amitrole and flumeturon;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitose inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: isoxaben and the piperazine compounds of formula III as mentioned above;

b13) from the group of the auxin herbicides: 2,4-D and its salts and esters, aminopyralid and its salts and its esters, clopyralid and its salts and esters, dicamba and its salts and esters, fluoroxypyr-meptyl, quinclorac, quinmerac and aminocyclopyrachlor and its salts and esters;

b14) from the group of the auxin transport inhibitors: diflufenzopyr and diflufenzopyr-sodium, b15) from the group of the other herbicides: dymron (=daimuron), indanofan, indaziflam, oxaziclomefone and triaziflam.

Moreover, it may be useful to apply the benzoxazinones of the formula I in combination with safeners. Safeners are chemical compounds which prevent or reduce damage on useful plants without having a major impact on the herbicidal action of the benzoxazinones of the formula I towards unwanted plants. They can be applied either before sowings (e.g. on seed treatments, shoots or seedlings) or in the pre-emergence application or post-emergence application of the useful plant. The safeners and the benzoxazinones of the formula I can be applied simultaneously or in succession.

Furthermore, the safeners C, the benzoxazinones I and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C are benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660. Further herbicidally active compounds are known from WO 96/26202, WO 97/41116, WO 97/41117, WO 97/41118 and WO 01/83459 and also from W. Krämer et al. (ed.) "Modern Crop Protection Compounds", Vol. 1, Wiley VCH, 2007 and the literature cited therein.

The assignment of the active compounds to the respective mechanisms of action is based on current knowledge. If several mechanisms of action apply to one active compound, this substance was only assigned to one mechanism of action.

If the herbicides B and/or the safener C are capable of forming geometrical isomers, for example E/Z isomers, both the pure isomers and mixtures thereof may be used in the compositions according to the invention. If the herbicides B and/or the safener C have one or more centers of chirality and are thus present as enantiomers or diastereomers, both the pure enantiomers and diastereomers and mixtures thereof may be used in the compositions according to the invention.

If the herbicides B and/or the safener C have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyeth-1-oxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium, such as trimethylsulfonium, and sulfoxonium ions, preferably tri ($C_1$-$C_4$-alkyl)sulfoxonium.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Active compounds B and C having a carboxyl group can be employed in the form of the acid, in the form of an agriculturally suitable salt or else in the form of an agriculturally acceptable derivative in the compositions according to the invention, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the methoxyethyl, ethoxyethyl or butoxyethyl ester. An example of a straight-chain or branched $C_1$-$C_{10}$-alkylthio ester is the ethylthio ester.

According to a preferred embodiment of the invention, the composition comprises as herbicidal active compound B or component B, at least one, preferably exactly one herbicide B.

According to another preferred embodiment of the invention, the composition comprises as herbicidal active compound B or component B, at least two, preferably exactly two herbicides B different from each other.

According to another preferred embodiment of the invention, the composition comprises as herbicidal active compound B or component B, at least three, preferably exactly three herbicides B different from each other.

According to another preferred embodiment of the invention, the composition comprises as safening component C at least one, preferably exactly one safener C.

According to another preferred embodiment of the invention, the composition comprises as component B, at least one, preferably exactly one herbicide B, and at least one, preferably exactly one, safener C.

According to another preferred embodiment of the invention, the composition comprises as component B, preferably exactly two herbicides B different from each other, and at lest one, preferably exactly one, safener C.

According to another preferred embodiment of the invention, the composition comprises as component B, at least three, preferably exactly three herbicides B different from each other, and at lest one, preferably exactly one, safener C.

According to another preferred embodiment of the invention, the composition comprises as component A at least one, preferably exactly one, benzoxazinone compound of formula I, preferably of formula I.a, and as component B, at least one, preferably exactly one, herbicide B.

According to another preferred embodiment of the invention, the composition comprises as component A at least one, preferably exactly one, benzoxazinone compound of formula I, preferably of formula I.a, and as component B, at least two, preferably exactly two, herbicides B different from each other.

According to another preferred embodiment of the invention, the composition comprises as component A at least one, preferably exactly one, benzoxazinone compound of formula I, preferably of formula I.a, and as component B, at least three, preferably exactly three herbicides, B different from each other.

According to another preferred embodiment of the invention, the composition comprises as active components at least one, preferably exactly one, benzoxazinone compound of formula I, preferably of formula I.a, and at least one, preferably exactly one, herbicide B.

According to another preferred embodiment of the invention, the composition comprises as active components at least one, preferably exactly one, benzoxazinone compound of formula I, preferably of formula I.a, and at least two, preferably exactly two, herbicides B different from each other.

According to another preferred embodiment of the invention, the composition comprises as active components at least one, preferably exactly one, benzoxazinone of formula I, preferably of formula I.a, and at least three, preferably exactly three, herbicides B different from each other.

According to another preferred embodiment of the invention, the composition comprises as active components at least one, preferably exactly one, benzoxazinone of formula I, preferably of formula I.a, and at least one, preferably exactly one, safener C.

According to another preferred embodiment of the invention, the composition comprises as active components at least one, preferably exactly one, benzoxazinone of formula I, preferably of formula I.a, at least one, preferably exactly one, herbicide B, and at least one, preferably exactly one safener C.

According to another preferred embodiment of the invention, the composition comprises as active components at least one, preferably exactly one, benzoxazinone of formula I, preferably of formula I.a, at least two, preferably exactly two herbicides B different from each other, and at least one, preferably exactly one, safener C.

According to another preferred embodiment of the invention, the composition comprises as active components at least one, preferably exactly one, benzoxazinone of formula I, preferably of formula I.a, at least three, preferably exactly three herbicides B different from each other, and at least one, preferably exactly one, safener C.

A first preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b1), in particular selected from the group consisting of clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate.

A second preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b2), in particular selected from the group consisting of bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron.

A third preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b3), in particular selected from the group consisting of ametryn, atrazine, diuron, fluometuron, hexazinone, isoproturon, linuron, metribuzin, paraquat, paraquat-dichloride, propanil, terbutryn and terbuthylazine.

A fourth preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b4), in particular selected from the group consisting of flumioxazin, oxyfluorfen, saflufenacil, sulfentrazone, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100) and 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione.

A fifth preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b5), in particular selected from the group consisting of clomazone, diflufenican, fluorochloridone, isoxaflutole, mesotrione, picolinafen, sulcotrione, tefuryltrione, tembotrione, topramezone, bicyclopyrone, amitrole and flumeturon.

A sixth preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b6), in particular selected from the group consisting of glyphosate, glyphosate-isopropylammonium and glyphosate-trimesium (sulfosate).

A seventh preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b7), in particular selected from the group consisting of glufosinate, glufosinate-P and glufosinate-ammonium.

An eighth preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b9), in particular selected from the group consisting of pendimethalin and trifluralin.

A ninth preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a benzoxazinone of the formula I, preferably of formula I.a, especially an active compound from the group consisting of I.a.35, at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

A tenth preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b11), in particular isoxaben. Likewise, preference is given to compositions comprising in addition to a benzoxazinone of the formula I, preferably of formula I.a, especially an active compound from the group consisting of I.a.35, at least one and especially exactly one herbicidally active compound from group b10), in particular selected from the group consisting of piperazine compounds of formula III as defined above.

An eleventh preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b13), in particular selected from the group consisting of 2,4-D and its salts and esters, aminopyralid and its salts such as aminopyralid-tris(2-hydroxypropyl)ammonium and its esters, clopyralid and its salts and esters, dicamba and its salts and esters, fluoroxypyrmeptyl, quinclorac, quinmerac and aminocyclopyrachlor and its salts and esters.

A twelfth preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b14), in particular selected from the group consisting of diflufenzopyr and diflufenzopyr-sodium.

A 13th preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from group b15), in particular selected from the group consisting of dymron (=daimuron), indanofan, indaziflam, oxaziclomefone and triaziflam.

A 14th preferred embodiment of the invention relates to compositions according to the invention comprising, in addition to a benzoxazinone of the formula I, preferably of formula I.a, especially an active compound from the group consisting of I.a.35, at least one and especially exactly one herbicidally active compound from the safeners C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Further preferred embodiments relate to ternary compositions which correspond to the binary compositions of embodiments 1 to 14 and additionally comprise a safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, for example 1, 2 or 3, active compounds of the formula I and either one or more, for example 1, 2 or 3, herbicides B or one or more safeners.

Correspondingly, the term "ternary compositions" includes compositions comprising one or more, for example 1, 2 or 3, active compounds of the formula I, one or more, for example 1, 2 or 3, herbicides B and one or more, for example 1, 2 or 3, safeners C.

In binary compositions comprising at least one compound of the formula I as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula I as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one benzoxazinone compound of the formula I as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

Particularly preferred herbicides B are the herbicides B as defined above; in particular the herbicides B.1-B.141 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-P-ethyl |
| B.6 | metamifop |
| B.7 | pinoxaden |
| B.8 | profoxydim |
| B.9 | sethoxydim |
| B.10 | tepraloxydim |
| B.11 | tralkoxydim |
| B.12 | esprocarb |
| B.13 | ethofumesate |
| B.14 | molinate |
| B.15 | prosulfocarb |
| B.16 | thiobencarb |
| B.17 | triallate |
| B.18 | bensulfuron-methyl |
| B.19 | bispyribac-sodium |
| B.20 | cloransulam |
| B.21 | chlorsulfuron |
| B.22 | clorimuron |
| B.23 | cyclosulfamuron |
| B.24 | diclosulam |
| B.25 | florasulam |

TABLE B-continued

| | Herbicide B |
|---|---|
| B.26 | flumetsulam |
| B.27 | flupyrsulfuron-methyl-sodium |
| B.28 | foramsulfuron |
| B.29 | imazamox |
| B.30 | imazapic |
| B.31 | imazapyr |
| B.32 | imazaquin |
| B.33 | imazethapyr |
| B.34 | imazosulfuron |
| B.35 | iodosulfuron-methyl-sodium |
| B.36 | mesosulfuron |
| B.37 | metazosulfuron |
| B.38 | metsulfuron |
| B.39 | metosulam |
| B.40 | nicosulfuron |
| B.41 | penoxsulam |
| B.42 | propoxycarbazon-sodium |
| B.43 | pyrazosulfuron-ethyl |
| B.44 | pyribenzoxim |
| B.45 | pyriftalid |
| B.46 | pyroxsulam |
| B.47 | rimsulfuron |
| B.48 | sulfosulfuron |
| B.49 | thiencarbazone-methyl |
| B.50 | thifensulfuron |
| B.51 | tribenuron |
| B.52 | tritosulfuron |
| B.53 | ametryne |
| B.54 | atrazine |
| B.55 | bentazon |
| B.56 | bromoxynil |
| B.57 | diuron |
| B.58 | fluometuron |
| B.59 | hexazinone |
| B.60 | isoproturon |
| B.61 | linuron |
| B.62 | metamitron |
| B.63 | metribuzin |
| B.64 | propanil |
| B.65 | simazin |
| B.66 | terbuthylazine |
| B.67 | terbutryn |
| B.68 | paraquat-dichloride |
| B.69 | acifluorfen |
| B.70 | butafenacil |
| B.71 | carfentrazone-ethyl |
| B.72 | flumioxazin |
| B.73 | fomesafen |
| B.74 | oxadiargyl |
| B.75 | oxyfluorfen |
| B.76 | saflufenacil |
| B.77 | sulfentrazone |
| B.78 | ethyl [3-[2-chloro-4-fluoro-5-(1-methyl-6-trifluoromethyl-2,4-dioxo-1,2,3,4-tetrahydro-pyrimidin-3-yl)phenoxy]-2-pyridyloxy]acetate (CAS 353292-31-6) |
| B.79 | 3-[7-fluoro-3-oxo-4-(prop-2-yn-yl)-3,4-dihydro-2H-benzo[1,4]-oxazin-6-yl]-1,5-dimethyl-6-thi-oxo-[1,3,5]triazinan-2,4-dione |
| B.80 | benzobicyclon |
| B.81 | clomazone |
| B.82 | diflufenican |
| B.83 | flurochloridone |
| B.84 | isoxaflutole |
| B.85 | mesotrione |
| B.86 | norflurazone |
| B.87 | picolinafen |
| B.88 | sulcotrione |
| B.89 | tefuryltrione |
| B.90 | tembotrione |
| B.91 | topramezone |
| B.92 | bicyclopyrone |
| B.93 | amitrole |
| B.94 | fluometuron |

TABLE B-continued

| | Herbicide B |
|---|---|
| B.95 | glyphosate |
| B.96 | glyphosate-isopropylammonium |
| B.97 | glyphosate-trimesium (sulfosate) |
| B.98 | glufosinate |
| B.99 | glufosinate-P |
| B.100 | glufosinate-ammonium |
| B.101 | pendimethalin |
| B.102 | trifluralin |
| B.103 | acetochlor |
| B.104 | butachlor |
| B.105 | cafenstrole |
| B.106 | dimethenamid-P |
| B.107 | fentrazamide |
| B.108 | flufenacet |
| B.109 | mefenacet |
| B.110 | metazachlor |
| B.111 | metolachlor |
| B.112 | S-metolachlor |
| B.113 | pretilachlor |
| B.114 | fenoxasulfone |
| B.115 | isoxaben |
| B.116 | pyroxasulfone |
| B.117 | 2,4-D |
| B.118 | aminopyralid |
| B.119 | clopyralid |
| B.120 | dicamba |
| B.121 | fluroxypyr-meptyl |
| B.122 | MCPA |
| B.123 | quinclorac |
| B.124 | quinmerac |
| B.125 | aminocyclopyrachlor |
| B.126 | diflufenzopyr |
| B.127 | diflufenzopyr-sodium |
| B.128 | dymron |
| B.129 | indanofan |
| B.130 | indaziflam |
| B.131 | oxaziclomefone |
| B.132 | triaziflam |
| B.133 | II.1 |
| B.134 | II.2 |
| B.135 | II.3 |
| B.136 | II.4 |
| B.137 | II.5 |
| B.138 | II.6 |
| B.139 | II.7 |
| B.140 | II.8 |
| B.141 | II.9 |

Particularly preferred safeners C, which, as component C, are constituent of the composition according to the invention are the safeners C as defined above; in particular the safeners C.1-C.12, especially C. 1-C.11 listed below in table C:

TABLE C

| | Safener C |
|---|---|
| C.1 | benoxacor |
| C.2 | cloquintocet |
| C.3 | cyprosulfamide |
| C.4 | dichlormid |
| C.5 | fenclorim |
| C.6 | fenchlorazole |
| C.7 | furilazole |
| C.8 | isoxadifen |
| C.9 | mefenpyr |
| C.10 | 4-(dichloroacetyl)-1-oxa-4-azaspiro[4.5]decane (MON4660, CAS 71526-07-3) |
| C.11 | 2,2,5-trimethyl-3-(dichloroacetyl)-1,3-oxazolidine (R-29148, CAS 52836-31-4) |
| C.12 | naphtalic acid anhydride |

The weight ratios of the individual components in the preferred mixtures mentioned below are within the limits given above, in particular within the preferred limits.

Particularly preferred are the compositions mentioned below,
comprising the benzoxazinone compound as defined and the substance(s) as defined in the respective row of table 1;
especially preferred comprising as only herbicidal active compounds the benzoxazinone compound as defined and the substance(s) as defined in the respective row of table 1;
most preferably comprising as only active compounds the benzoxazinone compound as defined and the substance(s) as defined in the respective row of table 1.

Particularly preferred are compositions 1.1 to 1.1833, especially 1.1 to 1.1692, comprising the benzoxazinone I.a.35 and the substance(s) as defined in the respective row of table 1:

TABLE 1

(compositions 1.1 to 1.1833):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |

TABLE 1-continued (compositions 1.1 to 1.1833):

| comp. no. | herbicide B | safener C |
|---|---|---|
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | |
| 1.140 | B.140 | — |
| 1.141 | B.141 | — |
| 1.142 | B.1 | C.1 |
| 1.143 | B.2 | C.1 |
| 1.144 | B.3 | C.1 |
| 1.145 | B.4 | C.1 |
| 1.146 | B.5 | C.1 |
| 1.147 | B.6 | C.1 |
| 1.148 | B.7 | C.1 |
| 1.149 | B.8 | C.1 |
| 1.150 | B.9 | C.1 |
| 1.151 | B.10 | C.1 |
| 1.152 | B.11 | C.1 |
| 1.153 | B.12 | C.1 |
| 1.154 | B.13 | C.1 |
| 1.155 | B.14 | C.1 |
| 1.156 | B.15 | C.1 |
| 1.157 | B.16 | C.1 |
| 1.158 | B.17 | C.1 |
| 1.159 | B.18 | C.1 |
| 1.160 | B.19 | C.1 |
| 1.161 | B.20 | C.1 |
| 1.162 | B.21 | C.1 |
| 1.163 | B.22 | C.1 |
| 1.164 | B.23 | C.1 |
| 1.165 | B.24 | C.1 |
| 1.166 | B.25 | C.1 |
| 1.167 | B.26 | C.1 |
| 1.168 | B.27 | C.1 |
| 1.169 | B.28 | C.1 |
| 1.170 | B.29 | C.1 |
| 1.171 | B.30 | C.1 |
| 1.172 | B.31 | C.1 |
| 1.173 | B.32 | C.1 |
| 1.174 | B.33 | C.1 |
| 1.175 | B.34 | C.1 |
| 1.176 | B.35 | C.1 |
| 1.177 | B.36 | C.1 |
| 1.178 | B.37 | C.1 |
| 1.179 | B.38 | C.1 |
| 1.180 | B.39 | C.1 |
| 1.181 | B.40 | C.1 |
| 1.182 | B.41 | C.1 |
| 1.183 | B.42 | C.1 |
| 1.184 | B.43 | C.1 |
| 1.185 | B.44 | C.1 |
| 1.186 | B.45 | C.1 |
| 1.187 | B.46 | C.1 |
| 1.188 | B.47 | C.1 |
| 1.189 | B.48 | C.1 |
| 1.190 | B.49 | C.1 |
| 1.191 | B.50 | C.1 |
| 1.192 | B.51 | C.1 |
| 1.193 | B.52 | C.1 |
| 1.194 | B.53 | C.1 |
| 1.195 | B.54 | C.1 |
| 1.196 | B.55 | C.1 |
| 1.197 | B.56 | C.1 |
| 1.198 | B.57 | C.1 |
| 1.199 | B.58. | C.1 |
| 1.200 | B.59 | C.1 |
| 1.201 | B.60 | C.1 |
| 1.202 | B.61 | C.1 |

TABLE 1-continued (compositions 1.1 to 1.1833):

| comp. no. | herbicide B | safener C |
|---|---|---|
| 1.203 | B.62 | C.1 |
| 1.204 | B.63 | C.1 |
| 1.205 | B.64 | C.1 |
| 1.206 | B.65 | C.1 |
| 1.207 | B.66 | C.1 |
| 1.208 | B.67 | C.1 |
| 1.209 | B.68 | C.1 |
| 1.210 | B.69 | C.1 |
| 1.211 | B.70 | C.1 |
| 1.212 | B.71 | C.1 |
| 1.213 | B.72 | C.1 |
| 1.214 | B.73 | C.1 |
| 1.215 | B.74 | C.1 |
| 1.216 | B.75 | C.1 |
| 1.217 | B.76 | C.1 |
| 1.218 | B.77 | C.1 |
| 1.219 | B.78 | C.1 |
| 1.220 | B.79 | C.1 |
| 1.221 | B.80 | C.1 |
| 1.222 | B.81 | C.1 |
| 1.223 | B.82 | C.1 |
| 1.224 | B.83 | C.1 |
| 1.225 | B.84 | C.1 |
| 1.226 | B.85 | C.1 |
| 1.227 | B.86 | C.1 |
| 1.228 | B.87 | C.1 |
| 1.229 | B.88 | C.1 |
| 1.230 | B.89 | C.1 |
| 1.231 | B.90 | C.1 |
| 1.232 | B.91 | C.1 |
| 1.233 | B.92 | C.1 |
| 1.234 | B.93 | C.1 |
| 1.235 | B.94 | C.1 |
| 1.236 | B.95 | C.1 |
| 1.237 | B.96 | C.1 |
| 1.238 | B.97 | C.1 |
| 1.239 | B.98 | C.1 |
| 1.240 | B.99 | C.1 |
| 1.241 | B.100 | C.1 |
| 1.242 | B.101 | C.1 |
| 1.243 | B.102 | C.1 |
| 1.244 | B.103 | C.1 |
| 1.245 | B.104 | C.1 |
| 1.246 | B.105 | C.1 |
| 1.247 | B.106 | C.1 |
| 1.248 | B.107 | C.1 |
| 1.249 | B.108 | C.1 |
| 1.250 | B.109 | C.1 |
| 1.251 | B.110 | C.1 |
| 1.252 | B.111 | C.1 |
| 1.253 | B.112 | C.1 |
| 1.254 | B.113 | C.1 |
| 1.255 | B.114 | C.1 |
| 1.256 | B.115 | C.1 |
| 1.257 | B.116 | C.1 |
| 1.258 | B.117 | C.1 |
| 1.259 | B.118 | C.1 |
| 1.260 | B.119 | C.1 |
| 1.261 | B.120 | C.1 |
| 1.262 | B.121 | C.1 |
| 1.263 | B.122 | C.1 |
| 1.264 | B.123 | C.1 |
| 1.265 | B.124 | C.1 |
| 1.266 | B.125 | C.1 |
| 1.267 | B.126 | C.1 |
| 1.268 | B.127 | C.1 |
| 1.269 | B.128 | C.1 |
| 1.270 | B.129 | C.1 |
| 1.271 | B.130 | C.1 |
| 1.272 | B.131 | C.1 |
| 1.273 | B.132 | C.1 |
| 1.274 | B.133 | C.1 |
| 1.275 | B.134 | C.1 |
| 1.276 | B.135 | C.1 |
| 1.277 | B.136 | C.1 |
| 1.278 | B.137 | C.1 |
| 1.279 | B.138 | C.1 |
| 1.280 | B.139 | C.1 |
| 1.281 | B.140 | C.1 |
| 1.282 | B.141 | C.1 |
| 1.283 | B.1 | C.2 |
| 1.284 | B.2 | C.2 |
| 1.285 | B.3 | C.2 |
| 1.286 | B.4 | C.2 |
| 1.287 | B.5 | C.2 |
| 1.288 | B.6 | C.2 |
| 1.289 | B.7 | C.2 |
| 1.290 | B.8 | C.2 |
| 1.291 | B.9 | C.2 |
| 1.292 | B.10 | C.2 |
| 1.293 | B.11 | C.2 |
| 1.294 | B.12 | C.2 |
| 1.295 | B.13 | C.2 |
| 1.296 | B.14 | C.2 |
| 1.297 | B.15 | C.2 |
| 1.298 | B.16 | C.2 |
| 1.299 | B.17 | C.2 |
| 1.300 | B.18 | C.2 |
| 1.301 | B.19 | C.2 |
| 1.302 | B.20 | C.2 |
| 1.303 | B.21 | C.2 |
| 1.304 | B.22 | C.2 |
| 1.305 | B.23 | C.2 |
| 1.306 | B.24 | C.2 |
| 1.307 | B.25 | C.2 |
| 1.308 | B.26 | C.2 |
| 1.309 | B.27 | C.2 |
| 1.310 | B.28 | C.2 |
| 1.311 | B.29 | C.2 |
| 1.312 | B.30 | C.2 |
| 1.313 | B.31 | C.2 |
| 1.314 | B.32 | C.2 |
| 1.315 | B.33 | C.2 |
| 1.316 | B.34 | C.2 |
| 1.317 | B.35 | C.2 |
| 1.318 | B.36 | C.2 |
| 1.319 | B.37 | C.2 |
| 1.320 | B.38 | C.2 |
| 1.321 | B.39 | C.2 |
| 1.322 | B.40 | C.2 |
| 1.323 | B.41 | C.2 |
| 1.324 | B.42 | C.2 |
| 1.325 | B.43 | C.2 |
| 1.326 | B.44 | C.2 |
| 1.327 | B.45 | C.2 |
| 1.328 | B.46 | C.2 |
| 1.329 | B.47 | C.2 |
| 1.330 | B.48 | C.2 |
| 1.331 | B.49 | C.2 |
| 1.332 | B.50 | C.2 |
| 1.333 | B.51 | C.2 |
| 1.334 | B.52 | C.2 |
| 1.335 | B.53 | C.2 |
| 1.336 | B.54 | C.2 |
| 1.337 | B.55 | C.2 |
| 1.338 | B.56 | C.2 |
| 1.339 | B.57 | C.2 |
| 1.340 | B.58. | C.2 |
| 1.341 | B.59 | C.2 |
| 1.342 | B.60 | C.2 |
| 1.343 | B.61 | C.2 |
| 1.344 | B.62 | C.2 |
| 1.345 | B.63 | C.2 |
| 1.346 | B.64 | C.2 |
| 1.347 | B.65 | C.2 |
| 1.348 | B.66 | C.2 |
| 1.349 | B.67 | C.2 |
| 1.350 | B.68 | C.2 |
| 1.351 | B.69 | C.2 |
| 1.352 | B.70 | C.2 |

TABLE 1-continued (compositions 1.1 to 1.1833):

| comp. no. | herbicide B | safener C |
|---|---|---|
| 1.353 | B.71 | C.2 |
| 1.354 | B.72 | C.2 |
| 1.355 | B.73 | C.2 |
| 1.356 | B.74 | C.2 |
| 1.357 | B.75 | C.2 |
| 1.358 | B.76 | C.2 |
| 1.359 | B.77 | C.2 |
| 1.360 | B.78 | C.2 |
| 1.361 | B.79 | C.2 |
| 1.362 | B.80 | C.2 |
| 1.363 | B.81 | C.2 |
| 1.364 | B.82 | C.2 |
| 1.365 | B.83 | C.2 |
| 1.366 | B.84 | C.2 |
| 1.367 | B.85 | C.2 |
| 1.368 | B.86 | C.2 |
| 1.369 | B.87 | C.2 |
| 1.370 | B.88 | C.2 |
| 1.371 | B.89 | C.2 |
| 1.372 | B.90 | C.2 |
| 1.373 | B.91 | C.2 |
| 1.374 | B.92 | C.2 |
| 1.375 | B.93 | C.2 |
| 1.376 | B.94 | C.2 |
| 1.377 | B.95 | C.2 |
| 1.378 | B.96 | C.2 |
| 1.379 | B.97 | C.2 |
| 1.380 | B.98 | C.2 |
| 1.381 | B.99 | C.2 |
| 1.382 | B.100 | C.2 |
| 1.383 | B.101 | C.2 |
| 1.384 | B.102 | C.2 |
| 1.385 | B.103 | C.2 |
| 1.386 | B.104 | C.2 |
| 1.387 | B.105 | C.2 |
| 1.388 | B.106 | C.2 |
| 1.389 | B.107 | C.2 |
| 1.390 | B.108 | C.2 |
| 1.391 | B.109 | C.2 |
| 1.392 | B.110 | C.2 |
| 1.393 | B.111 | C.2 |
| 1.394 | B.112 | C.2 |
| 1.395 | B.113 | C.2 |
| 1.396 | B.114 | C.2 |
| 1.397 | B.115 | C.2 |
| 1.398 | B.116 | C.2 |
| 1.399 | B.117 | C.2 |
| 1.400 | B.118 | C.2 |
| 1.401 | B.119 | C.2 |
| 1.402 | B.120 | C.2 |
| 1.403 | B.121 | C.2 |
| 1.404 | B.122 | C.2 |
| 1.405 | B.123 | C.2 |
| 1.406 | B.124 | C.2 |
| 1.407 | B.125 | C.2 |
| 1.408 | B.126 | C.2 |
| 1.409 | B.127 | C.2 |
| 1.410 | B.128 | C.2 |
| 1.411 | B.129 | C.2 |
| 1.412 | B.130 | C.2 |
| 1.413 | B.131 | C.2 |
| 1.414 | B.132 | C.2 |
| 1.415 | B.133 | C.2 |
| 1.416 | B.134 | C.2 |
| 1.417 | B.135 | C.2 |
| 1.418 | B.136 | C.2 |
| 1.419 | B.137 | C.2 |
| 1.420 | B.138 | C.2 |
| 1.421 | B.139 | C.2 |
| 1.422 | B.140 | C.2 |
| 1.423 | B.141 | C.2 |
| 1.424 | B.1 | C.3 |
| 1.425 | B.2 | C.3 |
| 1.426 | B.3 | C.3 |
| 1.427 | B.4 | C.3 |
| 1.428 | B.5 | C.3 |
| 1.429 | B.6 | C.3 |
| 1.430 | B.7 | C.3 |
| 1.431 | B.8 | C.3 |
| 1.432 | B.9 | C.3 |
| 1.433 | B.10 | C.3 |
| 1.434 | B.11 | C.3 |
| 1.435 | B.12 | C.3 |
| 1.436 | B.13 | C.3 |
| 1.437 | B.14 | C.3 |
| 1.438 | B.15 | C.3 |
| 1.439 | B.16 | C.3 |
| 1.440 | B.17 | C.3 |
| 1.441 | B.18 | C.3 |
| 1.442 | B.19 | C.3 |
| 1.443 | B.20 | C.3 |
| 1.444 | B.21 | C.3 |
| 1.445 | B.22 | C.3 |
| 1.446 | B.23 | C.3 |
| 1.447 | B.24 | C.3 |
| 1.448 | B.25 | C.3 |
| 1.449 | B.26 | C.3 |
| 1.450 | B.27 | C.3 |
| 1.451 | B.28 | C.3 |
| 1.452 | B.29 | C.3 |
| 1.453 | B.30 | C.3 |
| 1.454 | B.31 | C.3 |
| 1.455 | B.32 | C.3 |
| 1.456 | B.33 | C.3 |
| 1.457 | B.34 | C.3 |
| 1.458 | B.35 | C.3 |
| 1.459 | B.36 | C.3 |
| 1.460 | B.37 | C.3 |
| 1.461 | B.38 | C.3 |
| 1.462 | B.39 | C.3 |
| 1.463 | B.40 | C.3 |
| 1.464 | B.41 | C.3 |
| 1.465 | B.42 | C.3 |
| 1.466 | B.43 | C.3 |
| 1.467 | B.44 | C.3 |
| 1.468 | B.45 | C.3 |
| 1.469 | B.46 | C.3 |
| 1.470 | B.47 | C.3 |
| 1.471 | B.48 | C.3 |
| 1.472 | B.49 | C.3 |
| 1.473 | B.50 | C.3 |
| 1.474 | B.51 | C.3 |
| 1.475 | B.52 | C.3 |
| 1.476 | B.53 | C.3 |
| 1.477 | B.54 | C.3 |
| 1.478 | B.55 | C.3 |
| 1.479 | B.56 | C.3 |
| 1.480 | B.57 | C.3 |
| 1.481 | B.58. | C.3 |
| 1.482 | B.59 | C.3 |
| 1.483 | B.60 | C.3 |
| 1.484 | B.61 | C.3 |
| 1.485 | B.62 | C.3 |
| 1.486 | B.63 | C.3 |
| 1.487 | B.64 | C.3 |
| 1.488 | B.65 | C.3 |
| 1.489 | B.66 | C.3 |
| 1.490 | B.67 | C.3 |
| 1.491 | B.68 | C.3 |
| 1.492 | B.69 | C.3 |
| 1.493 | B.70 | C.3 |
| 1.494 | B.71 | C.3 |
| 1.495 | B.72 | C.3 |
| 1.496 | B.73 | C.3 |
| 1.497 | B.74 | C.3 |
| 1.498 | B.75 | C.3 |
| 1.499 | B.76 | C.3 |
| 1.500 | B.77 | C.3 |
| 1.501 | B.78 | C.3 |
| 1.502 | B.79 | C.3 |

TABLE 1-continued (compositions 1.1 to 1.1833):

| comp. no. | herbicide B | safener C |
|---|---|---|
| 1.503 | B.80 | C.3 |
| 1.504 | B.81 | C.3 |
| 1.505 | B.82 | C.3 |
| 1.506 | B.83 | C.3 |
| 1.507 | B.84 | C.3 |
| 1.508 | B.85 | C.3 |
| 1.509 | B.86 | C.3 |
| 1.510 | B.87 | C.3 |
| 1.511 | B.88 | C.3 |
| 1.512 | B.89 | C.3 |
| 1.513 | B.90 | C.3 |
| 1.514 | B.91 | C.3 |
| 1.515 | B.92 | C.3 |
| 1.516 | B.93 | C.3 |
| 1.517 | B.94 | C.3 |
| 1.518 | B.95 | C.3 |
| 1.519 | B.96 | C.3 |
| 1.520 | B.97 | C.3 |
| 1.521 | B.98 | C.3 |
| 1.522 | B.99 | C.3 |
| 1.523 | B.100 | C.3 |
| 1.524 | B.101 | C.3 |
| 1.525 | B.102 | C.3 |
| 1.526 | B.103 | C.3 |
| 1.527 | B.104 | C.3 |
| 1.528 | B.105 | C.3 |
| 1.529 | B.106 | C.3 |
| 1.530 | B.107 | C.3 |
| 1.531 | B.108 | C.3 |
| 1.532 | B.109 | C.3 |
| 1.533 | B.110 | C.3 |
| 1.534 | B.111 | C.3 |
| 1.535 | B.112 | C.3 |
| 1.536 | B.113 | C.3 |
| 1.537 | B.114 | C.3 |
| 1.538 | B.115 | C.3 |
| 1.539 | B.116 | C.3 |
| 1.540 | B.117 | C.3 |
| 1.541 | B.118 | C.3 |
| 1.542 | B.119 | C.3 |
| 1.543 | B.120 | C.3 |
| 1.544 | B.121 | C.3 |
| 1.545 | B.122 | C.3 |
| 1.546 | B.123 | C.3 |
| 1.547 | B.124 | C.3 |
| 1.548 | B.125 | C.3 |
| 1.549 | B.126 | C.3 |
| 1.550 | B.127 | C.3 |
| 1.551 | B.128 | C.3 |
| 1.552 | B.129 | C.3 |
| 1.553 | B.130 | C.3 |
| 1.554 | B.131 | C.3 |
| 1.555 | B.132 | C.3 |
| 1.556 | B.133 | C.3 |
| 1.557 | B.134 | C.3 |
| 1.558 | B.135 | C.3 |
| 1.559 | B.136 | C.3 |
| 1.560 | B.137 | C.3 |
| 1.561 | B.138 | C.3 |
| 1.562 | B.139 | C.3 |
| 1.563 | B.140 | C.3 |
| 1.564 | B.141 | C.3 |
| 1.565 | B.1 | C.4 |
| 1.566 | B.2 | C.4 |
| 1.567 | B.3 | C.4 |
| 1.568 | B.4 | C.4 |
| 1.569 | B.5 | C.4 |
| 1.570 | B.6 | C.4 |
| 1.571 | B.7 | C.4 |
| 1.572 | B.8 | C.4 |
| 1.573 | B.9 | C.4 |
| 1.574 | B.10 | C.4 |
| 1.575 | B.11 | C.4 |
| 1.576 | B.12 | C.4 |
| 1.577 | B.13 | C.4 |
| 1.578 | B.14 | C.4 |
| 1.579 | B.15 | C.4 |
| 1.580 | B.16 | C.4 |
| 1.581 | B.17 | C.4 |
| 1.582 | B.18 | C.4 |
| 1.583 | B.19 | C.4 |
| 1.584 | B.20 | C.4 |
| 1.585 | B.21 | C.4 |
| 1.586 | B.22 | C.4 |
| 1.587 | B.23 | C.4 |
| 1.588 | B.24 | C.4 |
| 1.589 | B.25 | C.4 |
| 1.590 | B.26 | C.4 |
| 1.591 | B.27 | C.4 |
| 1.592 | B.28 | C.4 |
| 1.593 | B.29 | C.4 |
| 1.594 | B.30 | C.4 |
| 1.595 | B.31 | C.4 |
| 1.596 | B.32 | C.4 |
| 1.597 | B.33 | C.4 |
| 1.598 | B.34 | C.4 |
| 1.599 | B.35 | C.4 |
| 1.600 | B.36 | C.4 |
| 1.601 | B.37 | C.4 |
| 1.602 | B.38 | C.4 |
| 1.603 | B.39 | C.4 |
| 1.604 | B.40 | C.4 |
| 1.605 | B.41 | C.4 |
| 1.606 | B.42 | C.4 |
| 1.607 | B.43 | C.4 |
| 1.608 | B.44 | C.4 |
| 1.609 | B.45 | C.4 |
| 1.610 | B.46 | C.4 |
| 1.611 | B.47 | C.4 |
| 1.612 | B.48 | C.4 |
| 1.613 | B.49 | C.4 |
| 1.614 | B.50 | C.4 |
| 1.615 | B.51 | C.4 |
| 1.616 | B.52 | C.4 |
| 1.617 | B.53 | C.4 |
| 1.618 | B.54 | C.4 |
| 1.619 | B.55 | C.4 |
| 1.620 | B.56 | C.4 |
| 1.621 | B.57 | C.4 |
| 1.622 | B.58. | C.4 |
| 1.623 | B.59 | C.4 |
| 1.624 | B.60 | C.4 |
| 1.625 | B.61 | C.4 |
| 1.626 | B.62 | C.4 |
| 1.627 | B.63 | C.4 |
| 1.628 | B.64 | C.4 |
| 1.629 | B.65 | C.4 |
| 1.630 | B.66 | C.4 |
| 1.631 | B.67 | C.4 |
| 1.632 | B.68 | C.4 |
| 1.633 | B.69 | C.4 |
| 1.634 | B.70 | C.4 |
| 1.635 | B.71 | C.4 |
| 1.636 | B.72 | C.4 |
| 1.637 | B.73 | C.4 |
| 1.638 | B.74 | C.4 |
| 1.639 | B.75 | C.4 |
| 1.640 | B.76 | C.4 |
| 1.641 | B.77 | C.4 |
| 1.642 | B.78 | C.4 |
| 1.643 | B.79 | C.4 |
| 1.644 | B.80 | C.4 |
| 1.645 | B.81 | C.4 |
| 1.646 | B.82 | C.4 |
| 1.647 | B.83 | C.4 |
| 1.648 | B.84 | C.4 |
| 1.649 | B.85 | C.4 |
| 1.650 | B.86 | C.4 |
| 1.651 | B.87 | C.4 |
| 1.652 | B.88 | C.4 |

TABLE 1-continued (compositions 1.1 to 1.1833):

| comp. no. | herbicide B | safener C |
|---|---|---|
| 1.653 | B.89 | C.4 |
| 1.654 | B.90 | C.4 |
| 1.655 | B.91 | C.4 |
| 1.656 | B.92 | C.4 |
| 1.657 | B.93 | C.4 |
| 1.658 | B.94 | C.4 |
| 1.659 | B.95 | C.4 |
| 1.660 | B.96 | C.4 |
| 1.661 | B.97 | C.4 |
| 1.662 | B.98 | C.4 |
| 1.663 | B.99 | C.4 |
| 1.664 | B.100 | C.4 |
| 1.665 | B.101 | C.4 |
| 1.666 | B.102 | C.4 |
| 1.667 | B.103 | C.4 |
| 1.668 | B.104 | C.4 |
| 1.669 | B.105 | C.4 |
| 1.670 | B.106 | C.4 |
| 1.671 | B.107 | C.4 |
| 1.672 | B.108 | C.4 |
| 1.673 | B.109 | C.4 |
| 1.674 | B.110 | C.4 |
| 1.675 | B.111 | C.4 |
| 1.676 | B.112 | C.4 |
| 1.677 | B.113 | C.4 |
| 1.678 | B.114 | C.4 |
| 1.679 | B.115 | C.4 |
| 1.680 | B.116 | C.4 |
| 1.681 | B.117 | C.4 |
| 1.682 | B.118 | C.4 |
| 1.683 | B.119 | C.4 |
| 1.684 | B.120 | C.4 |
| 1.685 | B.121 | C.4 |
| 1.686 | B.122 | C.4 |
| 1.687 | B.123 | C.4 |
| 1.688 | B.124 | C.4 |
| 1.689 | B.125 | C.4 |
| 1.690 | B.126 | C.4 |
| 1.691 | B.127 | C.4 |
| 1.692 | B.128 | C.4 |
| 1.693 | B.129 | C.4 |
| 1.694 | B.130 | C.4 |
| 1.695 | B.131 | C.4 |
| 1.696 | B.132 | C.4 |
| 1.697 | B.133 | C.4 |
| 1.698 | B.134 | C.4 |
| 1.699 | B.135 | C.4 |
| 1.700 | B.136 | C.4 |
| 1.701 | B.137 | C.4 |
| 1.702 | B.138 | C.4 |
| 1.703 | B.139 | C.4 |
| 1.704 | B.140 | C.4 |
| 1.705 | B.141 | C.4 |
| 1.706 | B.1 | C.5 |
| 1.707 | B.2 | C.5 |
| 1.708 | B.3 | C.5 |
| 1.709 | B.4 | C.5 |
| 1.710 | B.5 | C.5 |
| 1.711 | B.6 | C.5 |
| 1.712 | B.7 | C.5 |
| 1.713 | B.8 | C.5 |
| 1.714 | B.9 | C.5 |
| 1.715 | B.10 | C.5 |
| 1.716 | B.11 | C.5 |
| 1.717 | B.12 | C.5 |
| 1.718 | B.13 | C.5 |
| 1.719 | B.14 | C.5 |
| 1.720 | B.15 | C.5 |
| 1.721 | B.16 | C.5 |
| 1.722 | B.17 | C.5 |
| 1.723 | B.18 | C.5 |
| 1.724 | B.19 | C.5 |
| 1.725 | B.20 | C.5 |
| 1.726 | B.21 | C.5 |
| 1.727 | B.22 | C.5 |
| 1.728 | B.23 | C.5 |
| 1.729 | B.24 | C.5 |
| 1.730 | B.25 | C.5 |
| 1.731 | B.26 | C.5 |
| 1.732 | B.27 | C.5 |
| 1.733 | B.28 | C.5 |
| 1.734 | B.29 | C.5 |
| 1.735 | B.30 | C.5 |
| 1.736 | B.31 | C.5 |
| 1.737 | B.32 | C.5 |
| 1.738 | B.33 | C.5 |
| 1.739 | B.34 | C.5 |
| 1.740 | B.35 | C.5 |
| 1.741 | B.36 | C.5 |
| 1.742 | B.37 | C.5 |
| 1.743 | B.38 | C.5 |
| 1.744 | B.39 | C.5 |
| 1.745 | B.40 | C.5 |
| 1.746 | B.41 | C.5 |
| 1.747 | B.42 | C.5 |
| 1.748 | B.43 | C.5 |
| 1.749 | B.44 | C.5 |
| 1.750 | B.45 | C.5 |
| 1.751 | B.46 | C.5 |
| 1.752 | B.47 | C.5 |
| 1.753 | B.48 | C.5 |
| 1.754 | B.49 | C.5 |
| 1.755 | B.50 | C.5 |
| 1.756 | B.51 | C.5 |
| 1.757 | B.52 | C.5 |
| 1.758 | B.53 | C.5 |
| 1.759 | B.54 | C.5 |
| 1.760 | B.55 | C.5 |
| 1.761 | B.56 | C.5 |
| 1.762 | B.57 | C.5 |
| 1.763 | B.58. | C.5 |
| 1.764 | B.59 | C.5 |
| 1.765 | B.60 | C.5 |
| 1.766 | B.61 | C.5 |
| 1.767 | B.62 | C.5 |
| 1.768 | B.63 | C.5 |
| 1.769 | B.64 | C.5 |
| 1.770 | B.65 | C.5 |
| 1.771 | B.66 | C.5 |
| 1.772 | B.67 | C.5 |
| 1.773 | B.68 | C.5 |
| 1.774 | B.69 | C.5 |
| 1.775 | B.70 | C.5 |
| 1.776 | B.71 | C.5 |
| 1.777 | B.72 | C.5 |
| 1.778 | B.73 | C.5 |
| 1.779 | B.74 | C.5 |
| 1.780 | B.75 | C.5 |
| 1.781 | B.76 | C.5 |
| 1.782 | B.77 | C.5 |
| 1.783 | B.78 | C.5 |
| 1.784 | B.79 | C.5 |
| 1.785 | B.80 | C.5 |
| 1.786 | B.81 | C.5 |
| 1.787 | B.82 | C.5 |
| 1.788 | B.83 | C.5 |
| 1.789 | B.84 | C.5 |
| 1.790 | B.85 | C.5 |
| 1.791 | B.86 | C.5 |
| 1.792 | B.87 | C.5 |
| 1.793 | B.88 | C.5 |
| 1.794 | B.89 | C.5 |
| 1.795 | B.90 | C.5 |
| 1.796 | B.91 | C.5 |
| 1.797 | B.92 | C.5 |
| 1.798 | B.93 | C.5 |
| 1.799 | B.94 | C.5 |
| 1.800 | B.95 | C.5 |
| 1.801 | B.96 | C.5 |
| 1.802 | B.97 | C.5 |

TABLE 1-continued (compositions 1.1 to 1.1833):

| comp. no. | herbicide B | safener C |
|---|---|---|
| 1.803 | B.98 | C.5 |
| 1.804 | B.99 | C.5 |
| 1.805 | B.100 | C.5 |
| 1.806 | B.101 | C.5 |
| 1.807 | B.102 | C.5 |
| 1.808 | B.103 | C.5 |
| 1.809 | B.104 | C.5 |
| 1.810 | B.105 | C.5 |
| 1.811 | B.106 | C.5 |
| 1.812 | B.107 | C.5 |
| 1.813 | B.108 | C.5 |
| 1.814 | B.109 | C.5 |
| 1.815 | B.110 | C.5 |
| 1.816 | B.111 | C.5 |
| 1.817 | B.112 | C.5 |
| 1.818 | B.113 | C.5 |
| 1.819 | B.114 | C.5 |
| 1.820 | B.115 | C.5 |
| 1.821 | B.116 | C.5 |
| 1.822 | B.117 | C.5 |
| 1.823 | B.118 | C.5 |
| 1.824 | B.119 | C.5 |
| 1.825 | B.120 | C.5 |
| 1.826 | B.121 | C.5 |
| 1.827 | B.122 | C.5 |
| 1.828 | B.123 | C.5 |
| 1.829 | B.124 | C.5 |
| 1.830 | B.125 | C.5 |
| 1.831 | B.126 | C.5 |
| 1.832 | B.127 | C.5 |
| 1.833 | B.128 | C.5 |
| 1.834 | B.129 | C.5 |
| 1.835 | B.130 | C.5 |
| 1.836 | B.131 | C.5 |
| 1.837 | B.132 | C.5 |
| 1.838 | B.133 | C.5 |
| 1.839 | B.134 | C.5 |
| 1.840 | B.135 | C.5 |
| 1.841 | B.136 | C.5 |
| 1.842 | B.137 | C.5 |
| 1.843 | B.138 | C.5 |
| 1.844 | B.139 | C.5 |
| 1.845 | B.140 | C.5 |
| 1.846 | B.141 | C.5 |
| 1.847 | B.1 | C.6 |
| 1.848 | B.2 | C.6 |
| 1.849 | B.3 | C.6 |
| 1.850 | B.4 | C.6 |
| 1.851 | B.5 | C.6 |
| 1.852 | B.6 | C.6 |
| 1.853 | B.7 | C.6 |
| 1.854 | B.8 | C.6 |
| 1.855 | B.9 | C.6 |
| 1.856 | B.10 | C.6 |
| 1.857 | B.11 | C.6 |
| 1.858 | B.12 | C.6 |
| 1.859 | B.13 | C.6 |
| 1.860 | B.14 | C.6 |
| 1.861 | B.15 | C.6 |
| 1.862 | B.16 | C.6 |
| 1.863 | B.17 | C.6 |
| 1.864 | B.18 | C.6 |
| 1.865 | B.19 | C.6 |
| 1.866 | B.20 | C.6 |
| 1.867 | B.21 | C.6 |
| 1.868 | B.22 | C.6 |
| 1.869 | B.23 | C.6 |
| 1.870 | B.24 | C.6 |
| 1.871 | B.25 | C.6 |
| 1.872 | B.26 | C.6 |
| 1.873 | B.27 | C.6 |
| 1.874 | B.28 | C.6 |
| 1.875 | B.29 | C.6 |
| 1.876 | B.30 | C.6 |
| 1.877 | B.31 | C.6 |
| 1.878 | B.32 | C.6 |
| 1.879 | B.33 | C.6 |
| 1.880 | B.34 | C.6 |
| 1.881 | B.35 | C.6 |
| 1.882 | B.36 | C.6 |
| 1.883 | B.37 | C.6 |
| 1.884 | B.38 | C.6 |
| 1.885 | B.39 | C.6 |
| 1.886 | B.40 | C.6 |
| 1.887 | B.41 | C.6 |
| 1.888 | B.42 | C.6 |
| 1.889 | B.43 | C.6 |
| 1.890 | B.44 | C.6 |
| 1.891 | B.45 | C.6 |
| 1.892 | B.46 | C.6 |
| 1.893 | B.47 | C.6 |
| 1.894 | B.48 | C.6 |
| 1.895 | B.49 | C.6 |
| 1.896 | B.50 | C.6 |
| 1.897 | B.51 | C.6 |
| 1.898 | B.52 | C.6 |
| 1.899 | B.53 | C.6 |
| 1.900 | B.54 | C.6 |
| 1.901 | B.55 | C.6 |
| 1.902 | B.56 | C.6 |
| 1.903 | B.57 | C.6 |
| 1.904 | B.58. | C.6 |
| 1.905 | B.59 | C.6 |
| 1.906 | B.60 | C.6 |
| 1.907 | B.61 | C.6 |
| 1.908 | B.62 | C.6 |
| 1.909 | B.63 | C.6 |
| 1.910 | B.64 | C.6 |
| 1.911 | B.65 | C.6 |
| 1.912 | B.66 | C.6 |
| 1.913 | B.67 | C.6 |
| 1.914 | B.68 | C.6 |
| 1.915 | B.69 | C.6 |
| 1.916 | B.70 | C.6 |
| 1.917 | B.71 | C.6 |
| 1.918 | B.72 | C.6 |
| 1.919 | B.73 | C.6 |
| 1.920 | B.74 | C.6 |
| 1.921 | B.75 | C.6 |
| 1.922 | B.76 | C.6 |
| 1.923 | B.77 | C.6 |
| 1.924 | B.78 | C.6 |
| 1.925 | B.79 | C.6 |
| 1.926 | B.80 | C.6 |
| 1.927 | B.81 | C.6 |
| 1.928 | B.82 | C.6 |
| 1.929 | B.83 | C.6 |
| 1.930 | B.84 | C.6 |
| 1.931 | B.85 | C.6 |
| 1.932 | B.86 | C.6 |
| 1.933 | B.87 | C.6 |
| 1.934 | B.88 | C.6 |
| 1.935 | B.89 | C.6 |
| 1.936 | B.90 | C.6 |
| 1.937 | B.91 | C.6 |
| 1.938 | B.92 | C.6 |
| 1.939 | B.93 | C.6 |
| 1.940 | B.94 | C.6 |
| 1.941 | B.95 | C.6 |
| 1.942 | B.96 | C.6 |
| 1.943 | B.97 | C.6 |
| 1.944 | B.98 | C.6 |
| 1.945 | B.99 | C.6 |
| 1.946 | B.100 | C.6 |
| 1.947 | B.101 | C.6 |
| 1.948 | B.102 | C.6 |
| 1.949 | B.103 | C.6 |
| 1.950 | B.104 | C.6 |
| 1.951 | B.105 | C.6 |
| 1.952 | B.106 | C.6 |

TABLE 1-continued (compositions 1.1 to 1.1833):

| comp. no. | herbicide B | safener C |
|---|---|---|
| 1.953 | B.107 | C.6 |
| 1.954 | B.108 | C.6 |
| 1.955 | B.109 | C.6 |
| 1.956 | B.110 | C.6 |
| 1.957 | B.111 | C.6 |
| 1.958 | B.112 | C.6 |
| 1.959 | B.113 | C.6 |
| 1.960 | B.114 | C.6 |
| 1.961 | B.115 | C.6 |
| 1.962 | B.116 | C.6 |
| 1.963 | B.117 | C.6 |
| 1.964 | B.118 | C.6 |
| 1.965 | B.119 | C.6 |
| 1.966 | B.120 | C.6 |
| 1.967 | B.121 | C.6 |
| 1.968 | B.122 | C.6 |
| 1.969 | B.123 | C.6 |
| 1.970 | B.124 | C.6 |
| 1.971 | B.125 | C.6 |
| 1.972 | B.126 | C.6 |
| 1.973 | B.127 | C.6 |
| 1.974 | B.128 | C.6 |
| 1.975 | B.129 | C.6 |
| 1.976 | B.130 | C.6 |
| 1.977 | B.131 | C.6 |
| 1.978 | B.132 | C.6 |
| 1.979 | B.133 | C.6 |
| 1.980 | B.134 | C.6 |
| 1.981 | B.135 | C.6 |
| 1.982 | B.136 | C.6 |
| 1.983 | B.137 | C.6 |
| 1.984 | B.138 | C.6 |
| 1.985 | B.139 | C.6 |
| 1.986 | B.140 | C.6 |
| 1.987 | B.141 | C.6 |
| 1.988 | B.1 | C.7 |
| 1.989 | B.2 | C.7 |
| 1.990 | B.3 | C.7 |
| 1.991 | B.4 | C.7 |
| 1.992 | B.5 | C.7 |
| 1.993 | B.6 | C.7 |
| 1.994 | B.7 | C.7 |
| 1.995 | B.8 | C.7 |
| 1.996 | B.9 | C.7 |
| 1.997 | B.10 | C.7 |
| 1.998 | B.11 | C.7 |
| 1.999 | B.12 | C.7 |
| 1.1000 | B.13 | C.7 |
| 1.1001 | B.14 | C.7 |
| 1.1002 | B.15 | C.7 |
| 1.1003 | B.16 | C.7 |
| 1.1004 | B.17 | C.7 |
| 1.1005 | B.18 | C.7 |
| 1.1006 | B.19 | C.7 |
| 1.1007 | B.20 | C.7 |
| 1.1008 | B.21 | C.7 |
| 1.1009 | B.22 | C.7 |
| 1.1010 | B.23 | C.7 |
| 1.1011 | B.24 | C.7 |
| 1.1012 | B.25 | C.7 |
| 1.1013 | B.26 | C.7 |
| 1.1014 | B.27 | C.7 |
| 1.1015 | B.28 | C.7 |
| 1.1016 | B.29 | C.7 |
| 1.1017 | B.30 | C.7 |
| 1.1018 | B.31 | C.7 |
| 1.1019 | B.32 | C.7 |
| 1.1020 | B.33 | C.7 |
| 1.1021 | B.34 | C.7 |
| 1.1022 | B.35 | C.7 |
| 1.1023 | B.36 | C.7 |
| 1.1024 | B.37 | C.7 |
| 1.1025 | B.38 | C.7 |
| 1.1026 | B.39 | C.7 |
| 1.1027 | B.40 | C.7 |
| 1.1028 | B.41 | C.7 |
| 1.1029 | B.42 | C.7 |
| 1.1030 | B.43 | C.7 |
| 1.1031 | B.44 | C.7 |
| 1.1032 | B.45 | C.7 |
| 1.1033 | B.46 | C.7 |
| 1.1034 | B.47 | C.7 |
| 1.1035 | B.48 | C.7 |
| 1.1036 | B.49 | C.7 |
| 1.1037 | B.50 | C.7 |
| 1.1038 | B.51 | C.7 |
| 1.1039 | B.52 | C.7 |
| 1.1040 | B.53 | C.7 |
| 1.1041 | B.54 | C.7 |
| 1.1042 | B.55 | C.7 |
| 1.1043 | B.56 | C.7 |
| 1.1044 | B.57 | C.7 |
| 1.1045 | B.58. | C.7 |
| 1.1046 | B.59 | C.7 |
| 1.1047 | B.60 | C.7 |
| 1.1048 | B.61 | C.7 |
| 1.1049 | B.62 | C.7 |
| 1.1050 | B.63 | C.7 |
| 1.1051 | B.64 | C.7 |
| 1.1052 | B.65 | C.7 |
| 1.1053 | B.66 | C.7 |
| 1.1054 | B.67 | C.7 |
| 1.1055 | B.68 | C.7 |
| 1.1056 | B.69 | C.7 |
| 1.1057 | B.70 | C.7 |
| 1.1058 | B.71 | C.7 |
| 1.1059 | B.72 | C.7 |
| 1.1060 | B.73 | C.7 |
| 1.1061 | B.74 | C.7 |
| 1.1062 | B.75 | C.7 |
| 1.1063 | B.76 | C.7 |
| 1.1064 | B.77 | C.7 |
| 1.1065 | B.78 | C.7 |
| 1.1066 | B.79 | C.7 |
| 1.1067 | B.80 | C.7 |
| 1.1068 | B.81 | C.7 |
| 1.1069 | B.82 | C.7 |
| 1.1070 | B.83 | C.7 |
| 1.1071 | B.84 | C.7 |
| 1.1072 | B.85 | C.7 |
| 1.1073 | B.86 | C.7 |
| 1.1074 | B.87 | C.7 |
| 1.1075 | B.88 | C.7 |
| 1.1076 | B.89 | C.7 |
| 1.1077 | B.90 | C.7 |
| 1.1078 | B.91 | C.7 |
| 1.1079 | B.92 | C.7 |
| 1.1080 | B.93 | C.7 |
| 1.1081 | B.94 | C.7 |
| 1.1082 | B.95 | C.7 |
| 1.1083 | B.96 | C.7 |
| 1.1084 | B.97 | C.7 |
| 1.1085 | B.98 | C.7 |
| 1.1086 | B.99 | C.7 |
| 1.1087 | B.100 | C.7 |
| 1.1088 | B.101 | C.7 |
| 1.1089 | B.102 | C.7 |
| 1.1090 | B.103 | C.7 |
| 1.1091 | B.104 | C.7 |
| 1.1092 | B.105 | C.7 |
| 1.1093 | B.106 | C.7 |
| 1.1094 | B.107 | C.7 |
| 1.1095 | B.108 | C.7 |
| 1.1096 | B.109 | C.7 |
| 1.1097 | B.110 | C.7 |
| 1.1098 | B.111 | C.7 |
| 1.1099 | B.112 | C.7 |
| 1.1100 | B.113 | C.7 |
| 1.1101 | B.114 | C.7 |
| 1.1102 | B.115 | C.7 |

TABLE 1-continued (compositions 1.1 to 1.1833):

| comp. no. | herbicide B | safener C |
|---|---|---|
| 1.1103 | B.116 | C.7 |
| 1.1104 | B.117 | C.7 |
| 1.1105 | B.118 | C.7 |
| 1.1106 | B.119 | C.7 |
| 1.1107 | B.120 | C.7 |
| 1.1108 | B.121 | C.7 |
| 1.1109 | B.122 | C.7 |
| 1.1110 | B.123 | C.7 |
| 1.1111 | B.124 | C.7 |
| 1.1112 | B.125 | C.7 |
| 1.1113 | B.126 | C.7 |
| 1.1114 | B.127 | C.7 |
| 1.1115 | B.128 | C.7 |
| 1.1116 | B.129 | C.7 |
| 1.1117 | B.130 | C.7 |
| 1.1118 | B.131 | C.7 |
| 1.1119 | B.132 | C.7 |
| 1.1120 | B.133 | C.7 |
| 1.1121 | B.134 | C.7 |
| 1.1122 | B.135 | C.7 |
| 1.1123 | B.136 | C.7 |
| 1.1124 | B.137 | C.7 |
| 1.1125 | B.138 | C.7 |
| 1.1126 | B.139 | C.7 |
| 1.1127 | B.140 | C.7 |
| 1.1128 | B.141 | C.7 |
| 1.1129 | B.1 | C.8 |
| 1.1130 | B.2 | C.8 |
| 1.1131 | B.3 | C.8 |
| 1.1132 | B.4 | C.8 |
| 1.1133 | B.5 | C.8 |
| 1.1134 | B.6 | C.8 |
| 1.1135 | B.7 | C.8 |
| 1.1136 | B.8 | C.8 |
| 1.1137 | B.9 | C.8 |
| 1.1138 | B.10 | C.8 |
| 1.1139 | B.11 | C.8 |
| 1.1140 | B.12 | C.8 |
| 1.1141 | B.13 | C.8 |
| 1.1142 | B.14 | C.8 |
| 1.1143 | B.15 | C.8 |
| 1.1144 | B.16 | C.8 |
| 1.1145 | B.17 | C.8 |
| 1.1146 | B.18 | C.8 |
| 1.1147 | B.19 | C.8 |
| 1.1148 | B.20 | C.8 |
| 1.1149 | B.21 | C.8 |
| 1.1150 | B.22 | C.8 |
| 1.1151 | B.23 | C.8 |
| 1.1152 | B.24 | C.8 |
| 1.1153 | B.25 | C.8 |
| 1.1154 | B.26 | C.8 |
| 1.1155 | B.27 | C.8 |
| 1.1156 | B.28 | C.8 |
| 1.1157 | B.29 | C.8 |
| 1.1158 | B.30 | C.8 |
| 1.1159 | B.31 | C.8 |
| 1.1160 | B.32 | C.8 |
| 1.1161 | B.33 | C.8 |
| 1.1162 | B.34 | C.8 |
| 1.1163 | B.35 | C.8 |
| 1.1164 | B.36 | C.8 |
| 1.1165 | B.37 | C.8 |
| 1.1166 | B.38 | C.8 |
| 1.1167 | B.39 | C.8 |
| 1.1168 | B.40 | C.8 |
| 1.1169 | B.41 | C.8 |
| 1.1170 | B.42 | C.8 |
| 1.1171 | B.43 | C.8 |
| 1.1172 | B.44 | C.8 |
| 1.1173 | B.45 | C.8 |
| 1.1174 | B.46 | C.8 |
| 1.1175 | B.47 | C.8 |
| 1.1176 | B.48 | C.8 |
| 1.1177 | B.49 | C.8 |
| 1.1178 | B.50 | C.8 |
| 1.1179 | B.51 | C.8 |
| 1.1180 | B.52 | C.8 |
| 1.1181 | B.53 | C.8 |
| 1.1182 | B.54 | C.8 |
| 1.1183 | B.55 | C.8 |
| 1.1184 | B.56 | C.8 |
| 1.1185 | B.57 | C.8 |
| 1.1186 | B.58. | C.8 |
| 1.1187 | B.59 | C.8 |
| 1.1188 | B.60 | C.8 |
| 1.1189 | B.61 | C.8 |
| 1.1190 | B.62 | C.8 |
| 1.1191 | B.63 | C.8 |
| 1.1192 | B.64 | C.8 |
| 1.1193 | B.65 | C.8 |
| 1.1194 | B.66 | C.8 |
| 1.1195 | B.67 | C.8 |
| 1.1196 | B.68 | C.8 |
| 1.1197 | B.69 | C.8 |
| 1.1198 | B.70 | C.8 |
| 1.1199 | B.71 | C.8 |
| 1.1200 | B.72 | C.8 |
| 1.1201 | B.73 | C.8 |
| 1.1202 | B.74 | C.8 |
| 1.1203 | B.75 | C.8 |
| 1.1204 | B.76 | C.8 |
| 1.1205 | B.77 | C.8 |
| 1.1206 | B.78 | C.8 |
| 1.1207 | B.79 | C.8 |
| 1.1208 | B.80 | C.8 |
| 1.1209 | B.81 | C.8 |
| 1.1210 | B.82 | C.8 |
| 1.1211 | B.83 | C.8 |
| 1.1212 | B.84 | C.8 |
| 1.1213 | B.85 | C.8 |
| 1.1214 | B.86 | C.8 |
| 1.1215 | B.87 | C.8 |
| 1.1216 | B.88 | C.8 |
| 1.1217 | B.89 | C.8 |
| 1.1218 | B.90 | C.8 |
| 1.1219 | B.91 | |
| 1.1220 | B.92 | C.8 |
| 1.1221 | B.93 | C.8 |
| 1.1222 | B.94 | C.8 |
| 1.1223 | B.95 | C.8 |
| 1.1224 | B.96 | C.8 |
| 1.1225 | B.97 | C.8 |
| 1.1226 | B.98 | C.8 |
| 1.1227 | B.99 | C.8 |
| 1.1228 | B.100 | C.8 |
| 1.1229 | B.101 | C.8 |
| 1.1230 | B.102 | C.8 |
| 1.1231 | B.103 | C.8 |
| 1.1232 | B.104 | C.8 |
| 1.1233 | B.105 | C.8 |
| 1.1234 | B.106 | C.8 |
| 1.1235 | B.107 | C.8 |
| 1.1236 | B.108 | C.8 |
| 1.1237 | B.109 | C.8 |
| 1.1238 | B.110 | C.8 |
| 1.1239 | B.111 | C.8 |
| 1.1240 | B.112 | C.8 |
| 1.1241 | B.113 | C.8 |
| 1.1242 | B.114 | C.8 |
| 1.1243 | B.115 | C.8 |
| 1.1244 | B.116 | C.8 |
| 1.1245 | B.117 | C.8 |
| 1.1246 | B.118 | C.8 |
| 1.1247 | B.119 | C.8 |
| 1.1248 | B.120 | C.8 |
| 1.1249 | B.121 | C.8 |
| 1.1250 | B.122 | C.8 |
| 1.1251 | B.123 | C.8 |
| 1.1252 | B.124 | C.8 |

TABLE 1-continued (compositions 1.1 to 1.1833):

| comp. no. | herbicide B | safener C |
|---|---|---|
| 1.1253 | B.125 | C.8 |
| 1.1254 | B.126 | C.8 |
| 1.1255 | B.127 | C.8 |
| 1.1256 | B.128 | C.8 |
| 1.1257 | B.129 | C.8 |
| 1.1258 | B.130 | C.8 |
| 1.1259 | B.131 | C.8 |
| 1.1260 | B.132 | C.8 |
| 1.1261 | B.133 | C.8 |
| 1.1262 | B.134 | C.8 |
| 1.1263 | B.135 | C.8 |
| 1.1264 | B.136 | C.8 |
| 1.1265 | B.137 | C.8 |
| 1.1266 | B.138 | C.8 |
| 1.1267 | B.139 | C.8 |
| 1.1268 | B.140 | C.8 |
| 1.1269 | B.141 | C.8 |
| 1.1270 | B.1 | C.9 |
| 1.1271 | B.2 | C.9 |
| 1.1272 | B.3 | C.9 |
| 1.1273 | B.4 | C.9 |
| 1.1274 | B.5 | C.9 |
| 1.1275 | B.6 | C.9 |
| 1.1276 | B.7 | C.9 |
| 1.1277 | B.8 | C.9 |
| 1.1278 | B.9 | C.9 |
| 1.1279 | B.10 | C.9 |
| 1.1280 | B.11 | C.9 |
| 1.1281 | B.12 | C.9 |
| 1.1282 | B.13 | C.9 |
| 1.1283 | B.14 | C.9 |
| 1.1284 | B.15 | C.9 |
| 1.1285 | B.16 | C.9 |
| 1.1286 | B.17 | C.9 |
| 1.1287 | B.18 | C.9 |
| 1.1288 | B.19 | C.9 |
| 1.1289 | B.20 | C.9 |
| 1.1290 | B.21 | C.9 |
| 1.1291 | B.22 | C.9 |
| 1.1292 | B.23 | C.9 |
| 1.1293 | B.24 | C.9 |
| 1.1294 | B.25 | C.9 |
| 1.1295 | B.26 | C.9 |
| 1.1296 | B.27 | C.9 |
| 1.1297 | B.28 | C.9 |
| 1.1298 | B.29 | C.9 |
| 1.1299 | B.30 | C.9 |
| 1.1300 | B.31 | C.9 |
| 1.1301 | B.32 | C.9 |
| 1.1302 | B.33 | C.9 |
| 1.1303 | B.34 | C.9 |
| 1.1304 | B.35 | C.9 |
| 1.1305 | B.36 | C.9 |
| 1.1306 | B.37 | C.9 |
| 1.1307 | B.38 | C.9 |
| 1.1308 | B.39 | C.9 |
| 1.1309 | B.40 | C.9 |
| 1.1310 | B.41 | C.9 |
| 1.1311 | B.42 | C.9 |
| 1.1312 | B.43 | C.9 |
| 1.1313 | B.44 | C.9 |
| 1.1314 | B.45 | C.9 |
| 1.1315 | B.46 | C.9 |
| 1.1316 | B.47 | C.9 |
| 1.1317 | B.48 | C.9 |
| 1.1318 | B.49 | C.9 |
| 1.1319 | B.50 | C.9 |
| 1.1320 | B.51 | C.9 |
| 1.1321 | B.52 | C.9 |
| 1.1322 | B.53 | C.9 |
| 1.1323 | B.54 | C.9 |
| 1.1324 | B.55 | C.9 |
| 1.1325 | B.56 | C.9 |
| 1.1326 | B.57 | C.9 |
| 1.1327 | B.58. | C.9 |
| 1.1328 | B.59 | C.9 |
| 1.1329 | B.60 | C.9 |
| 1.1330 | B.61 | C.9 |
| 1.1331 | B.62 | C.9 |
| 1.1332 | B.63 | C.9 |
| 1.1333 | B.64 | C.9 |
| 1.1334 | B.65 | C.9 |
| 1.1335 | B.66 | C.9 |
| 1.1336 | B.67 | C.9 |
| 1.1337 | B.68 | C.9 |
| 1.1338 | B.69 | C.9 |
| 1.1339 | B.70 | C.9 |
| 1.1340 | B.71 | C.9 |
| 1.1341 | B.72 | C.9 |
| 1.1342 | B.73 | C.9 |
| 1.1343 | B.74 | C.9 |
| 1.1344 | B.75 | C.9 |
| 1.1345 | B.76 | C.9 |
| 1.1346 | B.77 | C.9 |
| 1.1347 | B.78 | C.9 |
| 1.1348 | B.79 | C.9 |
| 1.1349 | B.80 | C.9 |
| 1.1350 | B.81 | C.9 |
| 1.1351 | B.82 | C.9 |
| 1.1352 | B.83 | C.9 |
| 1.1353 | B.84 | C.9 |
| 1.1354 | B.85 | C.9 |
| 1.1355 | B.86 | C.9 |
| 1.1356 | B.87 | C.9 |
| 1.1357 | B.88 | C.9 |
| 1.1358 | B.89 | C.9 |
| 1.1359 | B.90 | C.9 |
| 1.1360 | B.91 | C.9 |
| 1.1361 | B.92 | C.9 |
| 1.1362 | B.93 | C.9 |
| 1.1363 | B.94 | C.9 |
| 1.1364 | B.95 | C.9 |
| 1.1365 | B.96 | C.9 |
| 1.1366 | B.97 | C.9 |
| 1.1367 | B.98 | C.9 |
| 1.1368 | B.99 | C.9 |
| 1.1369 | B.100 | C.9 |
| 1.1370 | B.101 | C.9 |
| 1.1371 | B.102 | C.9 |
| 1.1372 | B.103 | C.9 |
| 1.1373 | B.104 | C.9 |
| 1.1374 | B.105 | C.9 |
| 1.1375 | B.106 | C.9 |
| 1.1376 | B.107 | C.9 |
| 1.1377 | B.108 | C.9 |
| 1.1378 | B.109 | C.9 |
| 1.1379 | B.110 | C.9 |
| 1.1380 | B.111 | C.9 |
| 1.1381 | B.112 | C.9 |
| 1.1382 | B.113 | C.9 |
| 1.1383 | B.114 | C.9 |
| 1.1384 | B.115 | C.9 |
| 1.1385 | B.116 | C.9 |
| 1.1386 | B.117 | C.9 |
| 1.1387 | B.118 | C.9 |
| 1.1388 | B.119 | C.9 |
| 1.1389 | B.120 | C.9 |
| 1.1390 | B.121 | C.9 |
| 1.1391 | B.122 | C.9 |
| 1.1392 | B.123 | C.9 |
| 1.1393 | B.124 | C.9 |
| 1.1394 | B.125 | C.9 |
| 1.1395 | B.126 | C.9 |
| 1.1396 | B.127 | C.9 |
| 1.1397 | B.128 | C.9 |
| 1.1398 | B.129 | C.9 |
| 1.1399 | B.130 | C.9 |
| 1.1400 | B.131 | C.9 |
| 1.1401 | B.132 | C.9 |
| 1.1402 | B.133 | C.9 |

TABLE 1-continued (compositions 1.1 to 1.1833):

| comp. no. | herbicide B | safener C |
|---|---|---|
| 1.1403 | B.134 | C.9 |
| 1.1404 | B.135 | C.9 |
| 1.1405 | B.136 | C.9 |
| 1.1406 | B.137 | C.9 |
| 1.1407 | B.138 | C.9 |
| 1.1408 | B.139 | C.9 |
| 1.1409 | B.140 | C.9 |
| 1.1410 | B.141 | C.9 |
| 1.1411 | B.1 | C.10 |
| 1.1412 | B.2 | C.10 |
| 1.1413 | B.3 | C.10 |
| 1.1414 | B.4 | C.10 |
| 1.1415 | B.5 | C.10 |
| 1.1416 | B.6 | C.10 |
| 1.1417 | B.7 | C.10 |
| 1.1418 | B.8 | C.10 |
| 1.1419 | B.9 | C.10 |
| 1.1420 | B.10 | C.10 |
| 1.1421 | B.11 | C.10 |
| 1.1422 | B.12 | C.10 |
| 1.1423 | B.13 | C.10 |
| 1.1424 | B.14 | C.10 |
| 1.1425 | B.15 | C.10 |
| 1.1426 | B.16 | C.10 |
| 1.1427 | B.17 | C.10 |
| 1.1428 | B.18 | C.10 |
| 1.1429 | B.19 | C.10 |
| 1.1430 | B.20 | C.10 |
| 1.1431 | B.21 | C.10 |
| 1.1432 | B.22 | C.10 |
| 1.1433 | B.23 | C.10 |
| 1.1434 | B.24 | C.10 |
| 1.1435 | B.25 | C.10 |
| 1.1436 | B.26 | C.10 |
| 1.1437 | B.27 | C.10 |
| 1.1438 | B.28 | C.10 |
| 1.1439 | B.29 | C.10 |
| 1.1440 | B.30 | C.10 |
| 1.1441 | B.31 | C.10 |
| 1.1442 | B.32 | C.10 |
| 1.1443 | B.33 | C.10 |
| 1.1444 | B.34 | C.10 |
| 1.1445 | B.35 | C.10 |
| 1.1446 | B.36 | C.10 |
| 1.1447 | B.37 | C.10 |
| 1.1448 | B.38 | C.10 |
| 1.1449 | B.39 | C.10 |
| 1.1450 | B.40 | C.10 |
| 1.1451 | B.41 | C.10 |
| 1.1452 | B.42 | C.10 |
| 1.1453 | B.43 | C.10 |
| 1.1454 | B.44 | C.10 |
| 1.1455 | B.45 | C.10 |
| 1.1456 | B.46 | C.10 |
| 1.1457 | B.47 | C.10 |
| 1.1458 | B.48 | C.10 |
| 1.1459 | B.49 | C.10 |
| 1.1460 | B.50 | C.10 |
| 1.1461 | B.51 | C.10 |
| 1.1462 | B.52 | C.10 |
| 1.1463 | B.53 | C.10 |
| 1.1464 | B.54 | C.10 |
| 1.1465 | B.55 | C.10 |
| 1.1466 | B.56 | C.10 |
| 1.1467 | B.57 | C.10 |
| 1.1468 | B.58. | C.10 |
| 1.1469 | B.59 | C.10 |
| 1.1470 | B.60 | C.10 |
| 1.1471 | B.61 | C.10 |
| 1.1472 | B.62 | C.10 |
| 1.1473 | B.63 | C.10 |
| 1.1474 | B.64 | C.10 |
| 1.1475 | B.65 | C.10 |
| 1.1476 | B.66 | C.10 |
| 1.1477 | B.67 | C.10 |
| 1.1478 | B.68 | C.10 |
| 1.1479 | B.69 | C.10 |
| 1.1480 | B.70 | C.10 |
| 1.1481 | B.71 | C.10 |
| 1.1482 | B.72 | C.10 |
| 1.1483 | B.73 | C.10 |
| 1.1484 | B.74 | C.10 |
| 1.1485 | B.75 | C.10 |
| 1.1486 | B.76 | C.10 |
| 1.1487 | B.77 | C.10 |
| 1.1488 | B.78 | C.10 |
| 1.1489 | B.79 | C.10 |
| 1.1490 | B.80 | C.10 |
| 1.1491 | B.81 | C.10 |
| 1.1492 | B.82 | C.10 |
| 1.1493 | B.83 | C.10 |
| 1.1494 | B.84 | C.10 |
| 1.1495 | B.85 | C.10 |
| 1.1496 | B.86 | C.10 |
| 1.1497 | B.87 | C.10 |
| 1.1498 | B.88 | C.10 |
| 1.1499 | B.89 | C.10 |
| 1.1500 | B.90 | C.10 |
| 1.1501 | B.91 | C.10 |
| 1.1502 | B.92 | C.10 |
| 1.1503 | B.93 | C.10 |
| 1.1504 | B.94 | C.10 |
| 1.1505 | B.95 | C.10 |
| 1.1506 | B.96 | C.10 |
| 1.1507 | B.97 | C.10 |
| 1.1508 | B.98 | C.10 |
| 1.1509 | B.99 | C.10 |
| 1.1510 | B.100 | C.10 |
| 1.1511 | B.101 | C.10 |
| 1.1512 | B.102 | C.10 |
| 1.1513 | B.103 | C.10 |
| 1.1514 | B.104 | C.10 |
| 1.1515 | B.105 | C.10 |
| 1.1516 | B.106 | C.10 |
| 1.1517 | B.107 | C.10 |
| 1.1518 | B.108 | C.10 |
| 1.1519 | B.109 | C.10 |
| 1.1520 | B.110 | C.10 |
| 1.1521 | B.111 | C.10 |
| 1.1522 | B.112 | C.10 |
| 1.1523 | B.113 | C.10 |
| 1.1524 | B.114 | C.10 |
| 1.1525 | B.115 | C.10 |
| 1.1526 | B.116 | C.10 |
| 1.1527 | B.117 | C.10 |
| 1.1528 | B.118 | C.10 |
| 1.1529 | B.119 | C.10 |
| 1.1530 | B.120 | C.10 |
| 1.1531 | B.121 | C.10 |
| 1.1532 | B.122 | C.10 |
| 1.1533 | B.123 | C.10 |
| 1.1534 | B.124 | C.10 |
| 1.1535 | B.125 | C.10 |
| 1.1536 | B.126 | C.10 |
| 1.1537 | B.127 | C.10 |
| 1.1538 | B.128 | C.10 |
| 1.1539 | B.129 | C.10 |
| 1.1540 | B.130 | C.10 |
| 1.1541 | B.131 | C.10 |
| 1.1542 | B.132 | C.10 |
| 1.1543 | B.133 | C.10 |
| 1.1544 | B.134 | C.10 |
| 1.1545 | B.135 | C.10 |
| 1.1546 | B.136 | C.10 |
| 1.1547 | B.137 | C.10 |
| 1.1548 | B.138 | C.10 |
| 1.1549 | B.139 | C.10 |
| 1.1550 | B.140 | C.10 |
| 1.1551 | B.141 | C.10 |
| 1.1552 | B.1 | C.11 |

TABLE 1-continued (compositions 1.1 to 1.1833):

| comp. no. | herbicide B | safener C |
|---|---|---|
| 1.1553 | B.2 | C.11 |
| 1.1554 | B.3 | C.11 |
| 1.1555 | B.4 | C.11 |
| 1.1556 | B.5 | C.11 |
| 1.1557 | B.6 | C.11 |
| 1.1558 | B.7 | C.11 |
| 1.1559 | B.8 | C.11 |
| 1.1560 | B.9 | C.11 |
| 1.1561 | B.10 | C.11 |
| 1.1562 | B.11 | C.11 |
| 1.1563 | B.12 | C.11 |
| 1.1564 | B.13 | C.11 |
| 1.1565 | B.14 | C.11 |
| 1.1566 | B.15 | C.11 |
| 1.1567 | B.16 | C.11 |
| 1.1568 | B.17 | C.11 |
| 1.1569 | B.18 | C.11 |
| 1.1570 | B.19 | C.11 |
| 1.1571 | B.20 | C.11 |
| 1.1572 | B.21 | C.11 |
| 1.1573 | B.22 | C.11 |
| 1.1574 | B.23 | C.11 |
| 1.1575 | B.24 | C.11 |
| 1.1576 | B.25 | C.11 |
| 1.1577 | B.26 | C.11 |
| 1.1578 | B.27 | C.11 |
| 1.1579 | B.28 | C.11 |
| 1.1580 | B.29 | C.11 |
| 1.1581 | B.30 | C.11 |
| 1.1582 | B.31 | C.11 |
| 1.1583 | B.32 | C.11 |
| 1.1584 | B.33 | C.11 |
| 1.1585 | B.34 | C.11 |
| 1.1586 | B.35 | C.11 |
| 1.1587 | B.36 | C.11 |
| 1.1588 | B.37 | C.11 |
| 1.1589 | B.38 | C.11 |
| 1.1590 | B.39 | C.11 |
| 1.1591 | B.40 | C.11 |
| 1.1592 | B.41 | C.11 |
| 1.1593 | B.42 | C.11 |
| 1.1594 | B.43 | C.11 |
| 1.1595 | B.44 | C.11 |
| 1.1596 | B.45 | C.11 |
| 1.1597 | B.46 | C.11 |
| 1.1598 | B.47 | C.11 |
| 1.1599 | B.48 | C.11 |
| 1.1600 | B.49 | C.11 |
| 1.1601 | B.50 | C.11 |
| 1.1602 | B.51 | C.11 |
| 1.1603 | B.52 | C.11 |
| 1.1604 | B.53 | C.11 |
| 1.1605 | B.54 | C.11 |
| 1.1606 | B.55 | C.11 |
| 1.1607 | B.56 | C.11 |
| 1.1608 | B.57 | C.11 |
| 1.1609 | B.58. | C.11 |
| 1.1610 | B.59 | C.11 |
| 1.1611 | B.60 | C.11 |
| 1.1612 | B.61 | C.11 |
| 1.1613 | B.62 | C.11 |
| 1.1614 | B.63 | C.11 |
| 1.1615 | B.64 | C.11 |
| 1.1616 | B.65 | C.11 |
| 1.1617 | B.66 | C.11 |
| 1.1618 | B.67 | C.11 |
| 1.1619 | B.68 | C.11 |
| 1.1620 | B.69 | C.11 |
| 1.1621 | B.70 | C.11 |
| 1.1622 | B.71 | C.11 |
| 1.1623 | B.72 | C.11 |
| 1.1624 | B.73 | C.11 |
| 1.1625 | B.74 | C.11 |
| 1.1626 | B.75 | C.11 |
| 1.1627 | B.76 | C.11 |
| 1.1628 | B.77 | C.11 |
| 1.1629 | B.78 | C.11 |
| 1.1630 | B.79 | C.11 |
| 1.1631 | B.80 | C.11 |
| 1.1632 | B.81 | C.11 |
| 1.1633 | B.82 | C.11 |
| 1.1634 | B.83 | C.11 |
| 1.1635 | B.84 | C.11 |
| 1.1636 | B.85 | C.11 |
| 1.1637 | B.86 | C.11 |
| 1.1638 | B.87 | C.11 |
| 1.1639 | B.88 | C.11 |
| 1.1640 | B.89 | C.11 |
| 1.1641 | B.90 | C.11 |
| 1.1642 | B.91 | C.11 |
| 1.1643 | B.92 | C.11 |
| 1.1644 | B.93 | C.11 |
| 1.1645 | B.94 | C.11 |
| 1.1646 | B.95 | C.11 |
| 1.1647 | B.96 | C.11 |
| 1.1648 | B.97 | C.11 |
| 1.1649 | B.98 | C.11 |
| 1.1650 | B.99 | C.11 |
| 1.1651 | B.100 | C.11 |
| 1.1652 | B.101 | C.11 |
| 1.1653 | B.102 | C.11 |
| 1.1654 | B.103 | C.11 |
| 1.1655 | B.104 | C.11 |
| 1.1656 | B.105 | C.11 |
| 1.1657 | B.106 | C.11 |
| 1.1658 | B.107 | C.11 |
| 1.1659 | B.108 | C.11 |
| 1.1660 | B.109 | C.11 |
| 1.1661 | B.110 | C.11 |
| 1.1662 | B.111 | C.11 |
| 1.1663 | B.112 | C.11 |
| 1.1664 | B.113 | C.11 |
| 1.1665 | B.114 | C.11 |
| 1.1666 | B.115 | C.11 |
| 1.1667 | B.116 | C.11 |
| 1.1668 | B.117 | C.11 |
| 1.1669 | B.118 | C.11 |
| 1.1670 | B.119 | C.11 |
| 1.1671 | B.120 | C.11 |
| 1.1672 | B.121 | C.11 |
| 1.1673 | B.122 | C.11 |
| 1.1674 | B.123 | C.11 |
| 1.1675 | B.124 | C.11 |
| 1.1676 | B.125 | C.11 |
| 1.1677 | B.126 | C.11 |
| 1.1678 | B.127 | C.11 |
| 1.1679 | B.128 | C.11 |
| 1.1680 | B.129 | C.11 |
| 1.1681 | B.130 | C.11 |
| 1.1682 | B.131 | C.11 |
| 1.1683 | B.132 | C.11 |
| 1.1684 | B.133 | C.11 |
| 1.1685 | B.134 | C.11 |
| 1.1686 | B.135 | C.11 |
| 1.1687 | B.136 | C.11 |
| 1.1688 | B.137 | C.11 |
| 1.1689 | B.138 | C.11 |
| 1.1690 | B.139 | C.11 |
| 1.1691 | B.140 | C.11 |
| 1.1692 | B.141 | C.11 |
| 1.1693 | B.1 | C.12 |
| 1.1694 | B.2 | C.12 |
| 1.1695 | B.3 | C.12 |
| 1.1696 | B.4 | C.12 |
| 1.1697 | B.5 | C.12 |
| 1.1698 | B.6 | C.12 |
| 1.1699 | B.7 | C.12 |
| 1.1700 | B.8 | C.12 |
| 1.1701 | B.9 | C.12 |
| 1.1702 | B.10 | C.12 |

TABLE 1-continued (compositions 1.1 to 1.1833):

| comp. no. | herbicide B | safener C |
|---|---|---|
| 1.1703 | B.11 | C.12 |
| 1.1704 | B.12 | C.12 |
| 1.1705 | B.13 | C.12 |
| 1.1706 | B.14 | C.12 |
| 1.1707 | B.15 | C.12 |
| 1.1708 | B.16 | C.12 |
| 1.1709 | B.17 | C.12 |
| 1.1710 | B.18 | C.12 |
| 1.1711 | B.19 | C.12 |
| 1.1712 | B.20 | C.12 |
| 1.1713 | B.21 | C.12 |
| 1.1714 | B.22 | C.12 |
| 1.1715 | B.23 | C.12 |
| 1.1716 | B.24 | C.12 |
| 1.1717 | B.25 | C.12 |
| 1.1718 | B.26 | C.12 |
| 1.1719 | B.27 | C.12 |
| 1.1720 | B.28 | C.12 |
| 1.1721 | B.29 | C.12 |
| 1.1722 | B.30 | C.12 |
| 1.1723 | B.31 | C.12 |
| 1.1724 | B.32 | C.12 |
| 1.1725 | B.33 | C.12 |
| 1.1726 | B.34 | C.12 |
| 1.1727 | B.35 | C.12 |
| 1.1728 | B.36 | C.12 |
| 1.1729 | B.37 | C.12 |
| 1.1730 | B.38 | C.12 |
| 1.1731 | B.39 | C.12 |
| 1.1732 | B.40 | C.12 |
| 1.1733 | B.41 | C.12 |
| 1.1734 | B.42 | C.12 |
| 1.1735 | B.43 | C.12 |
| 1.1736 | B.44 | C.12 |
| 1.1737 | B.45 | C.12 |
| 1.1738 | B.46 | C.12 |
| 1.1739 | B.47 | C.12 |
| 1.1740 | B.48 | C.12 |
| 1.1741 | B.49 | C.12 |
| 1.1742 | B.50 | C.12 |
| 1.1743 | B.51 | C.12 |
| 1.1744 | B.52 | C.12 |
| 1.1745 | B.53 | C.12 |
| 1.1746 | B.54 | C.12 |
| 1.1747 | B.55 | C.12 |
| 1.1748 | B.56 | C.12 |
| 1.1749 | B.57 | C.12 |
| 1.1750 | B.58. | C.12 |
| 1.1751 | B.59 | C.12 |
| 1.1752 | B.60 | C.12 |
| 1.1753 | B.61 | C.12 |
| 1.1754 | B.62 | C.12 |
| 1.1755 | B.63 | C.12 |
| 1.1756 | B.64 | C.12 |
| 1.1757 | B.65 | C.12 |
| 1.1758 | B.66 | C.12 |
| 1.1759 | B.67 | C.12 |
| 1.1760 | B.68 | C.12 |
| 1.1761 | B.69 | C.12 |
| 1.1762 | B.70 | C.12 |
| 1.1763 | B.71 | C.12 |
| 1.1764 | B.72 | C.12 |
| 1.1765 | B.73 | C.12 |
| 1.1766 | B.74 | C.12 |
| 1.1767 | B.75 | C.12 |
| 1.1768 | B.76 | C.12 |
| 1.1769 | B.77 | C.12 |
| 1.1770 | B.78 | C.12 |
| 1.1771 | B.79 | C.12 |
| 1.1772 | B.80 | C.12 |
| 1.1773 | B.81 | C.12 |
| 1.1774 | B.82 | C.12 |
| 1.1775 | B.83 | C.12 |
| 1.1776 | B.84 | C.12 |
| 1.1777 | B.85 | C.12 |
| 1.1778 | B.86 | C.12 |
| 1.1779 | B.87 | C.12 |
| 1.1780 | B.88 | C.12 |
| 1.1781 | B.89 | C.12 |
| 1.1782 | B.90 | C.12 |
| 1.1783 | B.91 | C.12 |
| 1.1784 | B.92 | C.12 |
| 1.1785 | B.93 | C.12 |
| 1.1786 | B.94 | C.12 |
| 1.1787 | B.95 | C.12 |
| 1.1788 | B.96 | C.12 |
| 1.1789 | B.97 | C.12 |
| 1.1790 | B.98 | C.12 |
| 1.1791 | B.99 | C.12 |
| 1.1792 | B.100 | C.12 |
| 1.1793 | B.101 | C.12 |
| 1.1794 | B.102 | C.12 |
| 1.1795 | B.103 | C.12 |
| 1.1796 | B.104 | C.12 |
| 1.1797 | B.105 | C.12 |
| 1.1798 | B.106 | C.12 |
| 1.1799 | B.107 | C.12 |
| 1.1800 | B.108 | C.12 |
| 1.1801 | B.109 | C.12 |
| 1.1802 | B.110 | C.12 |
| 1.1803 | B.111 | C.12 |
| 1.1804 | B.112 | C.12 |
| 1.1805 | B.113 | C.12 |
| 1.1806 | B.114 | C.12 |
| 1.1807 | B.115 | C.12 |
| 1.1808 | B.116 | C.12 |
| 1.1809 | B.117 | C.12 |
| 1.1810 | B.118 | C.12 |
| 1.1811 | B.119 | C.12 |
| 1.1812 | B.120 | C.12 |
| 1.1813 | B.121 | C.12 |
| 1.1814 | B.122 | C.12 |
| 1.1815 | B.123 | C.12 |
| 1.1816 | B.124 | C.12 |
| 1.1817 | B.125 | C.12 |
| 1.1818 | B.126 | C.12 |
| 1.1819 | B.127 | C.12 |
| 1.1820 | B.128 | C.12 |
| 1.1821 | B.129 | C.12 |
| 1.1822 | B.130 | C.12 |
| 1.1823 | B.131 | C.12 |
| 1.1824 | B.132 | C.12 |
| 1.1825 | B.133 | C.12 |
| 1.1826 | B.134 | C.12 |
| 1.1827 | B.135 | C.12 |
| 1.1828 | B.136 | C.12 |
| 1.1829 | B.137 | C.12 |
| 1.1830 | B.138 | C.12 |
| 1.1831 | B.139 | C.12 |
| 1.1832 | B.140 | C.12 |
| 1.1833 | B.141 | C.12 |

The specific number for each single composition is deductible as follows:

Composition 1.777 for example comprises the benzoxazinone I.a.35, flumioxazin (B.72) and fenclorim (C.5) (see table 1, entry 1.777; as well as table B, entry B.72 and table C, entry C.5).

Composition 7.777 for example comprises imazaquin (B32) (see the definition for compositions 7.1 to 7.1692 below), and the benzoxazinone I.a.35, flumioxazin (B.72) and fenclorim (C.5) (see table 1, entry 1.777; as well as table B, entry B.77 and table C, entry C.5).

Also especially preferred are compositions 2.1 to 2.1833, preferably compositions 2.1 to 2.1692, which differ from the corresponding compositions 1.1 to 1.1833, preferably compositions 1.1 to 1.1692, only in that they additionally comprise B.2 as further herbicide B.

Also especially preferred are compositions 3.1 to 3.1833, preferably compositions 3.1 to 3.1692, which differ from the corresponding compositions 1.1 to 1.1833, preferably compositions 1.1 to 1.1692, only in that they additionally comprise B.7 as further herbicide B.

Also especially preferred are compositions 4.1 to 4.1833, preferably compositions 4.1 to 4.1692, which differ from the corresponding compositions 1.1 to 1.1833, preferably compositions 1.1 to 1.1692, only in that they additionally comprise B.29 as further herbicide B.

Also especially preferred are compositions 5.1 to 5.1833, preferably compositions 5.1 to 5.1692, which differ from the corresponding compositions 1.1 to 1.1833, preferably compositions 1.1 to 1.1692, only in that they additionally comprise B.30 as further herbicide B.

Also especially preferred are compositions 6.1 to 6.1833, preferably compositions 6.1 to 6.1692, which differ from the corresponding compositions 1.1 to 1.1833, preferably compositions 1.1 to 1.1692, only in that they additionally comprise B.31 as further herbicide B.

Also especially preferred are compositions 7.1 to 7.1833, preferably compositions 7.17 to 7.1692, which differ from the corresponding compositions 1.1 to 1.1833, preferably compositions 1.1 to 1.1692, only in that they additionally comprise B.32 as further herbicide B.

Also especially preferred are compositions 8.1 to 8.1833, preferably compositions 8.1 to 8.1692, which differ from the corresponding compositions 1.1 to 1.1833, preferably compositions 1.1 to 1.1692, only in that they additionally comprise B.33 as further herbicide B.

Also especially preferred are compositions 9.1 to 9.1833, preferably compositions 9.1 to 9.1692, which differ from the corresponding compositions 1.1 to 1.1833, preferably compositions 1.1 to 1.1692, only in that they additionally comprise B.40 as further herbicide B.

Also especially preferred are compositions 10.1 to 10.1833, preferably compositions 10.1. to 10.1692, which differ from the corresponding compositions 1.1 to 1.1833, preferably compositions 1.1 to 1.1692, only in that they additionally comprise B.44 as further herbicide B.

Also especially preferred are compositions 11.1 to 11.1833, preferably compositions 11.1 to 11.1692, which differ from the corresponding compositions 1.1 to 1.1833, preferably compositions 1.1 to 1.1692, only in that they additionally comprise B.45 as further herbicide B.

Also especially preferred are compositions 12.1 to 12.1833, preferably compositions 12.1 to 12.1692, which differ from the corresponding compositions 1.1 to 1.1833, preferably compositions 1.1 to 1.1692, only in that they additionally comprise B.52 as further herbicide B.

Also especially preferred are compositions 13.1 to 13.1833, preferably compositions 13.1 to 13.1692, which differ from the corresponding compositions 1.1 to 1.1833, preferably compositions 1.1 to 1.1692, only in that they additionally comprise B.53 as further herbicide B.

Also especially preferred are compositions 14.1 to 14.1833, preferably compositions 14.1 to 14.1692, which differ from the corresponding compositions 1.1 to 1.1833, preferably compositions 1.1 to 1.1692, only in that they additionally comprise B.54 as further herbicide B.

Also especially preferred are compositions 15.1 to 15.1833, preferably compositions 15.1 to 15.1692, which differ from the corresponding compositions 1.1 to 1.1833, preferably compositions 1.1 to 1.1692, only in that they additionally comprise B.55 as further herbicide B.

Also especially preferred are compositions 16.1 to 16.1833, preferably compositions 16.1 to 16.1692, which differ from the corresponding compositions 1.1 to 1.1833, preferably compositions 1.1 to 1.1692, only in that they additionally comprise B.56 as further herbicide B.

Also especially preferred are compositions 17.1 to 17.1833, preferably compositions 17.1 to 17.1692, which differ from the corresponding compositions 1.1 to 1.1833, preferably compositions 1.1 to 1.1692, only in that they additionally comprise B.57 as further herbicide B.

Also especially preferred are compositions 18.1 to 18.1833, preferably compositions 18.1 to 18.1692, which differ from the corresponding compositions 1.1 to 1.1833, preferably compositions 1.1 to 1.1692, only in that they additionally comprise B.60 as further herbicide B.

Also especially preferred are compositions 19.1 to 19.1833, preferably compositions 19.1 to 19.1692, which differ from the corresponding compositions 1.1 to 1.1833, preferably compositions 1.1 to 1.1692, only in that they additionally comprise B.65 as further herbicide B.

Also especially preferred are compositions 20.1 to 20.1833, preferably compositions 20.1 to 20.1692, which differ from the corresponding compositions 1.1 to 1.1833, preferably compositions 1.1 to 1.1692, only in that they additionally comprise B.66 as further herbicide B.

Also especially preferred are compositions 21.1 to 21.1833, preferably compositions 21.1 to 21.1692, which differ from the corresponding compositions 1.1 to 1.1833, preferably compositions 1.1 to 1.1692, only in that they additionally comprise B.69 as further herbicide B.

Also especially preferred are compositions 22.1 to 22.1833, preferably compositions 22.1 to 22.1692, which differ from the corresponding compositions 1.1 to 1.1833, preferably compositions 1.1 to 1.1692, only in that they additionally comprise B.72 as further herbicide B.

Also especially preferred are compositions 23.1 to 23.1833, preferably compositions 23.1 to 23.1692, which differ from the corresponding compositions 1.1 to 1.1833, preferably compositions 1.1 to 1.1692, only in that they additionally comprise B.73 as further herbicide B.

Also especially preferred are compositions 24.1 to 24.1833, preferably compositions 24.1 to 24.1692, which differ from the corresponding compositions 1.1 to 1.1833, preferably compositions 1.1 to 1.1692, only in that they additionally comprise B.76 as further herbicide B.

Also especially preferred are compositions 25.1 to 25.1833, preferably compositions 25.1 to 25.1692, which differ from the corresponding compositions 1.1 to 1.1833, preferably compositions 1.1 to 1.1692, only in that they additionally comprise B.77 as further herbicide B.

Also especially preferred are compositions 26.1 to 26.1833, preferably compositions 26.1 to 26.1692, which differ from the corresponding compositions 1.1 to 1.1833, preferably compositions 1.1 to 1.1692, only in that they additionally comprise B.80 as further herbicide B.

Also especially preferred are compositions 27.1 to 27.1833, preferably compositions 27.1 to 27.1692, which differ from the corresponding compositions 1.1 to 1.1833, preferably compositions 1.1 to 1.1692, only in that they additionally comprise B.81 as further herbicide B.

Also especially preferred are compositions 28.1 to 28.1833, preferably compositions 28.1 to 28.1692, which differ from the corresponding compositions 1.1 to 1.1833, preferably compositions 1.1 to 1.1692, only in that they additionally comprise B.84 as further herbicide B.

Also especially preferred are compositions 29.1 to 29.1833, preferably compositions 29.1 to 29.1692, which differ from the corresponding compositions 1.1 to 1.1833, preferably compositions 1.1 to 1.1692, only in that they additionally comprise B.84 and B.54 as further herbicides B.

Also especially preferred are compositions 30.1 to 30.1833, preferably compositions 30.1 to 30.1692, which differ from the corresponding compositions 1.1 to 1.1833, preferably compositions 1.1 to 1.1692, only in that they additionally comprise B.84 and B.60 as further herbicides B.

Also especially preferred are compositions 31.1 to 31.1833, preferably compositions 31.1 to 31.1692, which differ from the corresponding compositions 1.1 to 1.1833, preferably compositions 1.1 to 1.1692, only in that they additionally comprise B.84 and B.66 as further herbicides B.

Also especially preferred are compositions 32.1 to 32.1833, preferably compositions 32.1 to 32.1692, which differ from the corresponding compositions 1.1 to 1.1833, preferably compositions 1.1 to 1.1692, only in that they additionally comprise B. 85 as further herbicide B.

Also especially preferred are compositions 33.1 to 33.1833, preferably compositions 33.1 to 33.1692, which differ from the corresponding compositions 1.1 to 1.1833, preferably compositions 1.1 to 1.1692, only in that they additionally comprise B. 85 and B.54 as further herbicides B.

Also especially preferred are compositions 34.1 to 34.1833, preferably compositions 34.1 to 34.1692, which differ from the corresponding compositions 1.1 to 1.1833, preferably compositions 1.1 to 1.1692, only in that they additionally comprise B. 85 and B.60 as further herbicides B.

Also especially preferred are compositions 35.1 to 35.1833, preferably compositions 35.1 to 35.1692, which differ from the corresponding compositions 1.1 to 1.1833, preferably compositions 1.1 to 1.1692, only in that they additionally comprise B. 85 and B.66 as further herbicides B.

Also especially preferred are compositions 36.1 to 36.1833, preferably compositions 36.1 to 36.1692, which differ from the corresponding compositions 1.1 to 1.1833, preferably compositions 1.1 to 1.1692, only in that they additionally comprise B.87 as further herbicide B.

Also especially preferred are compositions 37.1 to 37.1833, preferably compositions 37.1 to 37.1692, which differ from the corresponding compositions 1.1 to 1.1833, preferably compositions 1.1 to 1.1692, only in that they additionally comprise B. 88 as further herbicide B.

Also especially preferred are compositions 38.1 to 38.1833, preferably compositions 38.1 to 38.1692, which differ from the corresponding compositions 1.1 to 1.1833, preferably compositions 1.1 to 1.1692, only in that they additionally comprise B. 88 and B.54 as further herbicides B.

Also especially preferred are compositions 39.1 to 39.1833, preferably compositions 39.1 to 39.1692, which differ from the corresponding compositions 1.1 to 1.1833, preferably compositions 1.1 to 1.1692, only in that they additionally comprise B. 88 and B.60 as further herbicides B.

Also especially preferred are compositions 40.1 to 40.1833, preferably compositions 40.1 to 40.1692, which differ from the corresponding compositions 1.1 to 1.1833, preferably compositions 1.1 to 1.1692, only in that they additionally comprise B. 88 and B.66 as further herbicides B.

Also especially preferred are compositions 41.1 to 41.1833, preferably compositions 41.1 to 41.1692, which differ from the corresponding compositions 1.1 to 1.1833, preferably compositions 1.1 to 1.1692, only in that they additionally comprise B.90 as further herbicide B.

Also especially preferred are compositions 42.1 to 42.1833, preferably compositions 42.1 to 42.1692, which differ from the corresponding compositions 1.1 to 1.1833, preferably compositions 1.1 to 1.1692, only in that they additionally comprise B.91 as further herbicide B.

Also especially preferred are compositions 43.1 to 43.1833, preferably compositions 43.1 to 43.1692, which differ from the corresponding compositions 1.1 to 1.1833, preferably compositions 1.1 to 1.1692, only in that they additionally comprise B.91 and B.54 as further herbicides B.

Also especially preferred are compositions 44.1 to 44.1833, preferably compositions 44.1 to 44.1692, which differ from the corresponding compositions 1.1 to 1.1833, preferably compositions 1.1 to 1.1692, only in that they additionally comprise B.91 and B.60 as further herbicides B.

Also especially preferred are compositions 45.1 to 45.1833, preferably compositions 45.1 to 45.1692, which differ from the corresponding compositions 1.1 to 1.1833, preferably compositions 1.1 to 1.1692, only in that they additionally comprise B.91 and B.66 as further herbicides B.

Also especially preferred are compositions 46.1 to 46.1833, preferably compositions 46.1 to 46.1692, which differ from the corresponding compositions 1.1 to 1.1833, preferably compositions 1.1 to 1.1692, only in that they additionally comprise B.95 as further herbicide B.

Also especially preferred are compositions 47.1 to 47.1833, preferably compositions 47.1 to 47.1692, which differ from the corresponding compositions 1.1 to 1.1833, preferably compositions 1.1 to 1.1692, only in that they additionally comprise B.95 and B.54 as further herbicides B.

Also especially preferred are compositions 48.1 to 48.1833, preferably compositions 48.1 to 48.1692, which differ from the corresponding compositions 1.1 to 1.1833, preferably compositions 1.1 to 1.1692, only in that they additionally comprise B.95 and B.76 as further herbicides B.

Also especially preferred are compositions 49.1 to 49.1833, preferably compositions 49.1 to 49.1692, which differ from the corresponding compositions 1.1 to 1.1833, preferably compositions 1.1 to 1.1692, only in that they additionally comprise B.95 and B.84 as further herbicides B.

Also especially preferred are compositions 50.1 to 50.1833, preferably compositions 50.1 to 50.1692, which differ from the corresponding compositions 1.1 to 1.1833, preferably compositions 1.1 to 1.1692, only in that they additionally comprise B.95 and B.103 as further herbicides B.

Also especially preferred are compositions 51.1 to 51.1833, preferably compositions 51.1 to 51.1692, which differ from the corresponding compositions 1.1 to 1.1833, preferably compositions 1.1 to 1.1692, only in that they additionally comprise B.95 and B.85 as further herbicides B.

Also especially preferred are compositions 52.1 to 52.1833, preferably compositions 52.1 to 52.1692, which differ from the corresponding compositions 1.1 to 1.1833, preferably compositions 1.1 to 1.1692, only in that they additionally comprise B.95 and B.88 as further herbicides B.

Also especially preferred are compositions 53.1 to 53.1833, preferably compositions 53.1 to 53.1692, which differ from the corresponding compositions 1.1 to 1.1833, preferably compositions 1.1 to 1.1692, only in that they additionally comprise B.95 and B.91 as further herbicides B.

Also especially preferred are compositions 54.1 to 54.1833, preferably compositions 54.1 to 54.1692, which differ from the corresponding compositions 1.1 to 1.1833, preferably compositions 1.1 to 1.1692, only in that they additionally comprise B.98 as further herbicide B.

Also especially preferred are compositions 55.1 to 55.1833, preferably compositions 55.1 to 55.1692, which differ from the corresponding compositions 1.1 to 1.1833, preferably compositions 1.1 to 1.1692, only in that they additionally comprise B.101 as further herbicide B.

Also especially preferred are compositions 56.1 to 56.1833, preferably compositions 56.1 to 56.1692, which differ from the corresponding compositions 1.1 to 1.1833, preferably compositions 1.1 to 1.1692, only in that they additionally comprise B.103 as further herbicide B.

Also especially preferred are compositions 57.1 to 57.1833, preferably compositions 57.1 to 57.1692, which differ from the corresponding compositions 1.1 to 1.1833, preferably compositions 1.1 to 1.1692, only in that they additionally comprise B.106 as further herbicide B.

Also especially preferred are compositions 58.1 to 58.1833, preferably compositions 58.1 to 58.1692, which differ from the corresponding compositions 1.1 to 1.1833, preferably compositions 1.1 to 1.1692, only in that they additionally comprise B.107 as further herbicide B.

Also especially preferred are compositions 59.1 to 59.1833, preferably compositions 59.1 to 59.1692, which differ from the corresponding compositions 1.1 to 1.1833, preferably compositions 1.1 to 1.1692, only in that they additionally comprise B.108 as further herbicide B.

Also especially preferred are compositions 60.1 to 60.1833, preferably compositions 60.1 to 60.1692, which differ from the corresponding compositions 1.1 to 1.1833, preferably compositions 1.1 to 1.1692, only in that they additionally comprise B.110 as further herbicide B.

Also especially preferred are compositions 61.1 to 61.1833, preferably compositions 61.1 to 61.1692, which differ from the corresponding compositions 1.1 to 1.1833, preferably compositions 1.1 to 1.1692, only in that they additionally comprise B.112 as further herbicide B.

Also especially preferred are compositions 62.1 to 62.1833, preferably compositions 62.1 to 62.1692, which differ from the corresponding compositions 1.1 to 1.1833, preferably compositions 11.1 to 1.1692, only in that they additionally comprise B.113 as further herbicide B.

Also especially preferred are compositions 63.1 to 63.1833, preferably compositions 63.1 to 63.1692, which differ from the corresponding compositions 1.1 to 1.1833, preferably compositions 1.1 to 1.1692, only in that they additionally comprise B.117 as further herbicide B.

Also especially preferred are compositions 64.1 to 64.1833, preferably compositions 64.1 to 64.1692, which differ from the corresponding compositions 1.1 to 1.1833, preferably compositions 1.1 to 1.1692, only in that they additionally comprise B.119 as further herbicide B.

Also especially preferred are compositions 65.1 to 65.1833, preferably compositions 65.1 to 65.1692, which differ from the corresponding compositions 1.1 to 1.1833, preferably compositions 1.1 to 1.1692, only in that they additionally comprise B.120 as further herbicide B.

Also especially preferred are compositions 66.1 to 66.1833, preferably compositions 66.1 to 66.1692, which differ from the corresponding compositions 1.1 to 1.1833, preferably compositions 1.1 to 1.1692, only in that they additionally comprise B.122 as further herbicide B.

Also especially preferred are compositions 67.1 to 67.1833, preferably compositions 67.1 to 67.1692, which differ from the corresponding compositions 1.1 to 1.1833, preferably compositions 1.1 to 1.1692, only in that they additionally comprise B.123 as further herbicide B.

Also especially preferred are compositions 68.1 to 68.1833, preferably compositions 68.1 to 68.1692, which differ from the corresponding compositions 1.1 to 1.1833, preferably compositions 1.1 to 1.1692, only in that they additionally comprise B.130 as further herbicide B.

Also especially preferred are compositions 69.1 to 69.12, preferably compositions 69.1 to 69.11, comprising as active compound A) the benzoxazinone compound Ia.35 and as further compound the substance as defined in the respective row of table C:

TABLE C

| comp. no. | safener C |
|---|---|
| 69.1 | C.1 |
| 69.2 | C.2 |
| 69.3 | C.3 |
| 69.4 | C.4 |
| 69.5 | C.5 |
| 69.6 | C.6 |
| 69.7 | C.7 |
| 69.8 | C.8 |
| 69.9 | C.9 |
| 69.10 | C.10 |
| 69.11 | C.11 |
| 69.12 | C.12 |

According to one embodiment of the invention, in the ready-to-use preparations of herbicidal compositions, i.e. in the compositions according to the invention in the form of crop protection compositions, the components A (benzoxazinone of formula I) and B and/or C can be present formulated jointly or separately in suspended, emulsified or dissolved form. The use forms depend entirely on the intended applications.

Accordingly, a first embodiment of the invention relates to compositions in the form of a crop protection composition formulated as a 1-component composition comprising the at least one active compound of the formula I or the at least one active compound of the formula I (active compound A) and at least one further active compound selected from the herbicides B and the safeners C and also a solid or liquid carrier and, if appropriate, one or more surfactants.

Accordingly, a second embodiment of the invention relates to compositions in the form of a crop protection composition formulated as a 2-component composition comprising a first formulation (component) comprising the at least one active compound A, a solid or liquid carrier and, if appropriate, one or more surfactants, and a second component comprising at least one further active compound selected from the herbicides B and safeners C, a solid or liquid carrier and, if appropriate, one or more surfactants.

The active compound A and the at least one further active compound B and/or C can be applied jointly or separately, simultaneously or in succession, before, during or after the emergence of the plants. The order of the application of the active compounds A, B and/or C is of minor importance. The only thing that is important is that the at least one active compound A and the at least one further active compound B and/or C are present simultaneously at the site of action, i.e. are at the same time in contact with or taken up by the plant to be controlled.

The required application rate of pure active compound composition, i.e. A and B and, if appropriate, C without formulation auxiliaries depends on the composition of the plant stand, on the development stage of the plants, on the climatic conditions at the site of use and on the application technique. In general, the application rate of A and B and, if appropriate, C, is from 0.001 to 3 kg/ha, preferably from 0.005 to 2.5 kg/ha and in particular from 0.01 to 2 kg/ha of active substance (a.s.).

According to one embodiment of the invention the required application rates of compounds I, are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of compounds B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of compounds C are generally in the range of from 0.0005 kg/ha to 2.5 kg/ha and preferably in the range of from 0.005 kg/ha to 2 kg/ha or 0.01 kg/ha to 1.5 kg/h of a.s.

The benzoxazinones of formula I and the compositions according to the invention comprising them are applied to the plants mainly by spraying the leaves. Here, the application can be carried out using, for example, water as carrier by customary spraying techniques using spray liquor amounts of from about 100 to 1000 l/ha (for example from 300 to 400 l/ha). The herbicidal compositions may also be applied by the low-volume or the ultra-low-volume method, or in the form of microgranules.

The benzoxazinones of formula I and the herbicidal compositions according to the present invention can be applied pre- or post-emergence, or together with the seed of a crop plant. It is also possible to apply the compounds and compositions by applying seed, pretreated with a composition of the invention, of a crop plant. If the active compounds A and B and, if appropriate C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

Hereinbelow, the preparation of the benzoxazinones of the formula I is illustrated by examples; however, the subject matter of the present invention is not limited to the examples given.

EXAMPLES

Example 1

1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

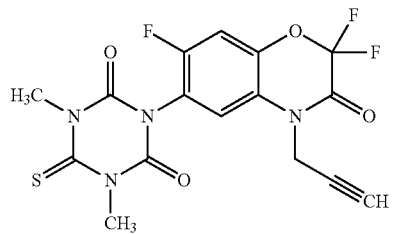 [SMILES: C#CCN1C(=O)C(F)(F)Oc2cc(F)c(-n3c(=O)n(C)c(=S)n(C)c3=O)cc21]

4.1: 2-amino-5-fluorophenol

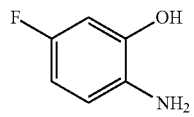

To 5-fluoro-2-nitrophenol (26.63 g, 170 mmol) in Ethanol (250 ml) under $N_2$ atmosphere was added palladium on carbon (10 wt %, 250 mg, 0.235 mmol). The mixture was flushed with $H_2$ and stirred at RT under $H_2$ (balloon) until complete conversion according to thin layer chromatography (TLC) analysis. Pd/C was removed by filtration and the filtrate was concentrated to yield 21.6 g of the title compound.

$^1$H NMR (DMSO): 4.5 (br, 2H); 6.35 (dd, 1H); 6.45 (dd, 1H); 6.50 (dd, 1H); 9.5 (br, 1H).

4.2: 2-bromo-2,2-difluoro-N-(4-fluoro-2-hydroxyphenyl)acetamide

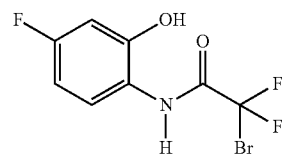 [SMILES: O=C(Nc1ccc(F)cc1O)C(F)(F)Br]

Alternative a)

To 2-amino-5-fluorophenol (14 g, 110 mmol) in dry Tetrahydrofuran at 0° C. was added sodium hydride (55 wt % in mineral oil; 4.81 g, 110 mmol). The resulting mixture was stirred for 15 minutes at −15° C. Subsequently ethyl 2-bromo-2,2-difluoroacetate (24.59 g, 121 mmol) was added dropwise and the resulting mixture was stirred at 0° C. for two hours. The reaction mixture was quenched with saturated aqueous $NH_4Cl$ solution and extracted with ethyl acetate. The combined extracts were washed with brine, dried with $Na_2SO_4$ and concentrated to yield 33 g of the title compound.

$^1$H NMR (DMSO): 3.3 (br, 1H); 6.8 (m, 2H); 7.25 (dd, 1H); 10.4 (br, 1H).

Alternative b)

To 2-amino-5-fluorophenol (200 mg, 1.573 mmol) in dry Tetrahydrofuran at 0° C. was added sodium hydride (55 wt % in mineral oil, 68.6 mg, 1.573 mmol). The resulting mixture was stirred for 15 minutes at −15° C. Subsequently methyl 2-bromo-2,2-difluoroacetate (327 mg, 1.731 mmol) was added dropwise and the resulting mixture was stirred at 0° C. for two hours. The reaction mixture was quenched in saturated aqueous $NH_4Cl$ solution and extracted with ethyl acetate. The combined extracts were washed with brine, dried with $Na_2SO_4$ and concentrated to yield 450 mg of the title compound $^1$H NMR (DMSO): 3.3 (br, 1H); 6.8 (m, 2H); 7.25 (dd, 1H); 10.4 (br, 1H).

4.3: 2,2,7-trifluoro-2H-benzo[b][1,4]oxazin-3(4H)-one

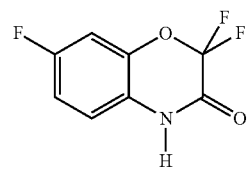 [SMILES: O=C1Nc2ccc(F)cc2OC1(F)F]

To 2-bromo-2,2-difluoro-N-(4-fluoro-2-hydroxyphenyl)acetamide (33 g, 116 mmol) in dry Toluene was added 1,8-Diazabicyclo[5.4.0]undec-7-en (DBU, 17.51 ml, 116 mmol).

The resulting mixture was stirred overnight at 80° C. The reaction was quenched in saturated aqueous NH₄Cl solution and extracted with ethyl acetate. The combined extracts were washed with brine, dried with Na₂SO₄ and concentrated to afford 24.94 g of the title compound.

GCMS m/e (M+)=203

4.4: 2,2,7-trifluoro-6-nitro-2H-benzo[b][1,4]oxazin-3(4H)-one

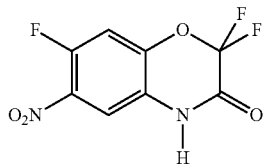 [SMILES: O=C1Nc2cc([N+](=O)[O-])c(F)cc2OC1(F)F]

2,2,7-trifluoro-2H-benzo[b][1,4]oxazin-3(4H)-one (2.5 g, 12.31 mmol) was dissolved in sulfuric acid (40 ml, 750 mmol). The reaction mixture was cooled to 0-5° C. Slowly nitric acid (1.761 ml, 39.7 mmol) was added dropwise and the temperature was maintained between 0-5° C. The reaction mixture was stirred for 30 min at this temperature. Then the reaction mixture was added dropwise to vigorously stirred cold water. A solid was formed, extraction with Dichloromethane. The combined extracts were dried over Na₂SO₄, and concentrated to yield 2.56 g of the title compound as brown solid.

GC/MS m/e (M+)=248
1H-NMR (CDCl₃): 2.9 (br, 1H); 7.15 (d, 1H); 7.80 (d, 1H).

4.5: 2,2,7-trifluoro-6-nitro-4-(prop-2-ynyl)-2Hbenzo[b][1,4]oxazin-3(4H)-one

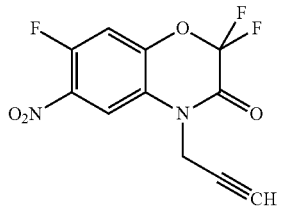 [SMILES: C#CCN1C(=O)C(F)(F)Oc2cc(F)c([N+](=O)[O-])cc21]

To 2,2,7-trifluoro-6-nitro-2H-benzo[b][1,4]oxazin-3(4H)-one (6.9 g, 27.8 mmol) and potassium carbonate (4.61 g, 33.4 mmol) in dry N,N-Dimethylformamide at RT was dropwise added 3-bromoprop-1-yne (80 wt % in toluene; 4.96 g, 33.4 mmol). The resulting mixture was stirred at RT overnight. The reaction mixture was poured in saturated aqueous NH₄Cl solution and extracted with ethyl acetate. The combined extracts were washed with aqueous NaCl solution, dried with Na₂SO₄, concentrated and chased with toluene to yield 7.06 g of the title compound as dark brown solid.

GCMS m/e (M+)=286

4.6: 6-amino-2,2,7-trifluoro-4-(prop-2-ynyl)-2Hbenzo[b][1,4]oxazin-3(4H)-one

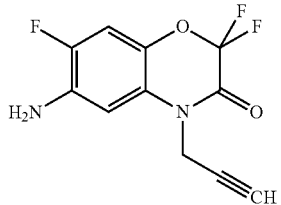

To ammonium chloride (3.96 g, 74.0 mmol) in water was added iron powder (325 mesh; 4.13 g, 74.0 mmol). To the resulting mixture was added 2,2,7-trifluoro-6-nitro-4-(prop-2-ynyl)-2Hbenzo[b][1,4]oxazin-3(4H)-one (7.06 g, 24.67 mmol) in methanol/tetrahydrofuran. The resulting mixture was stirred vigorously at 70° C. for 2 hours. The reaction was quenched in water/ethyl acetate under stirring. The resulting 2 phase system was filtered and the layers were separated. The water layer was subsequently extracted with ethyl acetate. The combined organic phases were washed with brine, dried with Na₂SO₄ and concentrated to yield 5.15 g of the title compound.

GCMS m/e (M+)=256

4.7: 2,2,7-trifluoro-6-isocyanato-4-(prop-2-ynyl)-2Hbenzo[b][1,4]oxazin-3(4H)-one

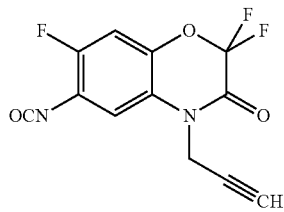

To 6-amino-2,2,7-trifluoro-4-(prop-2-ynyl)-2H-benzo[b][1,4]oxazin-3(4H)-one (5.1 g, 19.91 mmol) in dry toluene was dropwise added diphosgene (2.64 ml, 21.90 mmol) in dry toluene. The resulting mixture was stirred overnight at reflux. Concentrated and chased with toluene and used as such in the next step.

4.8: 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

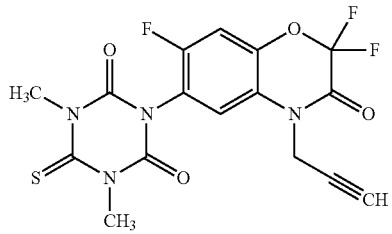

To 1,3-dimethylthiourea (2.489 g, 23.89 mmol) and triethylamine (2.78 ml, 19.91 mmol) in dry toluene was added 2,2,7-trifluoro-6-isocyanato-4-(prop-2-ynyl)-2H-benzo[b][1,4]oxazin-3(4H)-one (5.62 g, 19.91 mmol) in dry toluene. Hereto was subsequently added carbonyldiimidazole (CDI; 6.46 g, 39.8 mmol) and the resulting mixture was stirred at 80° C. overnight. Then the reaction mixture was cooled to room temperature and poured into ethyl acetate/water under stirring. The layers were separated and the aqueous layer was extracted with dichloromethane. The combined extracts were washed with brine, dried with Na₂SO₄ and concentrated to yield 14.4 g.

This residue was stirred in dichloromethane/methanol, the precipitate was isolated over glass filter. The filtrate was concentrated to yield 7.2 g of the title compound.

GCMS m/e (M+)=412

$^1$H-NMR (DMSO): 3.49 (s, 1H); 3.64 (s, 6H); 4.71 (s, 2H); 7.8 (m, 2H).

Use Examples

The herbicidal activity of the benzoxazinones of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments belonged to the following species:

| Bayer Code | Scientific name | Common name |
|---|---|---|
| AMBEL | *Ambrosia elatior* | common ragweed |
| BRAPL | *Brachiaria plantaginea* | alexandergrass |
| SETFA | *Setaria faberi* | giant foxtail |

At an application rate of 0.025 kg/ha, the compound I.a.32 applied by the post-emergence method, showed very good herbicidal activity against BRAPL and SETFA.

At an application rate of 0.050 kg/ha, the compound I.a.32 applied by the pre-emergence method, showed very good herbicidal activity against AMBEL.

At an application rate of 0.025 kg/ha, the compound I.a.35 applied by the post-emergence method, showed very good herbicidal activity against BRAPL and SETFA.

At an application rate of 0.050 kg/ha, the compound I.a.35 applied by the pre-emergence method, showed very good herbicidal activity against AMBEL.

Example 2

The herbicidal action of the compositions according to the invention was demonstrated by the following greenhouse experiments:

The culture containers used were plastic pots containing loamy sand with approximately 3.0% of humus as substrate. The seeds of the test plants were sown separately for each species.

For the pre-emergence treatment, the active compounds, suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants unless this was adversely affected by the active compounds.

For the post-emergence treatment, the test plants were grown to a plant height of from 3 to 15 cm, depending on the plant habit, and only then treated with the active compounds which had been suspended or emulsified in water. To this end, the test plants were either sown directly and grown in the same containers, or they were first grown separately as seedlings and transplanted into the test containers a few days prior to treatment.

Depending on the species, the plants were kept at 10-25° C. and 20-35° C., respectively. The test period extended over 2 to 4 weeks. During this time, the plants were tended and their response to the individual treatments was evaluated.

Evaluation was carried out using a scale from 0 to 100. 100 means no emergence of the plants, or complete destruction of at least the above-ground parts, and 0 means no damage or normal course of growth. Good herbicidal activity is given at values of at least 70, and very good herbicidal activity is given at values of at least 85.

The respective stated components A and B, and if appropriate, C were formulated as a 10% by weight strength emulsion concentrate and, with addition of the amount of solvent system, introduced into the spray liquor used for applying the active compound. In the examples, the solvent used was water.

The test period extended over 20 and 21 days, respectively. During this time, the plants were tended, and their reaction to the treatment with active compound was monitored.

In the examples below, using the method of S. R. Colby (1967) "Calculating synergistic and antagonistic responses of herbicide combinations", Weeds 15, p. 22ff., the value E, which is expected if the activity of the individual active compounds is only additive, was calculated.

$$E = X + Y - (X \cdot Y/100)$$

where

X=percent activity using active compound A at an application rate a;

Y=percent activity using active compound B at an application rate b;

E=expected activity (in %) by A+B at application rates a+b.

If the value found experimentally is higher than the value E calculated according to Colby, a synergistic effect is present.

The following active compounds have been tested:
benzoxazinone of formula I.a.35
saflufenacil (group b 4): herbicide B.76
glyphosate (group b 6): herbicide B.95
pendimethalin (group b 9): herbicide B.101
dimethenamid-p (group b 10): herbicide B.106
pyroxasulfone (group b 10): herbicide B.116

The plants used in the greenhouse experiments were of the following species:

| Bayer code | Scientifc name | English name |
|---|---|---|
| ALOMY | *Alopercurus myosuroides* | blackgrass |
| AMARE | *Amaranthus retroflexus* | common amaranth |
| AMBEL | *Ambrosia artemisiifolia* | common ragweed |
| BIDPI | *Bidens pilosa* | blackjack |
| BRADE | *Brachiaria deflexa* | — |
| BRAPL | *Brachiaria plantaginea* | alexandergrass |
| CHEAL | *Chenopodium album* | lampsquaters |
| ECHCG | *Echinocloa crus-galli* | comon barnyardgrass |
| ERBVI | *Eriochloa villosa* | woolly cupgrass |
| ELEIN | *Eleusine indica* | wiregrass |
| PANDI | *Panicum dichotomiflorun* | fall *panicum* |
| POAAN | *Poa annus* | annual bluegrass |
| POLCO | *Polygonum convolvulus* | wild buckwheat |
| SETLU | *Setaria lutescens* | yellow foxtail |
| SETFA | *Setaria faberi* | Faber's foxtail |
| SETVI | *Setaria viridis* | green foxtail |
| SORHA | *Sorghum halepense* | johnsongrass |

The results of these tests are given below in the use examples and demonstrate the synergistic effect of the mixtures comprising at least one benzoxazinone of the formula I and at least one herbicide B. In this context, a.s. means active substance, based on 100% active ingredient.

Example 2.1

Synergistic Herbicidal Action of the Mixture 1.76 Applied by the Pre-Emergence Method

| application rate a.s. in g/ha | | herbicidal activity against | | | |
|---|---|---|---|---|---|
| | | AMBEL | | BIDPI | |
| I.a.35 | B.76 | found | calculated | found | calculated |
| 12.5 | — | 60 | — | 30 | — |
| — | 6.25 | 75 | — | 60 | — |
| 12.5 | 6.25 | 100 | 90 | 80 | 72 |

Example 2.2

Synergistic Herbicidal Action of the Mixture 1.76 Applied by the Pre-Emergence Method

| application rate a.s. in g/ha | | herbicidal activity against | | | |
|---|---|---|---|---|---|
| | | ELEIN | | SORHA | |
| I.a.35 | B.76 | found | calculated | found | calculated |
| 12.5 | — | 45 | — | 60 | — |
| — | 6.25 | 30 | — | 0 | — |
| 12.5 | 6.25 | 85 | 62 | 70 | 60 |

Example 2.3

Synergistic Herbicidal Action of the Mixture 1.76 Applied by the Post-emergence Method

| application rate a.s. in g/ha | | herbicidal activity against | | | |
|---|---|---|---|---|---|
| | | BRAPL | | SETFA | |
| I.a.35 | B.76 | found | calculated | found | calculated |
| 12.5 | — | 65 | — | 75 | — |
| — | 12.5 | 30 | — | 30 | — |
| 12.5 | 12.5 | 95 | 76 | 95 | 83 |

Example 2.4

Synergistic Herbicidal Action of the Mixture 1.76 Applied by the Post-Emergence Method

| application rate a.s. in g/ha | | herbicidal activity against | | | |
|---|---|---|---|---|---|
| | | ERBVI | | SORPHA | |
| I.a.35 | B.76 | found | calculated | found | calculated |
| 12.5 | — | 70 | — | 80 | — |
| — | 12.5 | 60 | — | 25 | — |
| 12.5 | 12.5 | 100 | 88 | 95 | 85 |

Example 2.5

Synergistic Herbicidal Action of the Mixture 1.95 Applied by the Post-Emergence Method

| application rate a.s. in g/ha | | herbicidal activity against | | | | | |
|---|---|---|---|---|---|---|---|
| | | ALOMY | | BRAPL | | ECHCG | |
| I.a.35 | B.95 | found | calculated | found | calculated | found | calculated |
| 12.5 | — | 30 | — | 65 | — | 75 | — |
| — | 135 | 80 | — | 95 | — | 85 | — |
| 12.5 | 135 | 95 | 86 | 100 | 98 | 98 | 96 |

Example 2.6

Synergistic Herbicidal Action of the Mixture 1.101 Applied by the Pre-Emergence Method

| application rate a.s. in g/ha | | herbicidal activity against | | | |
|---|---|---|---|---|---|
| | | ALOMY | | POLCO | |
| I.a.35 | B.101 | found | calculated | found | calculated |
| 25 | — | 65 | — | 65 | — |
| — | 400 | 75 | — | 40 | — |
| 25 | 400 | 100 | 91 | 95 | 79 |

Example 2.7

Synergistic Herbicidal Action of the Mixture 1.106 Applied by the Pre-Emergence Method

| application rate a.s. in g/ha | | herbicidal activity against | | | |
|---|---|---|---|---|---|
| | | ECHCG | | SETVI | |
| I.a.35 | B.106 | found | calculated | found | calculated |
| 12.5 | — | 30 | — | 90 | — |
| — | 15 | 85 | — | 70 | — |
| 12.5 | 15 | 95 | 90 | 100 | 97 |

Example 2.8

Synergistic Herbicidal Action of the Mixture 1.106 Applied by the Pre-Emergence Method

| application rate a.s. in g/ha | | herbicidal activity against CHEAL | |
|---|---|---|---|
| I.a.35 | B.106 | found | calculated |
| 6.25 | — | 85 | — |
| — | 15 | 10 | — |
| 6.25 | 15 | 100 | 87 |

Example 2.9

Synergistic Herbicidal Action of the Mixture 1.116 Applied by the Pre-Emergence Method

| application rate a.s. in g/ha | | herbicidal activity against | | | | | |
|---|---|---|---|---|---|---|---|
| | | BRAPL | | ERBVI | | AMBEL | |
| I.a.35 | B.116 | found | calculated | found | calculated | found | calculated |
| 25 | — | 50 | — | 55 | — | 75 | — |
| — | 6.25 | 30 | — | 45 | — | 0 | — |
| 25 | 6.25 | 75 | 65 | 90 | 75 | 80 | 75 |

Example 2.10

Synergistic Herbicidal Action of the Mixture 24.106 Applied by the Pre-Emergence Method

| application rate a.s. in g/ha | | | herbicidal activity against | | | |
|---|---|---|---|---|---|---|
| | | | AMARE | | CHEAL | |
| I.a.35 | B.106 | B.76 | found | calculated | found | calculated |
| 3.12 | — | — | 70 | — | 85 | — |
| — | 15 | — | 75 | — | 10 | — |
| — | — | 3.12 | 35 | — | 30 | — |
| 3.12 | 15 | 3.12 | 100 | 95 | 100 | 91 |

What is claimed is:

1. A compound of formula IV:

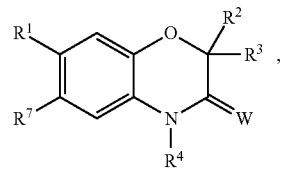

wherein $R^1$ is halogen;

$R^2$ is halogen;

$R^3$ is hydrogen or halogen;

$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl; and $R^7$ is hydrogen, $NO_2$, $NH_2$, —NCO or —NH—C(O)—$NR^5$—C(Z)—$NHR^6$, wherein $R^5$ is hydrogen, $NH_2$, $C_1$-$C_6$-alkyl or $C_3$-$C_6$-alkynyl;

$R^6$ is hydrogen or $C_1$-$C_6$-alkyl;

Z is O or S; and

W is O or S.

2. The compound according to claim 1, wherein $R^7$ is hydrogen.

3. The compound according to claim 1, wherein $R^7$ is $NO_2$.

4. The compound according to claim 1, wherein $R^7$ is $NH_2$.

5. A process for preparing a compound of claim 2, comprising cyclizing a compound of formula V:

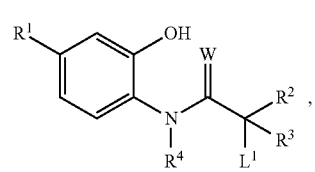

wherein

L¹ is Cl, Br or I;

R¹ is halogen;

R² is halogen;

R³ is hydrogen or halogen;

R⁴ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl; and W is O or S, to form a compound of formula IV.a:

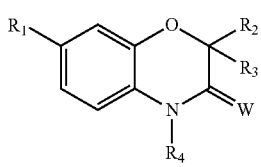

IV.a wherein

R¹ is halogen;

R² is halogen;

R³ is hydrogen or halogen;

R⁴ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl; and W is O or S.

6. The compound of claim 2, wherein the compound is of the structure:

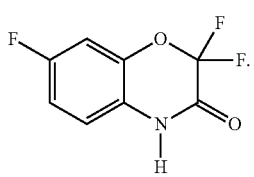 [SMILES: O=C1Nc2ccc(F)cc2OC1(F)F]

7. The compound of claim 3, wherein the compound is selected from:

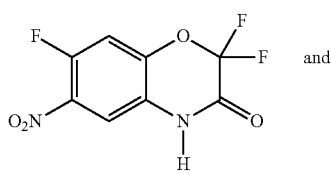 and

8. The compound of claim 4, wherein the compound is of the structure:

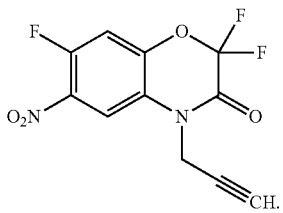 [SMILES: C#CCN1C(=O)C(F)(F)Oc2cc(F)c(N)cc21]

9. A process for preparing a compound of claim 3 comprising cyclizing a compound of formula V:

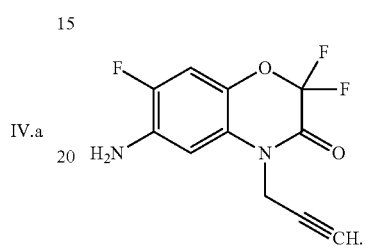

V wherein

L¹ is Cl, Br or I;

R¹ is halogen;

R² is halogen;

R³ is hydrogen or halogen;

R⁴ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl; and W is O or S, to form a compound of formula IV.a:

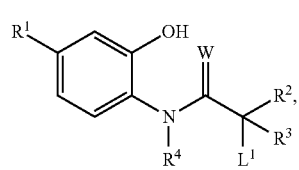

IV.a nitrating the compound of formula IV.a to form a compound of formula IV.b:

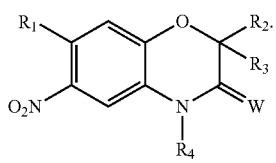

10. A process for preparing a compound of claim 4 comprising cyclizing a compound of formula V:

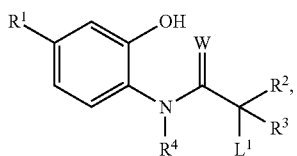

wherein $L^1$ is Cl, Br or I;

$R^1$ is halogen;

$R^2$ is halogen;

$R^3$ is hydrogen or halogen;

$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl; and W is O or S, to form a compound of formula IV.a:

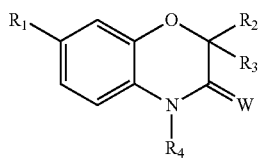

nitrating the compound of formula IV.a to form a compound of formula IV.b:

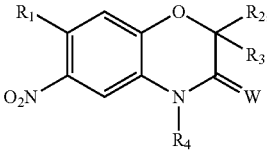

and reducing the compound of formula IV.b to form a compound of formula IV.c:

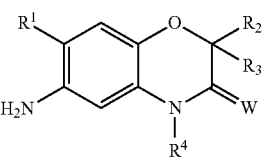

* * * * *